US012741993B2

(12) United States Patent
Frisch et al.

(10) Patent No.: US 12,741,993 B2
(45) Date of Patent: Sep. 22, 2026

(54) **METHODS AND COMPOSITIONS FOR PRODUCING PROTEINS OF INTEREST IN PIGMENT DEFICIENT *BACILLUS* CELLS**

(71) Applicant: DANISCO US INC., Palo Alto, CA (US)

(72) Inventors: Ryan L. Frisch, Newark, DE (US); Ibrahim Halloum, Santa Clara, CA (US); Mikhail Karymov, Newark, CA (US); Christopher John Webb, Menlo Park, CA (US)

(73) Assignee: DANISCO US INC., Palo Alto, CA (US)

( * ) Notice: Subject to any disclaimer, the term of this patent is extended or adjusted under 35 U.S.C. 154(b) by 339 days.

(21) Appl. No.: 18/273,417

(22) PCT Filed: Feb. 22, 2022

(86) PCT No.: PCT/US2022/017339

§ 371 (c)(1),
(2) Date: Jul. 20, 2023

(87) PCT Pub. No.: WO2022/178432

PCT Pub. Date: Aug. 25, 2022

(65) Prior Publication Data

US 2024/0101611 A1 Mar. 28, 2024

Related U.S. Application Data

(60) Provisional application No. 63/151,931, filed on Feb. 22, 2021.

(51) Int. Cl.

| | |
|---|---|
| ***C12P 21/06*** | (2006.01) |
| ***C07K 14/32*** | (2006.01) |
| ***C12N 9/54*** | (2006.01) |
| ***C12N 15/75*** | (2006.01) |
| ***C12P 21/02*** | (2006.01) |

(52) U.S. Cl.
CPC ................ *C07K 14/32* (2013.01); *C12N 9/54* (2013.01); *C12N 15/75* (2013.01)

(58) Field of Classification Search
None
See application file for complete search history.

(56) References Cited

FOREIGN PATENT DOCUMENTS

| | | |
|---|---|---|
| WO | 2003054163 A2 | 7/2003 |
| WO | 2004011609 A2 | 2/2004 |

OTHER PUBLICATIONS

Mikayama et al. (Nov. 1993. Proc. Natl.Acad.Sci. USA, vol. 90 : 10056-10060).*
Rudinger et al. (Jun. 1976. Peptide Hormones. Biol. Council. pp. 5-7).*
Arnaouteli et al., "Pulcherrimin formation controls growth arrest of the Bacillus subtilis biofilm", PNAS, 116(27): 13553-13562, 2019.
Randazzo et al, "The MarR-like protein PchR (YvmB) regulates expression of genes involved in pulcherriminic acid biosynthesis and in the initiation of sporulation in Bacillus subtilis", BMC Microbiology, 16:190, 2016.
Uffen and Canale-Parola, "Synthesis of Pulcherriminic Acid by Bacillus subtilis", Journal of Bacteriology 111:86-93, 1972.
Wang et al., "Regulation of the Synthesis and Secretion of Iron Chelator Cyclopeptide Pulcherriminic Acid in Bacillus licheniformis", Applied Environmental Microbiology, vol. 84, No. 13, 2018.
Wang et al., "Multistep Metabolic Engineering of Bacillus licheniformis to Improve Pulcherriminic Acid Production", Applied Environmental Microbiology, Feb. 28, 2020.
International Search Report and Written Opinion from PCT App. No. PCT/US2022/017339 dated Jun. 14, 2022, 14 pages.

* cited by examiner

*Primary Examiner* — Jennifer E Graser

(57) ABSTRACT

Certain embodiments of the disclosure are related to compositions and methods for producing proteins of interest in pigment deficient *Bacillus* cells. Certain other embodiments are related to compositions and methods for obtaining pigment deficient *Bacillus* cells. Certain other embodiments are related to compositions and methods for growing/cultivating/fermenting pigment deficient *Bacillus* cells. Certain other embodiments are therefore related to compositions and methods for producing, isolating, recovering and the like proteins of interest that are pigment deficient.

14 Claims, 15 Drawing Sheets

Specification includes a Sequence Listing.

SEQUENCE LISTING

```
<160> NUMBER OF SEQ ID NOS: 48

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1

cgggcccgcc tcctagcgg                                                     19


<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2

cgcttttggc ttcctcaggc g                                                  21


<210> SEQ ID NO 3
<211> LENGTH: 102
<212> TYPE: DNA
<213> ORGANISM: Artificial Sequence
<220> FEATURE:
<223> OTHER INFORMATION: primer

<400> SEQUENCE: 3

taaacccttg catatgtcta gataacttcg tataatgtat gctatacgaa gttatgcggc       60

cgccatatgc atcctaggcc ccaagaggag cggaatgagc gc                          102


<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4

ggccgtgctg atcatagcag g                                                  21


<210> SEQ ID NO 5
<211> LENGTH: 104
<212> TYPE: DNA
<213> ORGANISM: Artificial Sequence
<220> FEATURE:
<223> OTHER INFORMATION: primer

<400> SEQUENCE: 5

cgccaatgtt ttcgccgcag aagcgcacga aacaaaaaaa gcaccacatg taaaaaagct       60

gcctttgcgg gcagcttttt tcgacggtat cttattgcgg atcc                        104
```

<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6
ctagacatat gcaagggttt attgt 25

<210> SEQ ID NO 7
<211> LENGTH: 74
<212> TYPE: DNA
<213> ORGANISM: Artificial Sequence
<220> FEATURE:
<223> OTHER INFORMATION: primer

<400> SEQUENCE: 7
aggatgaaag aaggcagcag atacagctcc gcctgaggaa gccaaaagcg taagaaaagt 60
gattctggga gagc 74

<210> SEQ ID NO 8
<211> LENGTH: 31
<212> TYPE: DNA
<213> ORGANISM: Artificial Sequence
<220> FEATURE:
<223> OTHER INFORMATION: primer

<400> SEQUENCE: 8
agtagttcac cacctttcc ctatataaaa g 31

<210> SEQ ID NO 9
<211> LENGTH: 105
<212> TYPE: DNA
<213> ORGANISM: Artificial Sequence
<220> FEATURE:
<223> OTHER INFORMATION: primer

<400> SEQUENCE: 9
accgctcgtg ttcatcagga agaggataac aggatgaaag aaggcagcag atacagctcc 60
gcctgaggaa gccaaaagcg taaatccttg acgagcaagg gattg 105

<210> SEQ ID NO 10
<211> LENGTH: 28
<212> TYPE: DNA
<213> ORGANISM: Artificial Sequence
<220> FEATURE:
<223> OTHER INFORMATION: primer

<400> SEQUENCE: 10
atacattcag ttcgtttatt atcatttc 28

<210> SEQ ID NO 11
<211> LENGTH: 106
<212> TYPE: DNA
<213> ORGANISM: Artificial Sequence
<220> FEATURE:
<223> OTHER INFORMATION: primer

<400> SEQUENCE: 11
accgctcgtg ttcatcagga agaggataac aggatgaaag aaggcagcag atacagctcc 60
gcctgaggaa gccaaaagcg atattttgag ctgaaatcga agcagg 106

<210> SEQ ID NO 12
<211> LENGTH: 28
<212> TYPE: DNA
<213> ORGANISM: Artificial Sequence
<220> FEATURE:
<223> OTHER INFORMATION: primer

<400> SEQUENCE: 12
gtatagagta aaggttctat gtaaaaag 28

<210> SEQ ID NO 13
<211> LENGTH: 89
<212> TYPE: DNA
<213> ORGANISM: Artificial Sequence
<220> FEATURE:
<223> OTHER INFORMATION: primer

<400> SEQUENCE: 13
ttcagaaaaa atcgtggaat tgatacacta atgcttttat atagggaaaa ggtggtgaac 60
tactttggct catacaaaat caaaggcag 89

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
aaaaagctgc ccgcaaaggc ag 22

<210> SEQ ID NO 15
<211> LENGTH: 107
<212> TYPE: DNA
<213> ORGANISM: Artificial Sequence
<220> FEATURE:
<223> OTHER INFORMATION: primer

<400> SEQUENCE: 15
ttgctctcat ttttttctga gacaggttta gaatcagact gaactgtgaa gaaatgataa 60
taaacgaact gaatgtatcc taatgctttt atatagggaa aaggtgg 107

<210> SEQ ID NO 16
<211> LENGTH: 107
<212> TYPE: DNA
<213> ORGANISM: Artificial Sequence
<220> FEATURE:
<223> OTHER INFORMATION: primer

<400> SEQUENCE: 16
tatacaaaaa aacgcactga tttacaaaac cttaacattc ggttcaaacc ctttttacat 60
agaaccttta ctctatacgt taatgctttt atatagggaa aaggtgg 107

<210> SEQ ID NO 17
<211> LENGTH: 157
<212> TYPE: DNA
<213> ORGANISM: Artificial Sequence
<220> FEATURE:
<223> OTHER INFORMATION: primer

<400> SEQUENCE: 17
accgctcgtg ttcatcagga agaggataac aggatgaaag aaggcagcag atacagctcc 60
gcctgaggaa gccaaaagcg gatttatgtt tcagcaggaa ttgtaaaggg taaaagagaa 120
atagatacat taatgctttt atatagggaa aaggtgg 157

<210> SEQ ID NO 18
<211> LENGTH: 3578
<212> TYPE: DNA
<213> ORGANISM: Artificial Sequence
<220> FEATURE:
<223> OTHER INFORMATION: expression cassette

<400> SEQUENCE: 18
cgggcccgcc tcctagcggc tgaagaatcg cggctgccag cttataaata aaagcgaggg 60
aaagcacttt gattgccgga aatgccgcaa tacagatcaa aatagcgaca ccgagaatcc 120
ctaccgtatt tttcagcagt aaagaggcgc tgattactgt atctgttgcg tctgtaaaca 180
ttcggccaag cacaggaata aaatttccgg ttataaattt agccgtcctg agcgtaatgc 240
cgtctgtcac tgcagctgac gctccctgaa cagagatgac gccgagaaag atggtaagaa 300
aaacagccag tgctccgatg gcgatatttc tgagcaggtt agccagctgc gttactttgt 360
attgttcagt catcgtgctg acaatgctca gaatcgctga taaaaaaatc agcggcatga 420
cgatattctg aatcaagaga ccgctcgtgt tcatcaggaa gaggataaca ggatgaaaga 480
aggcagcaga tacagctccg cctgaggaag ccaaaagcgt aagaaaagtg attctgggag 540
agccgggatc actttttat ttaccttatg cccgaaatga aagctttatg acctaattgt 600
gtaactatat cctatttttt caaaaaatat tttaaaaacg agcaggattt cagaaaaaat 660
cgtggaattg atacactaat gcttttatat agggaaaagg tggtgaacta ctttggctca 720
tacaaaatca aaggcagtat tgatcttata cactgtttgc ttcagtgcat tttttgcatc 780
tttaagccag aacatttatt cacctattct tccgatcatt aaagaatcat tccatgtttc 840
cacagctatg gtgaacctgt cagtctcagt ttttatgatt gtgacagcaa taatgcaaat 900
tatattagga gcgatcattg attttaaagg cgctcggatc gtcttgatta ccggtattct 960
ggcaacggca gcagccagca tcggctgtgc ggtgactact gactttacct tgtttctgat 1020
attcagaatg atacaggcag ccggttccgc agcactgcct cttattgctg ccacaacgat 1080
cggacagctg tttacaggaa atgaacgcgg gagtgcaatg ggaacgtatc aaatgctcct 1140
gtctgtcgca ccggctattg ctccagttct aggaggattc ataggcggag cagccggata 1200
cgaagggatt ttttggatac ttgcggccat ctctatcgtt ttgctggtga caaacagcat 1260
cacctttcct aaagattctc caactgaatc tatgcagcaa gccaaaggca atgtgttcgc 1320
tcattataaa tcaatattta caaatcgaac agggaacgtc attttgactt taagttttgt 1380 tctcttttc atttattttg cagtaattgt ctacctccca atattgctga cagagcatta 1440
ccatatagat gtgggtatag caggactgtt atatttgccg ctggcgctga gcacgattgc 1500
aggtacgttt ctgtttaaaa gaatacaggc aaaaatcggg ctgcacacct tgtttatcgg 1560
aagcaatgtg attgccgcct gcagcatcat tttatttgct gttacacatt ccgtttctct 1620
cgttctcatg gctctgacgc tggcactgtt tggcatctcg atgggggtta ttcctccctt 1680
gtactctaca atgattacta atgaatttga gcacaacaga gggagtgcaa tcggaatgtt 1740
taactttatc cgatatacag gcatggcagc aggtccgatg gtatctgcct acttgctcac 1800
aatgatgccg tctgccatgt cctttagcct cctaggcctt ggatttgccg cattgagctt 1860
ttgccttctt ccgccaatgt tttcgccgca gaagcgcacg aaacaaaaaa agcaccacat 1920
gtaaaaaagc tgcctttgcg ggcagctttt ttcgacggta tcttattgcg gatccataac 1980

```
ttcgtataat gtatgctata cgaagttatc tagataaaaa atttagaagc caatgaaatc   2040

tataaataaa ctaaattaag tttatttaat taacaactat ggatataaaa taggtactaa   2100

tcaaaatagt gaggaggata tatttgaata catacgaaca aattaataaa gtgaaaaaaa   2160

tacttcggaa acatttaaaa aataacctta ttggtactta catgtttgga tcaggagttg   2220

agagtggact aaaaccaaat agtgatcttg actttttagt cgtcgtatct gaaccattga   2280

cagatcaaag taaagaaata cttatacaaa aaattagacc tatttcaaaa aaaataggag   2340

ataaaagcaa cttacgatat attgaattaa caattattat tcagcaagaa atggtaccgt   2400

ggaatcatcc tcccaaacaa gaatttattt atggagaatg gttacaagag ctttatgaac   2460

aaggatacat tcctcagaag gaattaaatt cagatttaac cataatgctt taccaagcaa   2520

aacgaaaaaa taaaagaata tacggaaatt atgacttaga ggaattacta cctgatattc   2580

cattttctga tgtgagaaga gccattatgg attcgtcaga ggaattaata gataattatc   2640

aggatgatga aaccaactct atattaactt tatgccgtat gattttaact atggacacgg   2700

gtaaaatcat accaaaagat attgcgggaa atgcagtggc tgaatcttct ccattagaac   2760

atagggagag aattttgtta gcagttcgta gttatcttgg agagaatatt gaatggacta   2820

atgaaaatgt aaatttaact ataaactatt taaataacag attaaaaaaa ttataaaaaa   2880

attgaaaaaa tggtggaaac actttttca attttttgt tttattattt aatatttggg   2940

aaatattcat tctaattggt aatcagattt tagaaaacaa taaacccttg catatgtcta   3000

gataacttcg tataatgtat gctatacgaa gttatgcggc cgccatatgc atcctaggcc   3060

ccaagaggag cggaatgagc gccaggataa agctggtcat cgtctgaatc gcctcagttg   3120

catagttaat tgccacatga aagctattaa gcgcaaggat aatcagcacc atgtacacaa   3180

ttgagtaagc gaccttactg acggtgcttt gctgaaaagc attttgcaaa agctgcagaa   3240

tgacgcaaaa aatcgtgagc aaaatcaatg tgcccagcag ctttccgttg gcaagcactt   3300

catgaaacaa ataagaaaag agagctttca gccattcttg cggtgagaat gatttatcgc   3360

cattgataaa ctccattaag ctgccttttt ggctttccgg cagcagtccg ccgtattctg   3420

tcataatgtc attccaaaat tccccgatct tatctgtttc aagcgaggct gctgtccttt   3480

ccgctaattg ctcggctgtt tcagcatggt cttccgtttg ttctgcatta ccagctgctt   3540

gtacaatttc tgcacggcct gctatgatca gcacggcc                           3578
```

<210> SEQ ID NO 19
<211> LENGTH: 3655
<212> TYPE: DNA
<213> ORGANISM: Artificial Sequence
<220> FEATURE:
<223> OTHER INFORMATION: expression cassette

<400> SEQUENCE: 19

```
cgggcccgcc tcctagcggc tgaagaatcg cggctgccag cttataaata aaagcgaggg     60

aaagcacttt gattgccgga aatgccgcaa tacagatcaa aatagcgaca ccgagaatcc    120

ctaccgtatt tttcagcagt aaagaggcgc tgattactgt atctgttgcg tctgtaaaca    180

ttcggccaag cacaggaata aaatttccgg ttataaattt agccgtcctg agcgtaatgc    240

cgtctgtcac tgcagctgac gctccctgaa cagagatgac gccgagaaag atggtaagaa    300

aaacagccag tgctccgatg gcgatatttc tgagcaggtt agccagctgc gttactttgt    360

attgttcagt catcgtgctg acaatgctca gaatcgctga taaaaaaatc agcggcatga    420

cgatattctg aatcaagaga ccgctcgtgt tcatcaggaa gaggataaca ggatgaaaga    480
```

```
aggcagcaga tacagctccg cctgaggaag ccaaaagcgt aaatccttga cgagcaaggg    540
attgacgctt taaaatgctt gatatggctt tttatatgtg ttactctaca tacagaaatt    600
cttcactttg ttggacaaac attcctcaga gtgcagtttt tcttaaaaag ccgtttaatt    660
gtctttctct tacttgctct catttttttc tgagacaggt ttagaatcag actgaactgt    720
gaagaaatga taataaacga actgaatgta tcctaatgct tttatatagg gaaaaggtgg    780
tgaactactt tggctcatac aaaatcaaag gcagtattga tcttatacac tgtttgcttc    840
agtgcatttt ttgcatcttt aagccagaac atttattcac ctattcttcc gatcattaaa    900
gaatcattcc atgtttccac agctatggtg aacctgtcag tctcagtttt tatgattgtg    960
acagcaataa tgcaaattat attaggagcg atcattgatt ttaaaggcgc tcggatcgtc   1020
ttgattaccg gtattctggc aacggcagca gccagcatcg gctgtgcggt gactactgac   1080
tttaccttgt ttctgatatt cagaatgata caggcagccg gttccgcagc actgcctctt   1140
attgctgcca caacgatcgg acagctgttt acaggaaatg aacgcgggag tgcaatggga   1200
acgtatcaaa tgctcctgtc tgtcgcaccg gctattgctc cagttctagg aggattcata   1260
ggcggagcag ccggatacga agggattttt tggatacttg cggccatctc tatcgttttg   1320
ctggtgacaa acagcatcac ctttcctaaa gattctccaa ctgaatctat gcagcaagcc   1380
aaaggcaatg tgttcgctca ttataaatca atatttacaa atcgaacagg gaacgtcatt   1440
ttgactttaa gttttgttct ctttttcatt tattttgcag taattgtcta cctcccaata   1500
ttgctgacag agcattacca tatagatgtg ggtatagcag gactgttata tttgccgctg   1560
gcgctgagca cgattgcagg tacgtttctg tttaaaagaa tacaggcaaa aatcgggctg   1620
cacaccttgt ttatcggaag caatgtgatt gccgcctgca gcatcatttt atttgctgtt   1680
acacattccg tttctctcgt tctcatggct ctgacgctgg cactgtttgg catctcgatg   1740
gggttattc ctcccttgta ctctacaatg attactaatg aatttgagca caacagaggg    1800
agtgcaatcg gaatgtttaa ctttatccga tatacaggca tggcagcagg tccgatggta   1860
tctgcctact tgctcacaat gatgccgtct gccatgtcct ttagcctcct aggccttgga   1920
tttgccgcat tgagcttttg ccttcttccg ccaatgtttt cgccgcagaa gcgcacgaaa   1980
caaaaaaagc accacatgta aaaaagctgc ctttgcgggc agcttttttc gacggtatct   2040
tattgcggat ccataacttc gtataatgta tgctatacga agttatctag ataaaaaatt   2100
tagaagccaa tgaaatctat aaataaacta aattaagttt atttaattaa caactatgga   2160
tataaaatag gtactaatca aaatagtgag gaggatatat ttgaatacat acgaacaaat   2220
taataaagtg aaaaaaatac ttcggaaaca tttaaaaaat aaccttattg gtacttacat   2280
gtttggatca ggagttgaga gtggactaaa accaaatagt gatcttgact ttttagtcgt   2340
cgtatctgaa ccattgacag atcaaagtaa agaaatactt atacaaaaaa ttagacctat   2400
ttcaaaaaaa ataggagata aaagcaactt acgatatatt gaattaacaa ttattattca   2460
gcaagaaatg gtaccgtgga atcatcctcc caaacaagaa tttatttatg gagaatggtt   2520
acaagagctt tatgaacaag gatacattcc tcagaaggaa ttaaattcag atttaaccat   2580
aatgctttac caagcaaaac gaaaaaataa aagaatatac ggaaattatg acttagagga   2640
attactacct gatattccat tttctgatgt gagaagagcc attatggatt cgtcagagga   2700
attaatagat aattatcagg atgatgaaac caactctata ttaactttat gccgtatgat   2760
tttaactatg gacacgggta aaatcatacc aaaagatatt gcgggaaatg cagtggctga   2820
```

```
atcttctcca ttagaacata gggagagaat tttgttagca gttcgtagtt atcttggaga   2880

gaatattgaa tggactaatg aaaatgtaaa tttaactata aactatttaa ataacagatt   2940

aaaaaaatta taaaaaaatt gaaaaaatgg tggaaacact tttttcaatt tttttgtttt   3000

attatttaat atttgggaaa tattcattct aattggtaat cagattttag aaaacaataa   3060

acccttgcat atgtctagat aacttcgtat aatgtatgct atacgaagtt atgcggccgc   3120

catatgcatc ctaggcccca agaggagcgg aatgagcgcc aggataaagc tggtcatcgt   3180

ctgaatcgcc tcagttgcat agttaattgc cacatgaaag ctattaagcg caaggataat   3240

cagcaccatg tacacaattg agtaagcgac cttactgacg gtgctttgct gaaaagcatt   3300

ttgcaaaagc tgcagaatga cgcaaaaaat cgtgagcaaa atcaatgtgc ccagcagctt   3360

tccgttggca agcacttcat gaaacaaata agaaaagaga gctttcagcc attcttgcgg   3420

tgagaatgat ttatcgccat tgataaactc cattaagctg ccttttttggc tttccggcag   3480

cagtccgccg tattctgtca taatgtcatt ccaaaattcc ccgatcttat ctgtttcaag   3540

cgaggctgct gtcctttccg ctaattgctc ggctgtttca gcatggtctt ccgtttgttc   3600

tgcattacca gctgcttgta caatttctgc acggcctgct atgatcagca cggcc        3655
```

<210> SEQ ID NO 20
<211> LENGTH: 3471
<212> TYPE: DNA
<213> ORGANISM: Artificial Sequence
<220> FEATURE:
<223> OTHER INFORMATION: expression cassette

<400> SEQUENCE: 20

```
cgggcccgcc tcctagcggc tgaagaatcg cggctgccag cttataaata aaagcgaggg     60

aaagcacttt gattgccgga aatgccgcaa tacagatcaa aatagcgaca ccgagaatcc    120

ctaccgtatt tttcagcagt aaagaggcgc tgattactgt atctgttgcg tctgtaaaca    180

ttcggccaag cacaggaata aaatttccgg ttataaattt agccgtcctg agcgtaatgc    240

cgtctgtcac tgcagctgac gctccctgaa cagagatgac gccgagaaag atggtaagaa    300

aaacagccag tgctccgatg gcgatatttc tgagcaggtt agccagctgc gttactttgt    360

attgttcagt catcgtgctg acaatgctca gaatcgctga taaaaaaatc agcggcatga    420

cgatattctg aatcaagaga ccgctcgtgt tcatcaggaa gaggataaca ggatgaaaga    480

aggcagcaga tacagctccg cctgaggaag ccaaaagcgg atttatgttt cagcaggaat    540

tgtaaagggt aaaagagaaa tagatacatt aatgctttta tatagggaaa aggtggtgaa    600

ctactttggc tcatacaaaa tcaaaggcag tattgatctt atacactgtt tgcttcagtg    660

catttttgc atctttaagc cagaacattt attcacctat tcttccgatc attaaagaat    720

cattccatgt ttccacagct atggtgaacc tgtcagtctc agtttttatg attgtgacag    780

caataatgca aattatatta ggagcgatca ttgattttaa aggcgctcgg atcgtcttga    840

ttaccggtat tctggcaacg gcagcagcca gcatcggctg tgcggtgact actgacttta    900

ccttgtttct gatattcaga atgatacagg cagccggttc cgcagcactg cctcttattg    960

ctgccacaac gatcggacag ctgtttacag gaaatgaacg cgggagtgca atgggaacgt   1020

atcaaatgct cctgtctgtc gcaccggcta ttgctccagt tctaggagga ttcataggcg   1080

gagcagccgg atacgaaggg attttttgga tacttgcggc catctctatc gttttgctgg   1140

tgacaaacag catcaccttt cctaaagatt ctccaactga atctatgcag caagccaaag   1200

gcaatgtgtt cgctcattat aaatcaatat ttacaaatcg aacagggaac gtcattttga   1260
```

```
ctttaagttt tgttctcttt ttcatttatt ttgcagtaat tgtctacctc ccaatattgc   1320
tgacagagca ttaccatata gatgtgggta tagcaggact gttatatttg ccgctggcgc   1380
tgagcacgat tgcaggtacg tttctgttta aaagaataca ggcaaaaatc gggctgcaca   1440
ccttgtttat cggaagcaat gtgattgccg cctgcagcat cattttattt gctgttacac   1500
attccgtttc tctcgttctc atggctctga cgctggcact gtttggcatc tcgatggggg   1560
ttattcctcc cttgtactct acaatgatta ctaatgaatt tgagcacaac agagggagtg   1620
caatcggaat gtttaacttt atccgatata caggcatggc agcaggtccg atggtatctg   1680
cctacttgct cacaatgatg ccgtctgcca tgtcctttag cctcctaggc cttggatttg   1740
ccgcattgag cttttgcctt cttccgccaa tgttttcgcc gcagaagcgc acgaaacaaa   1800
aaaagcacca catgtaaaaa agctgccttt gcgggcagct tttttcgacg gtatcttatt   1860
gcggatccat aacttcgtat aatgtatgct atacgaagtt atctagataa aaaatttaga   1920
agccaatgaa atctataaat aaactaaatt aagtttattt aattaacaac tatggatata   1980
aaataggtac taatcaaaat agtgaggagg atatatttga atacatacga acaaattaat   2040
aaagtgaaaa aaatacttcg gaaacattta aaaaataacc ttattggtac ttacatgttt   2100
ggatcaggag ttgagagtgg actaaaacca aatagtgatc ttgacttttt agtcgtcgta   2160
tctgaaccat tgacagatca aagtaaagaa atacttatac aaaaaattag acctatttca   2220
aaaaaaatag gagataaaag caacttacga tatattgaat taacaattat tattcagcaa   2280
gaaatggtac cgtggaatca tcctcccaaa caagaattta tttatggaga atggttacaa   2340
gagctttatg aacaaggata cattcctcag aaggaattaa attcagattt aaccataatg   2400
ctttaccaag caaaacgaaa aaataaaaga atatacggaa attatgactt agaggaatta   2460
ctacctgata ttccattttc tgatgtgaga agagccatta tggattcgtc agaggaatta   2520
atagataatt atcaggatga tgaaaccaac tctatattaa ctttatgccg tatgatttta   2580
actatggaca cgggtaaaat cataccaaaa gatattgcgg gaaatgcagt ggctgaatct   2640
tctccattag aacataggga gagaattttg ttagcagttc gtagttatct tggagagaat   2700
attgaatgga ctaatgaaaa tgtaaattta actataaact atttaaataa cagattaaaa   2760
aaattataaa aaaattgaaa aaatggtgga aacacttttt tcaatttttt tgttttatta   2820
tttaatattt gggaaatatt cattctaatt ggtaatcaga ttttagaaaa caataaaccc   2880
ttgcatatgt ctagataact tcgtataatg tatgctatac gaagttatgc ggccgccata   2940
tgcatcctag gccccaagag gagcggaatg agcgccagga taaagctggt catcgtctga   3000
atcgcctcag ttgcatagtt aattgccaca tgaaagctat taagcgcaag gataatcagc   3060
accatgtaca caattgagta agcgacctta ctgacggtgc tttgctgaaa agcattttgc   3120
aaaagctgca gaatgacgca aaaaatcgtg agcaaaatca atgtgcccag cagctttccg   3180
ttggcaagca cttcatgaaa caaataagaa aagagagctt tcagccattc ttgcggtgag   3240
aatgatttat cgccattgat aaactccatt aagctgcctt tttggctttc cggcagcagt   3300
ccgccgtatt ctgtcataat gtcattccaa aattccccga tcttatctgt ttcaagcgag   3360
gctgctgtcc tttccgctaa ttgctcggct gtttcagcat ggtcttccgt ttgttctgca   3420
ttaccagctg cttgtacaat ttctgcacgg cctgctatga tcagcacggc c            3471
```

<210> SEQ ID NO 21
<211> LENGTH: 3637
<212> TYPE: DNA

<213> ORGANISM: Artificial Sequence
<220> FEATURE:
<223> OTHER INFORMATION: expression cassette

<400> SEQUENCE: 21

```
cgggcccgcc tcctagcggc tgaagaatcg cggctgccag cttataaata aaagcgaggg     60
aaagcacttt gattgccgga aatgccgcaa tacagatcaa aatagcgaca ccgagaatcc    120
ctaccgtatt tttcagcagt aaagaggcgc tgattactgt atctgttgcg tctgtaaaca    180
ttcggccaag cacaggaata aaatttccgg ttataaattt agccgtcctg agcgtaatgc    240
cgtctgtcac tgcagctgac gctccctgaa cagagatgac gccgagaaag atggtaagaa    300
aaacagccag tgctccgatg gcgatatttc tgagcaggtt agccagctgc gttactttgt    360
attgttcagt catcgtgctg acaatgctca gaatcgctga taaaaaaatc agcggcatga    420
cgatattctg aatcaagaga ccgctcgtgt tcatcaggaa gaggataaca ggatgaaaga    480
aggcagcaga tacagctccg cctgaggaag ccaaaagcga tattttgagc tgaaatcgaa    540
gcaggacaaa gaaggtactc agcaaaagaa taaagacaaa attgaagaaa atgcagaaaa    600
cacaacgtct tctgataact aaaaaaaaac gctcacatga tgtgggcgtt tttttatac     660
aaaaaaacgc actgatttac aaaaccttaa cattcggttc aaaccctttt tacatagaac    720
ctttactcta tacgttaatg cttttatata gggaaaaggt ggtgaactac tttggctcat    780
acaaaatcaa aggcagtatt gatcttatac actgtttgct tcagtgcatt ttttgcatct    840
ttaagccaga acatttattc acctattctt ccgatcatta aagaatcatt ccatgtttcc    900
acagctatgg tgaacctgtc agtctcagtt tttatgattg tgacagcaat aatgcaaatt    960
atattaggag cgatcattga ttttaaaggc gctcggatcg tcttgattac cggtattctg   1020
gcaacggcag cagccagcat cggctgtgcg gtgactactg actttacctt gtttctgata   1080
ttcagaatga tacaggcagc cggttccgca gcactgcctc ttattgctgc cacaacgatc   1140
ggacagctgt ttacaggaaa tgaacgcggg agtgcaatgg gaacgtatca aatgctcctg   1200
tctgtcgcac cggctattgc tccagttcta ggaggattca taggcggagc agccggatac   1260
gaagggattt tttggatact tgcggccatc tctatcgttt tgctggtgac aaacagcatc   1320
acctttccta aagattctcc aactgaatct atgcagcaag ccaaaggcaa tgtgttcgct   1380
cattataaat caatatttac aaatcgaaca gggaacgtca ttttgacttt aagttttgtt   1440
ctctttttca tttattttgc agtaattgtc tacctcccaa tattgctgac agagcattac   1500
catatagatg tgggtatagc aggactgtta tatttgccgc tggcgctgag cacgattgca   1560
ggtacgtttc tgtttaaaag aatacaggca aaaatcgggc tgcacacctt gtttatcgga   1620
agcaatgtga ttgccgcctg cagcatcatt ttatttgctg ttacacattc cgtttctctc   1680
gttctcatgg ctctgacgct ggcactgttt ggcatctcga tgggggttat tcctcccttg   1740
tactctacaa tgattactaa tgaatttgag cacaacagag ggagtgcaat cggaatgttt   1800
aactttatcc gatatacagg catggcagca ggtccgatgg tatctgccta cttgctcaca   1860
atgatgccgt ctgccatgtc ctttagcctc ctaggccttg gatttgccgc attgagcttt   1920
tgccttcttc cgccaatgtt ttcgccgcag aagcgcacga aacaaaaaaa gcaccacatg   1980
taaaaaagct gcctttgcgg gcagcttttt tcgacggtat cttattgcgg atccataact   2040
tcgtataatg tatgctatac gaagttatct agataaaaaa tttagaagcc aatgaaatct   2100
ataaataaac taaattaagt ttatttaatt aacaactatg gatataaaat aggtactaat   2160
caaaatagtg aggaggatat atttgaatac atacgaacaa attaataaag tgaaaaaaat   2220
```

```
acttcggaaa catttaaaaa ataaccttat tggtacttac atgtttggat caggagttga   2280

gagtggacta aaaccaaata gtgatcttga ctttttagtc gtcgtatctg aaccattgac   2340

agatcaaagt aaagaaatac ttatacaaaa aattagacct atttcaaaaa aaataggaga   2400

taaaagcaac ttacgatata ttgaattaac aattattatt cagcaagaaa tggtaccgtg   2460

gaatcatcct cccaaacaag aatttattta tggagaatgg ttacaagagc tttatgaaca   2520

aggatacatt cctcagaagg aattaaattc agatttaacc ataatgcttt accaagcaaa   2580

acgaaaaaat aaaagaatat acggaaatta tgacttagag gaattactac ctgatattcc   2640

attttctgat gtgagaagag ccattatgga ttcgtcagag gaattaatag ataattatca   2700

ggatgatgaa accaactcta tattaacttt atgccgtatg attttaacta tggacacggg   2760

taaaatcata ccaaaagata ttgcgggaaa tgcagtggct gaatcttctc cattagaaca   2820

tagggagaga attttgttag cagttcgtag ttatcttgga gagaatattg aatggactaa   2880

tgaaaatgta aatttaacta taaactattt aaataacaga ttaaaaaaat tataaaaaaa   2940

ttgaaaaaat ggtggaaaca ctttttttcaa ttttttttgtt ttattattta atatttggga   3000

aatattcatt ctaattggta atcagatttt agaaaacaat aaacccttgc atatgtctag   3060

ataacttcgt ataatgtatg ctatacgaag ttatgcggcc gccatatgca tcctaggccc   3120

caagaggagc ggaatgagcg ccaggataaa gctggtcatc gtctgaatcg cctcagttgc   3180

atagttaatt gccacatgaa agctattaag cgcaaggata atcagcacca tgtacacaat   3240

tgagtaagcg accttactga cggtgctttg ctgaaaagca ttttgcaaaa gctgcagaat   3300

gacgcaaaaa atcgtgagca aaatcaatgt gcccagcagc tttccgttgg caagcacttc   3360

atgaaacaaa taagaaaaga gagctttcag ccattcttgc ggtgagaatg atttatcgcc   3420

attgataaac tccattaagc tgccttttttg gctttccggc agcagtccgc cgtattctgt   3480

cataatgtca ttccaaaatt ccccgatctt atctgtttca agcgaggctg ctgtcctttc   3540

cgctaattgc tcggctgttt cagcatggtc ttccgtttgt tctgcattac cagctgcttg   3600

tacaatttct gcacggcctg ctatgatcag cacggcc                            3637
```

<210> SEQ ID NO 22
<211> LENGTH: 25
<212> TYPE: DNA
<213> ORGANISM: Artificial Sequence
<220> FEATURE:
<223> OTHER INFORMATION: primer

<400> SEQUENCE: 22

```
gcaaatagga taaacaacac gatgg                                           25
```

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23

```
cgcctatatt gctgaattcg ggg                                             23
```

<210> SEQ ID NO 24
<211> LENGTH: 23
<212> TYPE: DNA
<213> ORGANISM: Artificial Sequence
<220> FEATURE:

<223> OTHER INFORMATION: primer

<400> SEQUENCE: 24
gcgatatttc tgagcaggtt agc 23

<210> SEQ ID NO 25
<211> LENGTH: 25
<212> TYPE: DNA
<213> ORGANISM: Artificial Sequence
<220> FEATURE:
<223> OTHER INFORMATION: primer

<400> SEQUENCE: 25
actcctgatc caaacatgta agtac 25

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
tgccaacgga aagctgctgg g 21

<210> SEQ ID NO 27
<211> LENGTH: 25
<212> TYPE: DNA
<213> ORGANISM: Artificial Sequence
<220> FEATURE:
<223> OTHER INFORMATION: primer

<400> SEQUENCE: 27
cagacggatt ttcgacttac atgag 25

<210> SEQ ID NO 28
<211> LENGTH: 25
<212> TYPE: DNA
<213> ORGANISM: Artificial Sequence
<220> FEATURE:
<223> OTHER INFORMATION: primer

<400> SEQUENCE: 28
ggactcttct tgtttgtgat taacg 25

<210> SEQ ID NO 29
<211> LENGTH: 132
<212> TYPE: PRT
<213> ORGANISM: Bacillus licheniformis

<400> SEQUENCE: 29

```
Met Thr Arg Phe Gly Glu Arg Leu Lys Glu Leu Arg Glu Gln Arg Ser
1               5                   10                  15

Leu Ser Val Asn Gln Leu Ala Met Tyr Ala Gly Val Ser Ala Ala Ala
            20                  25                  30

Ile Ser Arg Ile Glu Asn Gly His Arg Gly Val Pro Lys Pro Ala Thr
        35                  40                  45

Ile Arg Lys Leu Ala Glu Ala Leu Lys Met Pro Tyr Glu Gln Leu Met
    50                  55                  60

Asp Ile Ala Gly Tyr Met Arg Ala Asp Glu Ile Arg Glu Gln Pro Arg
65                  70                  75                  80

Gly Tyr Val Thr Met Gln Glu Ile Ala Ala Lys His Gly Val Glu Asp
                85                  90                  95
```

```
Leu Trp Leu Phe Lys Pro Glu Lys Trp Asp Cys Leu Ser Arg Glu Asp
            100                 105                 110

Leu Leu Asn Leu Glu Gln Tyr Phe His Phe Leu Val Asn Glu Ala Lys
        115                 120                 125

Lys Arg Gln Ser
    130


<210> SEQ ID NO 30
<211> LENGTH: 403
<212> TYPE: PRT
<213> ORGANISM: Bacillus subtilis

<400> SEQUENCE: 30

Met Ala His Thr Lys Ser Lys Ala Val Leu Ile Leu Tyr Thr Val Cys
1               5                   10                  15

Phe Ser Ala Phe Phe Ala Ser Leu Ser Gln Asn Ile Tyr Ser Pro Ile
            20                  25                  30

Leu Pro Ile Ile Lys Glu Ser Phe His Val Ser Thr Ala Met Val Asn
        35                  40                  45

Leu Ser Val Ser Val Phe Met Ile Val Thr Ala Ile Met Gln Ile Ile
    50                  55                  60

Leu Gly Ala Ile Ile Asp Phe Lys Gly Ala Arg Ile Val Leu Ile Thr
65                  70                  75                  80

Gly Ile Leu Ala Thr Ala Ala Ala Ser Ile Gly Cys Ala Val Thr Thr
                85                  90                  95

Asp Phe Thr Leu Phe Leu Ile Phe Arg Met Ile Gln Ala Ala Gly Ser
            100                 105                 110

Ala Ala Leu Pro Leu Ile Ala Ala Thr Thr Ile Gly Gln Leu Phe Thr
        115                 120                 125

Gly Asn Glu Arg Gly Ser Ala Met Gly Thr Tyr Gln Met Leu Leu Ser
    130                 135                 140

Val Ala Pro Ala Ile Ala Pro Val Leu Gly Gly Phe Ile Gly Gly Ala
145                 150                 155                 160

Ala Gly Tyr Glu Gly Ile Phe Trp Ile Leu Ala Ala Ile Ser Ile Val
                165                 170                 175

Leu Leu Val Thr Asn Ser Ile Thr Phe Pro Lys Asp Ser Pro Thr Glu
            180                 185                 190

Ser Met Gln Gln Ala Lys Gly Asn Val Phe Ala His Tyr Lys Ser Ile
        195                 200                 205

Phe Thr Asn Arg Thr Gly Asn Val Ile Leu Thr Leu Ser Phe Val Leu
    210                 215                 220

Phe Phe Ile Tyr Phe Ala Val Ile Val Tyr Leu Pro Ile Leu Leu Thr
225                 230                 235                 240

Glu His Tyr His Ile Asp Val Gly Ile Ala Gly Leu Leu Tyr Leu Pro
                245                 250                 255

Leu Ala Leu Ser Thr Ile Ala Gly Thr Phe Leu Phe Lys Arg Ile Gln
            260                 265                 270

Ala Lys Ile Gly Leu His Thr Leu Phe Ile Gly Ser Asn Val Ile Ala
        275                 280                 285

Ala Cys Ser Ile Ile Leu Phe Ala Val Thr His Ser Val Ser Leu Val
    290                 295                 300

Leu Met Ala Leu Thr Leu Ala Leu Phe Gly Ile Ser Met Gly Val Ile
305                 310                 315                 320

Pro Pro Leu Tyr Ser Thr Met Ile Thr Asn Glu Phe Glu His Asn Arg
```

-continued

```
            325                 330                 335

Gly Ser Ala Ile Gly Met Phe Asn Phe Ile Arg Tyr Thr Gly Met Ala
            340                 345                 350

Ala Gly Pro Met Val Ser Ala Tyr Leu Leu Thr Met Met Pro Ser Ala
        355                 360                 365

Met Ser Phe Ser Leu Leu Gly Leu Gly Phe Ala Ala Leu Ser Phe Cys
    370                 375                 380

Leu Leu Pro Pro Met Phe Ser Pro Gln Lys Arg Thr Lys Gln Lys Lys
385                 390                 395                 400

His His Met


<210> SEQ ID NO 31
<211> LENGTH: 1566
<212> TYPE: DNA
<213> ORGANISM: Bacillus licheniformis

<400> SEQUENCE: 31

cgcttcttga aaacgaggtg gaattttatt ttgagaaaaa acaagccggt cttgaacagt     60

ttgtaaaaat aaaaaaagaa tgggtaaaag atattttaaa agaccgatat caggatatga    120

aaaagaatcg tcttcaggcc aaacctgatc aggagcctgt tccgcttccg aagcaagcga    180

aaattaatcc cgatgaaaaa gtgattgccc tcacatttga tgacggtccg aatcccgcta    240

caacgaataa aatattaaac gctttacaga agcatgaagg gcatgcgacc ttctttgtgc    300

ttggaagcag agcccaatat tatcccgaaa cgataaaacg gatgctgaag gaaggaaacg    360

aagtcggcaa ccattcctgg gaccatccgt tattgacaag gctgtcaaac gaaaaagcgt    420

atcaggagat taacgacacg caagaaatga tcgaaaaaat cagcggacac ctgcctgtac    480

acttgcgtcc tccatacggc gggatcaatg attccgtccg ctcgctttcc aatctgaagg    540

tttcattgtg ggatgttgat ccggaagatt ggaagtacaa aaataagcaa aagattgtca    600

atcatgtcat gagccatgcg ggagacggaa aaatcgtctt aatgcacgat atttatgcaa    660

cgtccgcaga tgctgctgaa gagattatta aaaagctgaa agcaaaaggc tatcaattgg    720

taactgtatc tcagcttgaa gaagtgaaga agcagagagg ctattgaata aatgagtaga    780

aagcgccata tcggcgcttt tcttttggaa gaaaatatag ggaaaatggt acttgttaaa    840

aattcggaat atttatacaa tatcatatgt ttcacattga aaggggagga gaatcatgaa    900

acaacaaaaa cggctttacg cccgattgct gacgctgtta ggatcccacg taaacggcgg    960

gtcggtttca atttatgttc aaagatagaa gagcaggctg acagtttgaa tcgcataggt   1020

aaggcgggga tgaaatggca acgttatctg atgtagcaaa gaaagcaaat gtgtcgaaaa   1080

tgacggtatc gcgggtgatc aatcatcctg agactgtgac ggatgaattg aaaaagcttg   1140

ttcattccgc aatgaaggag ctcaattata taccgaacta tgcagcaaga gcgctcgttc   1200

aaaacagaac acaggtcgtc aagctgctca tactggaaga aatggataca acagaacctt   1260

attatatgaa tctgttaacg ggaatcagcc gcgagctgga ccgtcatcat tatgctttgc   1320

agcttgtcac aaggaaatct ctcaatatcg gccagtgcga cggcattatt gcgacggggt   1380

tgagaaaagc cgattttgaa gggctcatca aggtttttga aaagcctgtc gttgtattcg   1440

ggcaaaatga aatgggctac gattttattg atgttaacaa tgaaaaagga acctatatgg   1500

caacacgtca cgtcattggt ctgggcgtcc gcaatgtcgt ctttttttggg atcgatttgg   1560

atgagc                                                              1566
```

<210> SEQ ID NO 32
<211> LENGTH: 1631
<212> TYPE: DNA
<213> ORGANISM: Artificial Sequence
<220> FEATURE:
<223> OTHER INFORMATION: synthetic

<400> SEQUENCE: 32
agttcaacaa acgggccata ttgttgtata agtgatgaaa tactgaattt aaaacttagt 60
ttatatgtgg taaaatgttt taatcaagtt taggaggaat taattatgaa gtgtaatgaa 120
tgtaacaggg ttcaattaaa agagggaagc gtatcattaa ccctataaac tacgtctgcc 180
ctcattattg gagggtgaaa tgtgaataca tcctattcac aatcgaattt acgacacaac 240
caaattttaa tttggctttg cattttatct ttttttagcg tattaaatga aatggttttg 300
aacgtctcat tacctgatat tgcaaatgat tttaataaac cacctgcgag tacaaactgg 360
gtgaacacag cctttatgtt aaccttttcc attggaacag ctgtatatgg aaagctatct 420
gatcaattag gcatcaaaag gttactccta tttggaatta taataaattg tttcgggtcg 480
gtaattgggt ttgttggcca ttctttcttt tccttactta ttatggctcg ttttattcaa 540
ggggctggtg cagctgcatt tccagcactc gtaatggttg tagttgcgcg ctatattcca 600
aaggaaaata ggggtaaagc atttggtctt attggatcga tagtagccat gggagaagga 660
gtcggtccag cgattggtgg aatgatagcc cattatattc attggtccta tcttctactc 720
attcctatga taacaattat cactgttccg tttcttatga aattattaaa gaaagaagta 780
aggataaaag gtcattttga tatcaaagga attatactaa tgtctgtagg cattgtattt 840
tttatgttgt ttacaacatc atatagcatt tcttttctta tcgttagcgt gctgtcattc 900
ctgatatttg taaaacatat caggaaagta acagatcctt ttgttgatcc cggattaggg 960
aaaaatatac cttttatgat tggagttctt tgtgggggaa ttatatttgg aacagtagca 1020
gggtttgtct ctatggttcc ttatatgatg aaagatgttc accagctaag tactgccgaa 1080
atcggaagtg taattatttt ccctggaaca atgagtgtca ttattttcgg ctacattggt 1140
gggatacttg ttgatagaag aggtccttta tacgtgttaa acatcggagt tacatttctt 1200
tctgttagct tttaactgc ttcctttctt ttagaaacaa catcatggtt catgacaatt 1260
ataatcgtat ttgttttagg tgggctttcg ttcaccaaaa cagttatatc aacaattgtt 1320
tcaagtagct tgaaacagca ggaagctggt gctggaatga gtttgcttaa ctttaccagc 1380
tttttatcag agggaacagg tattgcaatt gtaggtggtt tattatccat acccttactt 1440
gatcaaaggt tgttacctat ggaagttgat cagtcaactt atctgtatag taatttgtta 1500
ttactttttt caggaatcat tgtcattagt tggctggtta ccttgaatgt atataaacat 1560
tctcaaaggg atttctaaat atgatgaaga aagaccattc caatcaggaa tggtcttttt 1620
ttatgcgcgg c 1631

<210> SEQ ID NO 33
<211> LENGTH: 7249
<212> TYPE: DNA
<213> ORGANISM: Artificial Sequence
<220> FEATURE:
<223> OTHER INFORMATION: synthetic

<400> SEQUENCE: 33
acacggagta ttacaaagac atcagttcgc tttcttttcc ggtattcagc gatttgaagg 60
aagaggatgc caagctggcc aacgatgcgg taaaacttca tttaaaaaat tcctataaag 120

-continued

```
aatttcaaaa aatcgttaat gatgccgaaa agaaggataa ggatgaagaa aacgtttatg    180
aaacgtccta caaagtcaaa tacaacgagg aaggcaaact gagcttttta atctatgact    240
atcagttctc cggcggtgcg cacggcatgt acaccgtaac atcctacaac tttgactttg    300
acaagcataa acaagtcgtg ctgactgacg tattaaacaa tcaggcgaaa atcgaaaagg    360
caaaaaacta tattttcagc tatatcaacg aacatccgga acagttttat tctgatctta    420
aaaagagcga tatccgtttg gatgaacata cggcattcta ttatacaagc agcggaattt    480
caattgtatt tcagcagtat gatatcgccc cgtatgcagc cggaaaccag gaaataaagc    540
ttccgtcgac gcttttatat tagccccggc attagatcta atatttgtaa tagaaacaga    600
gagagcaagt cgtgaaacag gagagtgagc agcgatgtct ggcaaaccat catttcgatg    660
ggttaaaatg ttgatttttt taacgatatt aataggtttg gcagggtact cttacaataa    720
agtgtcaagc aacagccaag agccccctca gccaaaaaaa gaccgcggac aatccggcct    780
cggcgtcgaa tccatggtca atgacagcaa acaagagagg tatgccatcc attatccggt    840
gtttcacata aaagaaatcg atgaacaaat aaaagattat gtgaatcaag aattggccgg    900
ttttaaagag gataacgcaa aggcccaggc tcaggatgaa gacgggcctt ttgaactgaa    960
cattaaatat aaggttgtct attatacaaa ggatacggcc agtgttgtgc tgaatcaata   1020
catagaggcc ggcggcgtat cgggtacaac atctgtcaag acgtttaacg ctgatttaaa   1080
gcagaaaaag ctgctgtccc ttcaagatct gtttgaagag aattcagatt ttctgaacag   1140
gatttcaagc attgcctatc aggaattgaa aaatcggaat ccgtctgctg acatggcttt   1200
attaaaagaa gggacgagcc ctcaggaaga acatttcagc cgctttgcgc ttcttgaaaa   1260
cgaggtggaa ttttattttg agaaaaaaca aaccggtctt gaacagtctg taaaaataaa   1320
aaaagaatgg gtaaaagata ttttaaaaga ccgatatcag gatatgaaaa agaatcgtct   1380
tcaggccaaa cctgatcagg agcctgttcc gcttccgaag caagcgaaaa ttaatcccga   1440
tgaaaaagtg attgccctca catttgatga cggtccgaat cccgctacaa cgaataaaat   1500
attaaacgct ttacagaagc atgaagggca tgcgaccttc tttgtgcttg gaagcagagc   1560
ccaatattat cccgaaacga taaaacggat gctgaaggaa ggaaacgaag tcggcaacca   1620
ttcctgggac catccgttat tgacaaggct gtcaaacgaa aaagcgtatc aggagattaa   1680
cgacacgcaa gaaatgatcg aaaaaatcag cggacacctg cctgtacact tgcgtcctcc   1740
atacggcggg atcaatgatt ccgtccgctc gctttccaat ctgaaggttt cattgtggga   1800
tgttgatccg gaagattgga agtacaaaaa taagcaaaag attgtcaatc atgtcatgag   1860
ccatgcggga gacggaaaaa tcgtcttaat gcacgatatt tatgcaacgt ccgcagatgc   1920
tgctgaagag attattaaaa agctgaaagc aaaaggctat caattggtaa ctgtatctca   1980
gcttgaagaa gtgaagaagc agagaggcta ttgaataaat gagtagaaag cgccatatcg   2040
gctaaatcct tgacgagcaa gggattgacg ctttaaaatg cttgatatgg ctttttatat   2100
gtgttactct acatacagaa attcttcact ttgttggaca aacattcctc agagtgcagt   2160
ttttcttaaa aagccgttta attgtctttc tcttacttgc tctcattttt ttctgagaca   2220
ggtttagaat cagactgaac tgtgaagaaa tgataataaa cgaactgaat gtatcctaat   2280
gcttttatat agggaaaagg tggtgaacta ctttggctca tacaaaatca aaggcagtat   2340
tgatcttata cactgtttgc ttcagtgcat tttttgcatc tttaagccag aacatttatt   2400
cacctattct tccgatcatt aaagaatcat tccatgtttc cacagctatg gtgaacctgt   2460
cagtctcagt ttttatgatt gtgacagcaa taatgcaaat tatattagga gcgatcattg   2520
```

```
attttaaagg cgctcggatc gtcttgatta ccggtattct ggcaacggca gcagccagca   2580
tcggctgtgc ggtgactact gactttacct tgtttctgat attcagaatg atacaggcag   2640
ccggttccgc agcactgcct cttattgctg ccacaacgat cggacagctg tttacaggaa   2700
atgaacgcgg gagtgcaatg ggaacgtatc aaatgctcct gtctgtcgca ccggctattg   2760
ctccagttct aggaggattc ataggcggag cagccggata cgaagggatt ttttggatac   2820
ttgcggccat ctctatcgtt ttgctggtga caaacagcat cacctttcct aaagattctc   2880
caactgaatc tatgcagcaa gccaaaggca atgtgttcgc tcattataaa tcaatattta   2940
caaatcgaac agggaacgtc attttgactt taagttttgt tctctttttc atttattttg   3000
cagtaattgt ctacctccca atattgctga cagagcatta ccatatagat gtgggtatag   3060
caggactgtt atatttgccg ctggcgctga gcacgattgc aggtacgttt ctgtttaaaa   3120
gaatacaggc aaaaatcggg ctgcacacct tgtttatcgg aagcaatgtg attgccgcct   3180
gcagcatcat tttatttgct gttacacatt ccgtttctct cgttctcatg gctctgacgc   3240
tggcactgtt tggcatctcg atgggggtta ttcctccctt gtactctaca atgattacta   3300
atgaatttga gcacaacaga gggagtgcaa tcggaatgtt taactttatc cgatatacag   3360
gcatggcagc aggtccgatg gtatctgcct acttgctcac aatgatgccg tctgccatgt   3420
cctttagcct cctaggcctt ggatttgccg cattgagctt ttgccttctt ccgccaatgt   3480
tttcgccgca gaagcgcacg aaacaaaaaa agcaccacat gtaaaaaagc tgcctttgcg   3540
ggcagctttt ttagttcaac aaacgggcca tattgttgta taagtgatga aatactgaat   3600
ttaaaactta gtttatatgt ggtaaaatgt tttaatcaag tttaggagga attaattatg   3660
aagtgtaatg aatgtaacag ggttcaatta aaagagggaa gcgtatcatt aaccctataa   3720
actacgtctg ccctcattat tggagggtga aatgtgaata catcctattc acaatcgaat   3780
ttacgacaca accaaatttt aatttggctt tgcattttat ctttttttag cgtattaaat   3840
gaaatggttt tgaacgtctc attacctgat attgcaaatg attttaataa accacctgcg   3900
agtacaaact gggtgaacac agcctttatg ttaacctttt ccattggaac agctgtatat   3960
ggaaagctat ctgatcaatt aggcatcaaa aggttactcc tatttggaat tataataaat   4020
tgtttcgggt cggtaattgg gtttgttggc cattctttct tttccttact tattatggct   4080
cgttttattc aaggggctgg tgcagctgca tttccagcac tcgtaatggt tgtagttgcg   4140
cgctatattc caaaggaaaa taggggtaaa gcatttggtc ttattggatc gatagtagcc   4200
atgggagaag gagtcggtcc agcgattggt ggaatgatag cccattatat tcattggtcc   4260
tatcttctac tcattcctat gataacaatt atcactgttc cgtttcttat gaaattatta   4320
aagaaagaag taaggataaa aggtcatttt gatatcaaag gaattatact aatgtctgta   4380
ggcattgtat tttttatgtt gtttacaaca tcatatagca tttcttttct tatcgttagc   4440
gtgctgtcat tcctgatatt tgtaaaacat atcaggaaag taacagatcc ttttgttgat   4500
cccggattag ggaaaaatat accttttatg attggagttc tttgtggggg aattatattt   4560
ggaacagtag cagggtttgt ctctatggtt ccttatatga tgaaagatgt tcaccagcta   4620
agtactgccg aaatcggaag tgtaattatt ttccctggaa caatgagtgt cattatttc    4680
ggctacattg gtgggatact tgttgataga agaggtcctt tatacgtgtt aaacatcgga   4740
gttacatttc tttctgttag ctttttaact gcttcctttc ttttagaaac aacatcatgg   4800
ttcatgacaa ttataatcgt atttgtttta ggtgggcttt cgttcaccaa aacagttata   4860
```

```
tcaacaattg tttcaagtag cttgaaacag caggaagctg gtgctggaat gagtttgctt   4920
aactttacca gctttttatc agagggaaca ggtattgcaa ttgtaggtgg tttattatcc   4980
atacccttac ttgatcaaag gttgttacct atggaagttg atcagtcaac ttatctgtat   5040
agtaatttgt tattactttt ttcaggaatc attgtcatta gttggctggt taccttgaat   5100
gtatataaac attctcaaag ggatttctaa atatgatgaa gaaagaccat tccaatcagg   5160
aatggtcttt ttttatgcgc ggcaaaataa ccaaaagccc gtcttataaa tttctttgat   5220
tacattttat aattaatttt aacaaagtgt catcagccct caggaaggac ttgctgacag   5280
tttgaatcgc ataggtaagg cggggatgaa atggcaacgt tatctgatgt agcaaagaaa   5340
gcaaatgtgt cgaaaatgac ggtatcgcgg gtgatcaatc atcctgagac tgtgacggat   5400
gaattgaaaa agcttgttca ttccgcaatg aaggagctca attatatacc gaactatgca   5460
gcaagagcgc tcgttcaaaa cagaacacag gtcgtcaagc tgctcatact ggaagaaatg   5520
gatacaacag aaccttatta tatgaatctg ttaacgggaa tcagccgcga gctggaccgt   5580
catcattatg ctttgcagct tgtcacaagg aaatctctca atatcggcca gtgcgacggc   5640
attattgcga cggggttgag aaaagccgat tttgaagggc tcatcaaggt ttttgaaaag   5700
cctgtcgttg tattcgggca aatgaaatg ggctacgatt ttattgatgt taacaatgaa   5760
aaaggaacct atatggcaac acgtcacgtc attggtctgg gcgtccgcaa tgtcgtcttt   5820
tttgggatcg atttggatga gccctttgaa cgctcaaggg aaaaaggcta tcttcaggcg   5880
atggaaggca gtctgaaaaa agcagcgatt ttccggatgg aaaacagttc aaaaaaaagt   5940
gaagcacgcg cgcgggaagt gcttgcatcc tttgacgcac ctgcagcggt tgtttgcgct   6000
tcggaccgaa tcgcgctcgg ggttatccgc gcggtgcaat cgcttggtaa aagaattccg   6060
gaagatgtcg cggtcaccgg ctatgacggg gtgtttctcg accggatcgc ttcgcctcgc   6120
ctgacaaccg tcagacagcc tgttgttgaa atgggagagg cttgcgcgag aatcctgctg   6180
aaaaaaatca atgaagacgg agcgccgcaa ggcaatcaat tttttgagcc ggagcttatt   6240
gtccgcgaat cgactttgta gggtgtctca ttctgttacc gttaacaagc tgaaaatgat   6300
tgttcctgtt accgccgtca tgataatttc agaataaaag ccggtttatc acagccggac   6360
aaccaaaagg gggaaacatg atggaatatg cagcgataca tcatcagcct ttcagctctg   6420
atgcctattc ttacaatgga cggacattgc acatcaagat ccgtacaaaa aaggatgatg   6480
ccgaacacgt ccgcttggtt tggggcgatc cttacgaata caccggcggc acatggaaag   6540
cgaacgagct tgcgatggcg aaaattgccg caacaagcac ccatgattac tggtttgccg   6600
aagtggcgcc tccattcagg cgtctgcaat acggatttat cctgacaggc gctgatgatc   6660
gagacacttt ttacggaagc aatggtgcat gtccgtttgc cgggaaagcg gcggatatag   6720
gcaaacactg ttttaaattt ccgtttgttc atgaggcaga cacgtttgat gcacctgact   6780
gggtcaaatc aaccgtctgg tatcaaattt ttccggagcg ctttgccagc gggcgggaag   6840
atttgtctcc ggaaaacgct ttgccatggg gaagcaaaga tcctgaggcg cacgattttt   6900
tcggagggga tttgcagggg atcatggaca agctggacta tttggaagac ttgggggtag   6960
gcggaatcta tttgacgccg atctttgccg cgccttccaa ccataaatac gacacattgg   7020
actattgctc catcgatccg cattttggcg atgaggagct ctttcgcacg ctggtcagcc   7080
ggattcacga gcggggaatg aaaatcatgc ttgatgctgt ttttaaccac attggcagcg   7140
cttcgcaaga gtggcaggat gttgtcaaaa acggtgaaac gtcccgctat aaagactggt   7200
tccatattca ttctttccct gttaaagaag gcagctatga tacatttgc              7249
```

<210> SEQ ID NO 34
<211> LENGTH: 2042
<212> TYPE: DNA
<213> ORGANISM: Bacillus licheniformis

<400> SEQUENCE: 34

```
acacggagta ttacaaagac atcagttcgc tttcttttcc ggtattcagc gatttgaagg     60
aagaggatgc caagctggcc aacgatgcgg taaaacttca tttaaaaaat tcctataaag    120
aatttcaaaa aatcgttaat gatgccgaaa agaaggataa ggatgaagaa aacgtttatg    180
aaacgtccta caaagtcaaa tacaacgagg aaggcaaact gagcttttta atctatgact    240
atcagttctc cggcggtgcg cacggcatgt acaccgtaac atcctacaac tttgactttg    300
acaagcataa acaagtcgtg ctgactgacg tattaaacaa tcaggcgaaa atcgaaaagg    360
caaaaaacta tattttcagc tatatcaacg aacatccgga acagttttat tctgatctta    420
aaaagagcga tatccgtttg gatgaacata cggcattcta ttatacaagc agcggaattt    480
caattgtatt tcagcagtat gatatcgccc cgtatgcagc cggaaaccag gaaataaagc    540
ttccgtcgac gcttttatat tagccccggc attagatcta atatttgtaa tagaaacaga    600
gagagcaagt cgtgaaacag gagagtgagc agcgatgtct ggcaaaccat catttcgatg    660
ggttaaaatg ttgatttttt taacgatatt aataggtttg gcagggtact cttacaataa    720
agtgtcaagc aacagccaag agccccctca gccaaaaaaa gaccgcggac aatccggcct    780
cggcgtcgaa tccatggtca atgacagcaa acaagagagg tatgccatcc attatccggt    840
gtttcacata aaagaaatcg atgaacaaat aaaagattat gtgaatcaag aattggccgg    900
ttttaaagag gataacgcaa aggcccaggc tcaggatgaa gacgggcctt ttgaactgaa    960
cattaaatat aaggttgtct attatacaaa ggatacggcc agtgttgtgc tgaatcaata   1020
catagaggcc ggcggcgtat cgggtacaac atctgtcaag acgtttaacg ctgatttaaa   1080
gcagaaaaag ctgctgtccc ttcaagatct gtttgaagag aattcagatt ttctgaacag   1140
gatttcaagc attgcctatc aggaattgaa aaatcggaat ccgtctgctg acatggcttt   1200
attaaaagaa gggacgagcc ctcaggaaga acatttcagc cgctttgcgc ttcttgaaaa   1260
cgaggtggaa ttttattttg agaaaaaaca aaccggtctt gaacagtctg taaaaataaa   1320
aaaagaatgg gtaaaagata ttttaaaaga ccgatatcag gatatgaaaa agaatcgtct   1380
tcaggccaaa cctgatcagg agcctgttcc gcttccgaag caagcgaaaa ttaatcccga   1440
tgaaaaagtg attgccctca catttgatga cggtccgaat cccgctacaa cgaataaaat   1500
attaaacgct ttacagaagc atgaagggca tgcgaccttc tttgtgcttg gaagcagagc   1560
ccaatattat cccgaaacga taaaacggat gctgaaggaa ggaaacgaag tcggcaacca   1620
ttcctgggac catccgttat tgacaaggct gtcaaacgaa aaagcgtatc aggagattaa   1680
cgacacgcaa gaaatgatcg aaaaaatcag cggacacctg cctgtacact tgcgtcctcc   1740
atacggcggg atcaatgatt ccgtccgctc gctttccaat ctgaaggttt cattgtggga   1800
tgttgatccg gaagattgga agtacaaaaa taagcaaaag attgtcaatc atgtcatgag   1860
ccatgcggga gacggaaaaa tcgtcttaat gcacgatatt tatgcaacgt ccgcagatgc   1920
tgctgaagag attattaaaa agctgaaagc aaaaggctat caattggtaa ctgtatctca   1980
gcttgaagaa gtgaagaagc agagaggcta ttgaataaat gagtagaaag cgccatatcg   2040
gc                                                                  2042
```

<210> SEQ ID NO 35
<211> LENGTH: 257
<212> TYPE: DNA
<213> ORGANISM: Bacillus subtilis

<400> SEQUENCE: 35

```
ctaaatcctt gacgagcaag ggattgacgc tttaaaatgc ttgatatggc tttttatatg      60
tgttactcta catacagaaa ttcttcactt tgttggacaa acattcctca gagtgcagtt     120
tttcttaaaa agccgtttaa ttgtctttct cttacttgct ctcatttttt tctgagacag     180
gtttagaatc agactgaact gtgaagaaat gataataaac gaactgaatg tatcctaatg     240
cttttatata gggaaaa                                                    257
```

<210> SEQ ID NO 36
<211> LENGTH: 14
<212> TYPE: DNA
<213> ORGANISM: Bacillus subtilis

<400> SEQUENCE: 36

```
ggtggtgaac tact                                                        14
```

<210> SEQ ID NO 37
<211> LENGTH: 1212
<212> TYPE: DNA
<213> ORGANISM: Bacillus subtilis

<400> SEQUENCE: 37

```
ttggctcata caaaatcaaa ggcagtattg atcttataca ctgtttgctt cagtgcattt      60
tttgcatctt taagccagaa catttattca cctattcttc cgatcattaa agaatcattc     120
catgtttcca cagctatggt gaacctgtca gtctcagttt ttatgattgt gacagcaata     180
atgcaaatta tattaggagc gatcattgat tttaaaggcg ctcggatcgt cttgattacc     240
ggtattctgg caacggcagc agccagcatc ggctgtgcgg tgactactga ctttaccttg     300
tttctgatat tcagaatgat acaggcagcc ggttccgcag cactgcctct tattgctgcc     360
acaacgatcg gacagctgtt tacaggaaat gaacgcggga gtgcaatggg aacgtatcaa     420
atgctcctgt ctgtcgcacc ggctattgct ccagttctag gaggattcat aggcggagca     480
gccggatacg aagggatttt ttggatactt gcggccatct ctatcgtttt gctggtgaca     540
aacagcatca cctttcctaa agattctcca actgaatcta tgcagcaagc caaaggcaat     600
gtgttcgctc attataaatc aatatttaca aatcgaacag ggaacgtcat tttgacttta     660
agttttgttc tctttttcat ttattttgca gtaattgtct acctcccaat attgctgaca     720
gagcattacc atatagatgt gggtatagca ggactgttat atttgccgct ggcgctgagc     780
acgattgcag gtacgtttct gtttaaaaga atacaggcaa aaatcgggct gcacaccttg     840
tttatcggaa gcaatgtgat tgccgcctgc agcatcattt tatttgctgt tacacattcc     900
gtttctctcg ttctcatggc tctgacgctg gcactgtttg gcatctcgat gggggttatt     960
cctcccttgt actctacaat gattactaat gaatttgagc acaacagagg gagtgcaatc    1020
ggaatgttta actttatccg atatacaggc atggcagcag gtccgatggt atctgcctac    1080
ttgctcacaa tgatgccgtc tgccatgtcc tttagcctcc taggccttgg atttgccgca    1140
ttgagctttt gccttcttcc gccaatgttt tcgccgcaga agcgcacgaa acaaaaaaag    1200
caccacatgt aa                                                        1212
```

<210> SEQ ID NO 38
<211> LENGTH: 48
<212> TYPE: DNA
<213> ORGANISM: Bacillus subtilis

<400> SEQUENCE: 38

```
atatgatgaa gaaagaccat tccaatcagg aatggtcttt ttttatgc                48
```

<210> SEQ ID NO 39
<211> LENGTH: 2053
<212> TYPE: DNA
<213> ORGANISM: Bacillus licheniformis

<400> SEQUENCE: 39

```
gcccgtctta taaatttctt tgattacatt ttataattaa ttttaacaaa gtgtcatcag     60
ccctcaggaa ggacttgctg acagtttgaa tcgcataggt aaggcgggga tgaaatggca    120
acgttatctg atgtagcaaa gaaagcaaat gtgtcgaaaa tgacggtatc gcgggtgatc    180
aatcatcctg agactgtgac ggatgaattg aaaaagcttg ttcattccgc aatgaaggag    240
ctcaattata taccgaacta tgcagcaaga gcgctcgttc aaaacagaac acaggtcgtc    300
aagctgctca tactggaaga aatggataca acagaacctt attatatgaa tctgttaacg    360
ggaatcagcc gcgagctgga ccgtcatcat tatgctttgc agcttgtcac aaggaaatct    420
ctcaatatcg gccagtgcga cggcattatt gcgacggggt tgagaaaagc cgattttgaa    480
gggctcatca aggtttttga aaagcctgtc gttgtattcg ggcaaaatga aatgggctac    540
gattttattg atgttaacaa tgaaaaagga acctatatgg caacacgtca cgtcattggt    600
ctgggcgtcc gcaatgtcgt ctttttttggg atcgatttgg atgagccctt tgaacgctca    660
agggaaaaag gctatcttca ggcgatggaa ggcagtctga aaaaagcagc gatttccgg     720
atggaaaaca gttcaaaaaa aagtgaagca cgcgcgcggg aagtgcttgc atcctttgac    780
gcacctgcag cggttgtttg cgcttcggac cgaatcgcgc tcggggttat ccgcgcggtg    840
caatcgcttg gtaaaagaat tccggaagat gtcgcggtca ccggctatga cggggtgttt    900
ctcgaccgga tcgcttcgcc tcgcctgaca accgtcagac agcctgttgt tgaaatggga    960
gaggcttgcg cgagaatcct gctgaaaaaa atcaatgaag acggagcgcc gcaaggcaat   1020
caattttttg agccggagct tattgtccgc gaatcgactt tgtagggtgt ctcattctgt   1080
taccgttaac aagctgaaaa tgattgttcc tgttaccgcc gtcatgataa tttcagaata   1140
aaagccggtt tatcacagcc ggacaaccaa aagggggaaa catgatggaa tatgcagcga   1200
tacatcatca gcctttcagc tctgatgcct attcttacaa tggacggaca ttgcacatca   1260
agatccgtac aaaaaaggat gatgccgaac acgtccgctt ggtttggggc gatccttacg   1320
aatacaccgg cggcacatgg aaagcgaacg agcttgcgat ggcgaaaatt gccgcaacaa   1380
gcacccatga ttactggttt gccgaagtgg cgcctccatt caggcgtctg caatacggat   1440
ttatcctgac aggcgctgat gatcgagaca ctttttacgg aagcaatggt gcatgtccgt   1500
ttgccgggaa agcggcggat ataggcaaac actgttttaa atttccgttt gttcatgagg   1560
cagacacgtt tgatgcacct gactgggtca aatcaaccgt ctggtatcaa atttttccgg   1620
agcgctttgc cagcgggcgg gaagatttgt ctccggaaaa cgctttgcca tggggaagca   1680
aagatcctga ggcgcacgat tttttcggag gggatttgca ggggatcatg gacaagctgg   1740
actatttgga agacttgggg gtaggcggaa tctatttgac gccgatcttt gccgcgcctt   1800
ccaaccataa atacgacaca ttggactatt gctccatcga tccgcatttt ggcgatgagg   1860
```

```
agctctttcg cacgctggtc agccggattc acgagcgggg aatgaaaatc atgcttgatg   1920

ctgtttttaa ccacattggc agcgcttcgc aagagtggca ggatgttgtc aaaaacggtg   1980

aaacgtcccg ctataaagac tggttccata ttcattcttt ccctgttaaa gaaggcagct   2040

atgatacatt tgc                                                       2053
```

```
<210> SEQ ID NO 40
<211> LENGTH: 7172
<212> TYPE: DNA
<213> ORGANISM: Artificial Sequence
<220> FEATURE:
<223> OTHER INFORMATION: synthetic

<400> SEQUENCE: 40

acacggagta ttacaaagac atcagttcgc tttcttttcc ggtattcagc gatttgaagg     60

aagaggatgc caagctggcc aacgatgcgg taaaacttca tttaaaaaat tcctataaag    120

aatttcaaaa aatcgttaat gatgccgaaa agaaggataa ggatgaagaa aacgtttatg    180

aaacgtccta caaagtcaaa tacaacgagg aaggcaaact gagcttttta atctatgact    240

atcagttctc cggcggtgcg cacggcatgt acaccgtaac atcctacaac tttgactttg    300

acaagcataa acaagtcgtg ctgactgacg tattaaacaa tcaggcgaaa atcgaaaagg    360

caaaaaacta tattttcagc tatatcaacg aacatccgga acagttttat tctgatctta    420

aaaagagcga tatccgtttg gatgaacata cggcattcta ttatacaagc agcggaattt    480

caattgtatt tcagcagtat gatatcgccc cgtatgcagc cggaaaccag gaaataaagc    540

ttccgtcgac gcttttatat tagccccggc attagatcta atatttgtaa tagaaacaga    600

gagagcaagt cgtgaaacag gagagtgagc agcgatgtct ggcaaaccat catttcgatg    660

ggttaaaatg ttgatttttt taacgatatt aataggtttg gcagggtact cttacaataa    720

agtgtcaagc aacagccaag agccccctca gccaaaaaaa gaccgcggac aatccggcct    780

cggcgtcgaa tccatggtca atgacagcaa acaagagagg tatgccatcc attatccggt    840

gtttcacata aaagaaatcg atgaacaaat aaaagattat gtgaatcaag aattggccgg    900

ttttaaagag gataacgcaa aggcccaggc tcaggatgaa gacgggcctt ttgaactgaa    960

cattaaatat aaggttgtct attatacaaa ggatacggcc agtgttgtgc tgaatcaata   1020

catagaggcc ggcggcgtat cgggtacaac atctgtcaag acgtttaacg ctgatttaaa   1080

gcagaaaaag ctgctgtccc ttcaagatct gtttgaagag aattcagatt ttctgaacag   1140

gatttcaagc attgcctatc aggaattgaa aaatcggaat ccgtctgctg acatggcttt   1200

attaaaagaa gggacgagcc ctcaggaaga acatttcagc cgctttgcgc ttcttgaaaa   1260

cgaggtggaa ttttattttg agaaaaaaca aaccggtctt gaacagtctg taaaaataaa   1320

aaaagaatgg gtaaaagata ttttaaaaga ccgatatcag gatatgaaaa agaatcgtct   1380

tcaggccaaa cctgatcagg agcctgttcc gcttccgaag caagcgaaaa ttaatcccga   1440

tgaaaaagtg attgccctca catttgatga cggtccgaat cccgctacaa cgaataaaat   1500

attaaacgct ttacagaagc atgaagggca tgcgaccttc tttgtgcttg gaagcagagc   1560

ccaatattat cccgaaacga taaaacggat gctgaaggaa ggaaacgaag tcggcaacca   1620

ttcctgggac catccgttat tgacaaggct gtcaaacgaa aaagcgtatc aggagattaa   1680

cgacacgcaa gaaatgatcg aaaaaatcag cggacacctg cctgtacact tgcgtcctcc   1740

atacggcggg atcaatgatt ccgtccgctc gctttccaat ctgaaggttt cattgtggga   1800

tgttgatccg gaagattgga agtacaaaaa taagcaaaag attgtcaatc atgtcatgag   1860
```

ccatgcggga gacggaaaaa tcgtcttaat gcacgatatt tatgcaacgt ccgcagatgc 1920
tgctgaagag attattaaaa agctgaaagc aaaaggctat caattggtaa ctgtatctca 1980
gcttgaagaa gtgaagaagc agagaggcta ttgaataaat gagtagaaag cgccatatcg 2040
gctaagaaaa gtgattctgg gagagccggg atcacttttt tatttacctt atgcccgaaa 2100
tgaaagcttt atgacctaat tgtgtaacta tatcctattt tttcaaaaaa tattttaaaa 2160
acgagcagga tttcagaaaa aatcgtggaa ttgatacact aatgctttta tatagggaaa 2220
aggtggtgaa ctactttggc tcatacaaaa tcaaaggcag tattgatctt atacactgtt 2280
tgcttcagtg catttttttgc atctttaagc cagaacattt attcacctat tcttccgatc 2340
attaaagaat cattccatgt ttccacagct atggtgaacc tgtcagtctc agtttttatg 2400
attgtgacag caataatgca aattatatta ggagcgatca ttgattttaa aggcgctcgg 2460
atcgtcttga ttaccggtat tctggcaacg gcagcagcca gcatcggctg tgcggtgact 2520
actgacttta ccttgtttct gatattcaga atgatacagg cagccggttc cgcagcactg 2580
cctcttattg ctgccacaac gatcggacag ctgtttacag gaaatgaacg cgggagtgca 2640
atgggaacgt atcaaatgct cctgtctgtc gcaccggcta ttgctccagt tctaggagga 2700
ttcataggcg gagcagccgg atacgaaggg attttttgga tacttgcggc catctctatc 2760
gttttgctgg tgacaaacag catcaccttt cctaaagatt ctccaactga atctatgcag 2820
caagccaaag gcaatgtgtt cgctcattat aaatcaatat ttacaaatcg aacagggaac 2880
gtcattttga ctttaagttt tgttctcttt ttcatttatt ttgcagtaat tgtctacctc 2940
ccaatattgc tgacagagca ttaccatata gatgtgggta tagcaggact gttatatttg 3000
ccgctggcgc tgagcacgat tgcaggtacg tttctgttta aaagaataca ggcaaaaatc 3060
gggctgcaca ccttgtttat cggaagcaat gtgattgccg cctgcagcat cattttattt 3120
gctgttacac attccgtttc tctcgttctc atggctctga cgctggcact gtttggcatc 3180
tcgatggggg ttattcctcc cttgtactct acaatgatta ctaatgaatt tgagcacaac 3240
agagggagtg caatcggaat gtttaacttt atccgatata caggcatggc agcaggtccg 3300
atggtatctg cctacttgct cacaatgatg ccgtctgcca tgtcctttag cctcctaggc 3360
cttggatttg ccgcattgag cttttgcctt cttccgccaa tgttttcgcc gcagaagcgc 3420
acgaaacaaa aaaagcacca catgtaaaaa agctgccttt gcgggcagct tttttagttc 3480
aacaaacggg ccatattgtt gtataagtga tgaaatactg aatttaaaac ttagtttata 3540
tgtggtaaaa tgttttaatc aagtttagga ggaattaatt atgaagtgta atgaatgtaa 3600
cagggttcaa ttaaaagagg gaagcgtatc attaacccta taaactacgt ctgccctcat 3660
tattggaggg tgaaatgtga atacatccta ttcacaatcg aatttacgac acaaccaaat 3720
tttaatttgg ctttgcattt tatctttttt tagcgtatta aatgaaatgg ttttgaacgt 3780
ctcattacct gatattgcaa atgattttaa taaaccacct gcgagtacaa actgggtgaa 3840
cacagccttt atgttaacct tttccattgg aacagctgta tatggaaagc tatctgatca 3900
attaggcatc aaaaggttac tcctatttgg aattataata aattgtttcg ggtcggtaat 3960
tgggtttgtt ggccattctt tcttttcctt acttattatg gctcgtttta ttcaaggggc 4020
tggtgcagct gcatttccag cactcgtaat ggttgtagtt gcgcgctata ttccaaagga 4080
aaataggggt aaagcatttg gtcttattgg atcgatagta gccatgggag aaggagtcgg 4140
tccagcgatt ggtggaatga tagcccatta tattcattgg tcctatcttc tactcattcc 4200

-continued

```
tatgataaca attatcactg ttccgtttct tatgaaatta ttaaagaaag aagtaaggat   4260

aaaaggtcat tttgatatca aaggaattat actaatgtct gtaggcattg tatttttat    4320

gttgtttaca acatcatata gcatttcttt tcttatcgtt agcgtgctgt cattcctgat   4380

atttgtaaaa catatcagga aagtaacaga tccttttgtt gatcccggat tagggaaaaa   4440

tatacctttt atgattggag ttctttgtgg gggaattata tttggaacag tagcagggtt   4500

tgtctctatg gttccttata tgatgaaaga tgttcaccag ctaagtactg ccgaaatcgg   4560

aagtgtaatt attttccctg gaacaatgag tgtcattatt ttcggctaca ttggtgggat   4620

acttgttgat agaagaggtc ctttatacgt gttaaacatc ggagttacat ttctttctgt   4680

tagcttttta actgcttcct ttcttttaga aacaacatca tggttcatga caattataat   4740

cgtatttgtt ttaggtgggc tttcgttcac caaaacagtt atatcaacaa ttgtttcaag   4800

tagcttgaaa cagcaggaag ctggtgctgg aatgagtttg cttaacttta ccagcttttt   4860

atcagaggga acaggtattg caattgtagg tggtttatta tccataccct tacttgatca   4920

aaggttgtta cctatggaag ttgatcagtc aacttatctg tatagtaatt tgttattact   4980

tttttcagga atcattgtca ttagttggct ggttaccttg aatgtatata aacattctca   5040

aagggatttc taaatatgat gaagaaagac cattccaatc aggaatggtc ttttttttatg  5100

cgcggcaaaa taaccaaaag cccgtcttat aaatttcttt gattacattt tataattaat   5160

tttaacaaag tgtcatcagc cctcaggaag gacttgctga cagtttgaat cgcataggta   5220

aggcggggat gaaatggcaa cgttatctga tgtagcaaag aaagcaaatg tgtcgaaaat   5280

gacggtatcg cgggtgatca atcatcctga gactgtgacg gatgaattga aaaagcttgt   5340

tcattccgca atgaaggagc tcaattatat accgaactat gcagcaagag cgctcgttca   5400

aaacagaaca caggtcgtca agctgctcat actggaagaa atggatacaa cagaacctta   5460

ttatatgaat ctgttaacgg gaatcagccg cgagctggac cgtcatcatt atgctttgca   5520

gcttgtcaca aggaaatctc tcaatatcgg ccagtgcgac ggcattattg cgacggggtt   5580

gagaaaagcc gattttgaag ggctcatcaa ggtttttgaa aagcctgtcg ttgtattcgg   5640

gcaaaatgaa atgggctacg attttattga tgttaacaat gaaaaaggaa cctatatggc   5700

aacacgtcac gtcattggtc tgggcgtccg caatgtcgtc ttttttggga tcgatttgga   5760

tgagcccttt gaacgctcaa gggaaaaagg ctatcttcag gcgatggaag gcagtctgaa   5820

aaaagcagcg attttccgga tggaaaacag ttcaaaaaaa agtgaagcac gcgcgcggga   5880

agtgcttgca tcctttgacg cacctgcagc ggttgtttgc gcttcggacc gaatcgcgct   5940

cggggttatc cgcgcggtgc aatcgcttgg taaaagaatt ccggaagatg tcgcggtcac   6000

cggctatgac ggggtgtttc tcgaccggat cgcttcgcct cgcctgacaa ccgtcagaca   6060

gcctgttgtt gaaatgggag aggcttgcgc gagaatcctg ctgaaaaaaa tcaatgaaga   6120

cggagcgccg caaggcaatc aatttttga gccggagctt attgtccgcg aatcgacttt    6180

gtagggtgtc tcattctgtt accgttaaca agctgaaaat gattgttcct gttaccgccg   6240

tcatgataat ttcagaataa aagccggttt atcacagccg gacaaccaaa agggggaaac   6300

atgatggaat atgcagcgat acatcatcag cctttcagct ctgatgccta ttcttacaat   6360

ggacggacat tgcacatcaa gatccgtaca aaaaaggatg atgccgaaca cgtccgcttg   6420

gtttggggcg atccttacga atacaccggc ggcacatgga aagcgaacga gcttgcgatg   6480

gcgaaaattg ccgcaacaag cacccatgat tactggtttg ccgaagtggc gcctccattc   6540

aggcgtctgc aatacggatt tatcctgaca ggcgctgatg atcgagacac tttttacgga   6600
```

agcaatggtg catgtccgtt tgccgggaaa gcggcggata taggcaaaca ctgttttaaa 6660
tttccgtttg ttcatgaggc agacacgttt gatgcacctg actgggtcaa atcaaccgtc 6720
tggtatcaaa tttttccgga gcgctttgcc agcgggcggg aagatttgtc tccggaaaac 6780
gctttgccat ggggaagcaa agatcctgag gcgcacgatt ttttcggagg ggatttgcag 6840
gggatcatgg acaagctgga ctatttggaa gacttggggg taggcggaat ctatttgacg 6900
ccgatctttg ccgcgccttc caaccataaa tacgacacat tggactattg ctccatcgat 6960
ccgcattttg gcgatgagga gctctttcgc acgctggtca gccggattca cgagcgggga 7020
atgaaaatca tgcttgatgc tgtttttaac cacattggca gcgcttcgca agagtggcag 7080
gatgttgtca aaaacggtga aacgtcccgc tataaagact ggttccatat tcattctttc 7140
cctgttaaag aaggcagcta tgatacattt gc 7172

<210> SEQ ID NO 41
<211> LENGTH: 193
<212> TYPE: DNA
<213> ORGANISM: Bacillus subtilis

<400> SEQUENCE: 41
taagaaaagt gattctggga gagccgggat cactttttta tttaccttat gcccgaaatg 60
aaagctttat gacctaattg tgtaactata tcctattttt tcaaaaaata ttttaaaaac 120
gagcaggatt tcagaaaaaa tcgtggaatt gatacactaa tgcttttata tagggaaaag 180
gtggtgaact act 193

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
cgcttcttga aaacgaggtg 20

<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
gctcatccaa atcgatccca 20

<210> SEQ ID NO 44
<211> LENGTH: 4595
<212> TYPE: DNA
<213> ORGANISM: Artificial Sequence
<220> FEATURE:
<223> OTHER INFORMATION: pcr product

<400> SEQUENCE: 44
cgcttcttga aaacgaggtg gaattttatt ttgagaaaaa acaaaccggt cttgaacagt 60
ctgtaaaaat aaaaaaagaa tgggtaaaag atattttaaa agaccgatat caggatatga 120
aaaagaatcg tcttcaggcc aaacctgatc aggagcctgt tccgcttccg aagcaagcga 180
aaattaatcc cgatgaaaaa gtgattgccc tcacatttga tgacggtccg aatcccgcta 240

```
caacgaataa aatattaaac gctttacaga agcatgaagg gcatgcgacc ttctttgtgc    300
ttggaagcag agcccaatat tatcccgaaa cgataaaacg gatgctgaag gaaggaaacg    360
aagtcggcaa ccattcctgg gaccatccgt tattgacaag gctgtcaaac gaaaaagcgt    420
atcaggagat taacgacacg caagaaatga tcgaaaaaat cagcggacac ctgcctgtac    480
acttgcgtcc tccatacggc gggatcaatg attccgtccg ctcgctttcc aatctgaagg    540
tttcattgtg ggatgttgat ccggaagatt ggaagtacaa aaataagcaa aagattgtca    600
atcatgtcat gagccatgcg ggagacggaa aaatcgtctt aatgcacgat atttatgcaa    660
cgtccgcaga tgctgctgaa gagattatta aaaagctgaa agcaaaaggc tatcaattgg    720
taactgtatc tcagcttgaa gaagtgaaga agcagagagg ctattgaata aatgagtaga    780
aagcgccata tcggctaaat ccttgacgag caagggattg acgctttaaa atgcttgata    840
tggcttttta tatgtgttac tctacataca gaaattcttc actttgttgg acaaacattc    900
ctcagagtgc agtttttctt aaaaagccgt ttaattgtct ttctcttact tgctctcatt    960
tttttctgag acaggtttag aatcagactg aactgtgaag aaatgataat aaacgaactg   1020
aatgtatcct aatgctttta tatagggaaa aggtggtgaa ctactttggc tcatacaaaa   1080
tcaaaggcag tattgatctt atacactgtt tgcttcagtg catttttttgc atctttaagc   1140
cagaacattt attcacctat tcttccgatc attaaagaat cattccatgt ttccacagct   1200
atggtgaacc tgtcagtctc agtttttatg attgtgacag caataatgca aattatatta   1260
ggagcgatca ttgattttaa aggcgctcgg atcgtcttga ttaccggtat tctggcaacg   1320
gcagcagcca gcatcggctg tgcggtgact actgacttta ccttgtttct gatattcaga   1380
atgatacagg cagccggttc cgcagcactg cctcttattg ctgccacaac gatcggacag   1440
ctgtttacag gaaatgaacg cgggagtgca atgggaacgt atcaaatgct cctgtctgtc   1500
gcaccggcta ttgctccagt tctaggagga ttcataggcg gagcagccgg atacgaaggg   1560
attttttgga tacttgcggc catctctatc gttttgctgg tgacaaacag catcaccttt   1620
cctaaagatt ctccaactga atctatgcag caagccaaag gcaatgtgtt cgctcattat   1680
aaatcaatat ttacaaatcg aacagggaac gtcattttga ctttaagttt tgttctcttt   1740
ttcatttatt ttgcagtaat tgtctacctc ccaatattgc tgacagagca ttaccatata   1800
gatgtgggta tagcaggact gttatatttg ccgctggcgc tgagcacgat tgcaggtacg   1860
tttctgttta aaagaataca ggcaaaaatc gggctgcaca ccttgtttat cggaagcaat   1920
gtgattgccg cctgcagcat cattttattt gctgttacac attccgtttc tctcgttctc   1980
atggctctga cgctggcact gtttggcatc tcgatggggg ttattcctcc cttgtactct   2040
acaatgatta ctaatgaatt tgagcacaac agagggagtg caatcggaat gtttaacttt   2100
atccgatata caggcatggc agcaggtccg atggtatctg cctacttgct cacaatgatg   2160
ccgtctgcca tgtcctttag cctcctaggc cttggatttg ccgcattgag cttttgcctt   2220
cttccgccaa tgttttcgcc gcagaagcgc acgaaacaaa aaaagcacca catgtaaaaa   2280
agctgccttt gcgggcagct tttttagttc aacaaacggg ccatattgtt gtataagtga   2340
tgaaatactg aatttaaaac ttagtttata tgtggtaaaa tgttttaatc aagtttagga   2400
ggaattaatt atgaagtgta atgaatgtaa cagggttcaa ttaaaagagg gaagcgtatc   2460
attaacccta taaactacgt ctgccctcat tattggaggg tgaaatgtga atacatccta   2520
ttcacaatcg aatttacgac acaaccaaat tttaatttgg ctttgcattt tatctttttt   2580
tagcgtatta aatgaaatgg ttttgaacgt ctcattacct gatattgcaa atgattttaa   2640
```

```
taaaccacct gcgagtacaa actgggtgaa cacagccttt atgttaacct tttccattgg   2700
aacagctgta tatggaaagc tatctgatca attaggcatc aaaaggttac tcctatttgg   2760
aattataata aattgtttcg ggtcggtaat tgggtttgtt ggccattctt tcttttcctt   2820
acttattatg gctcgtttta ttcaaggggc tggtgcagct gcatttccag cactcgtaat   2880
ggttgtagtt gcgcgctata ttccaaagga aaataggggt aaagcatttg gtcttattgg   2940
atcgatagta gccatgggag aaggagtcgg tccagcgatt ggtggaatga tagcccatta   3000
tattcattgg tcctatcttc tactcattcc tatgataaca attatcactg ttccgtttct   3060
tatgaaatta ttaaagaaag aagtaaggat aaaaggtcat tttgatatca aaggaattat   3120
actaatgtct gtaggcattg tatttttat gttgtttaca acatcatata gcatttcttt   3180
tcttatcgtt agcgtgctgt cattcctgat atttgtaaaa catatcagga aagtaacaga   3240
tccttttgtt gatcccggat tagggaaaaa tataccttt atgattggag ttctttgtgg   3300
gggaattata tttggaacag tagcagggtt tgtctctatg gttccttata tgatgaaaga   3360
tgttcaccag ctaagtactg ccgaaatcgg aagtgtaatt attttccctg gaacaatgag   3420
tgtcattatt ttcggctaca ttggtgggat acttgttgat agaagaggtc ctttatacgt   3480
gttaaacatc ggagttacat ttctttctgt tagcttttta actgcttcct ttcttttaga   3540
aacaacatca tggttcatga caattataat cgtatttgtt ttaggtgggc tttcgttcac   3600
caaaacagtt atatcaacaa ttgtttcaag tagcttgaaa cagcaggaag ctggtgctgg   3660
aatgagtttg cttaacttta ccagcttttt atcagaggga acaggtattg caattgtagg   3720
tggtttatta tccataccct tacttgatca aaggttgtta cctatggaag ttgatcagtc   3780
aacttatctg tatagtaatt tgttattact tttttcagga atcattgtca ttagttggct   3840
ggttaccttg aatgtatata aacattctca aagggatttc taaatatgat gaagaaagac   3900
cattccaatc aggaatggtc tttttttatg cgcggcaaaa taaccaaaag cccgtcttat   3960
aaatttcttt gattacattt tataattaat tttaacaaag tgtcatcagc cctcaggaag   4020
gacttgctga cagtttgaat cgcataggta aggcggggat gaaatggcaa cgttatctga   4080
tgtagcaaag aaagcaaatg tgtcgaaaat gacggtatcg cgggtgatca atcatcctga   4140
gactgtgacg gatgaattga aaaagcttgt tcattccgca atgaaggagc tcaattatat   4200
accgaactat gcagcaagag cgctcgttca aaacagaaca caggtcgtca agctgctcat   4260
actggaagaa atggatacaa cagaacctta ttatatgaat ctgttaacgg gaatcagccg   4320
cgagctggac cgtcatcatt atgctttgca gcttgtcaca aggaaatctc tcaatatcgg   4380
ccagtgcgac ggcattattg cgacggggtt gagaaaagcc gattttgaag ggctcatcaa   4440
ggtttttgaa aagcctgtcg ttgtattcgg gcaaaatgaa atgggctacg attttattga   4500
tgttaacaat gaaaaaggaa cctatatggc aacacgtcac gtcattggtc tgggcgtccg   4560
caatgtcgtc ttttttggga tcgatttgga tgagc                              4595
```

<210> SEQ ID NO 45
<211> LENGTH: 4518
<212> TYPE: DNA
<213> ORGANISM: Artificial Sequence
<220> FEATURE:
<223> OTHER INFORMATION: pcr product

<400> SEQUENCE: 45

```
cgcttcttga aaacgaggtg gaattttatt ttgagaaaaa acaaaccggt cttgaacagt     60
```

-continued ctgtaaaaat aaaaaaagaa tgggtaaaag atattttaaa agaccgatat caggatatga 120
aaaagaatcg tcttcaggcc aaacctgatc aggagcctgt tccgcttccg aagcaagcga 180
aaattaatcc cgatgaaaaa gtgattgccc tcacatttga tgacggtccg aatcccgcta 240
caacgaataa aatattaaac gctttacaga agcatgaagg gcatgcgacc ttctttgtgc 300
ttggaagcag agcccaatat tatcccgaaa cgataaaacg gatgctgaag gaaggaaacg 360
aagtcggcaa ccattcctgg gaccatccgt tattgacaag gctgtcaaac gaaaaagcgt 420
atcaggagat taacgacacg caagaaatga tcgaaaaaat cagcggacac ctgcctgtac 480
acttgcgtcc tccatacggc gggatcaatg attccgtccg ctcgctttcc aatctgaagg 540
tttcattgtg ggatgttgat ccggaagatt ggaagtacaa aaataagcaa aagattgtca 600
atcatgtcat gagccatgcg ggagacggaa aaatcgtctt aatgcacgat atttatgcaa 660
cgtccgcaga tgctgctgaa gagattatta aaaagctgaa agcaaaaggc tatcaattgg 720
taactgtatc tcagcttgaa gaagtgaaga agcagagagg ctattgaata aatgagtaga 780
aagcgccata tcggctaaga aaagtgattc tgggagagcc gggatcactt ttttatttac 840
cttatgcccg aaatgaaagc tttatgacct aattgtgtaa ctatatccta tttttcaaa 900 aaatatttta aaaacgagca ggatttcaga aaaaatcgtg gaattgatac actaatgctt 960
ttatataggg aaaaggtggt gaactacttt ggctcataca aaatcaaagg cagtattgat 1020
cttatacact gtttgcttca gtgcattttt tgcatcttta agccagaaca tttattcacc 1080
tattcttccg atcattaaag aatcattcca tgtttccaca gctatggtga acctgtcagt 1140
ctcagttttt atgattgtga cagcaataat gcaaattata ttaggagcga tcattgattt 1200
taaaggcgct cggatcgtct tgattaccgg tattctggca acggcagcag ccagcatcgg 1260
ctgtgcggtg actactgact ttaccttgtt tctgatattc agaatgatac aggcagccgg 1320
ttccgcagca ctgcctctta ttgctgccac aacgatcgga cagctgttta caggaaatga 1380
acgcgggagt gcaatgggaa cgtatcaaat gctcctgtct gtcgcaccgg ctattgctcc 1440
agttctagga ggattcatag gcggagcagc cggatacgaa gggatttttt ggatacttgc 1500
ggccatctct atcgttttgc tggtgacaaa cagcatcacc tttcctaaag attctccaac 1560
tgaatctatg cagcaagcca aaggcaatgt gttcgctcat tataaatcaa tatttacaaa 1620
tcgaacaggg aacgtcattt tgactttaag ttttgttctc tttttcattt attttgcagt 1680
aattgtctac ctcccaatat tgctgacaga gcattaccat atagatgtgg gtatagcagg 1740
actgttatat ttgccgctgg cgctgagcac gattgcaggt acgtttctgt ttaaaagaat 1800
acaggcaaaa atcgggctgc acaccttgtt tatcggaagc aatgtgattg ccgcctgcag 1860
catcatttta tttgctgtta cacattccgt ttctctcgtt ctcatggctc tgacgctggc 1920
actgtttggc atctcgatgg gggttattcc tcccttgtac tctacaatga ttactaatga 1980
atttgagcac aacagaggga gtgcaatcgg aatgtttaac tttatccgat atacaggcat 2040
ggcagcaggt ccgatggtat ctgcctactt gctcacaatg atgccgtctg ccatgtcctt 2100
tagcctccta ggccttggat ttgccgcatt gagcttttgc cttcttccgc caatgttttc 2160
gccgcagaag cgcacgaaac aaaaaaagca ccacatgtaa aaaagctgcc tttgcgggca 2220 gctttttag ttcaacaaac gggccatatt gttgtataag tgatgaaata ctgaatttaa 2280
aacttagttt atatgtggta aaatgtttta atcaagttta ggaggaatta attatgaagt 2340
gtaatgaatg taacagggtt caattaaaag agggaagcgt atcattaacc ctataaacta 2400
cgtctgccct cattattgga gggtgaaatg tgaatacatc ctattcacaa tcgaatttac 2460

```
gacacaacca aattttaatt tggctttgca ttttatcttt ttttagcgta ttaaatgaaa   2520
tggttttgaa cgtctcatta cctgatattg caaatgattt taataaacca cctgcgagta   2580
caaactgggt gaacacagcc tttatgttaa ccttttccat tggaacagct gtatatggaa   2640
agctatctga tcaattaggc atcaaaaggt tactcctatt tggaattata ataaattgtt   2700
tcgggtcggt aattgggttt gttggccatt ctttcttttc cttacttatt atggctcgtt   2760
ttattcaagg ggctggtgca gctgcatttc cagcactcgt aatggttgta gttgcgcgct   2820
atattccaaa ggaaaatagg ggtaaagcat ttggtcttat tggatcgata gtagccatgg   2880
gagaaggagt cggtccagcg attggtggaa tgatagccca ttatattcat tggtcctatc   2940
ttctactcat tcctatgata acaattatca ctgttccgtt tcttatgaaa ttattaaaga   3000
aagaagtaag gataaaaggt cattttgata tcaaaggaat tatactaatg tctgtaggca   3060
ttgtattttt tatgttgttt acaacatcat atagcatttc ttttcttatc gttagcgtgc   3120
tgtcattcct gatatttgta aaacatatca ggaaagtaac agatcctttt gttgatcccg   3180
gattagggaa aaatatacct tttatgattg gagttctttg tggggggaatt atatttggaa   3240
cagtagcagg gtttgtctct atggttcctt atatgatgaa agatgttcac cagctaagta   3300
ctgccgaaat cggaagtgta attattttcc ctggaacaat gagtgtcatt attttcggct   3360
acattggtgg gatacttgtt gatagaagag gtcctttata cgtgttaaac atcggagtta   3420
catttctttc tgttagcttt ttaactgctt cctttctttt agaaacaaca tcatggttca   3480
tgacaattat aatcgtattt gttttaggtg ggctttcgtt caccaaaaca gttatatcaa   3540
caattgtttc aagtagcttg aaacagcagg aagctggtgc tggaatgagt ttgcttaact   3600
ttaccagctt ttttatcagag ggaacaggta ttgcaattgt aggtggttta ttatccatac   3660
ccttacttga tcaaaggttg ttacctatgg aagttgatca gtcaacttat ctgtatagta   3720
atttgttatt actttttca ggaatcattg tcattagttg gctggttacc ttgaatgtat   3780
ataaacattc tcaaagggat ttctaaatat gatgaagaaa gaccattcca atcaggaatg   3840
gtcttttttt atgcgcggca aaataaccaa aagcccgtct tataaatttc tttgattaca   3900
ttttataatt aattttaaca aagtgtcatc agccctcagg aaggacttgc tgacagtttg   3960
aatcgcatag gtaaggcggg gatgaaatgg caacgttatc tgatgtagca aagaaagcaa   4020
atgtgtcgaa aatgacggta tcgcgggtga tcaatcatcc tgagactgtg acggatgaat   4080
tgaaaaagct tgttcattcc gcaatgaagg agctcaatta tataccgaac tatgcagcaa   4140
gagcgctcgt tcaaaacaga acacaggtcg tcaagctgct catactggaa gaaatggata   4200
caacagaacc ttattatatg aatctgttaa cgggaatcag ccgcgagctg gaccgtcatc   4260
attatgcttt gcagcttgtc acaaggaaat ctctcaatat cggccagtgc gacggcatta   4320
ttgcgacggg gttgagaaaa gccgattttg aagggctcat caaggttttt gaaaagcctg   4380
tcgttgtatt cgggcaaaat gaaatgggct acgattttat tgatgttaac aatgaaaaag   4440
gaacctatat ggcaacacgt cacgtcattg gtctgggcgt ccgcaatgtc gtcttttttg   4500
ggatcgattt ggatgagc                                                 4518
```

<210> SEQ ID NO 46
<211> LENGTH: 20
<212> TYPE: DNA
<213> ORGANISM: Artificial Sequence
<220> FEATURE:
<223> OTHER INFORMATION: primer

```
<400> SEQUENCE: 46

gcagatgctg ctgaagagat                                          20


<210> SEQ ID NO 47
<211> LENGTH: 20
<212> TYPE: DNA
<213> ORGANISM: Artificial Sequence
<220> FEATURE:
<223> OTHER INFORMATION: primer

<400> SEQUENCE: 47

gctccagttc taggaggatt                                          20


<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48

gggttaatga tacgcttccc                                          20
```

METHODS AND COMPOSITIONS FOR PRODUCING PROTEINS OF INTEREST IN PIGMENT DEFICIENT *BACILLUS* CELLS

CROSS REFERENCE TO RELATED APPLICATIONS

The present application is a U.S. National Stage Application under 35 U.S.C. § 371 of International Application No. PCT/US2022/017339, filed Feb. 22, 2022, which claims priority to U.S. Provisional Patent Application No. 63/151,931, filed Feb. 22, 2021, all of which are hereby incorporated by reference in their entirety.

FIELD

The present disclosure is generally related to the fields of bacteriology, microbiology, genetics, molecular biology, enzymology, industrial protein production the like. Certain embodiments of the disclosure are related to compositions and methods for obtaining pigment deficient *Bacillus* cells, methods for growing/cultivating/fermenting pigment deficient *Bacillus* cells, methods for producing proteins of interest in pigment deficient *Bacillus* cells and the like.

REFERENCE TO A SEQUENCE LISTING

The contents of the electronic submission of the text file Sequence Listing, named "NB41351-US-PSP_Sequence-Listing.txt" was created on Feb. 2, 2021 and is 76 KB in size, which is hereby incorporated by reference in its entirety.

BACKGROUND

Gram-positive bacteria such as *Bacillus subtilis, Bacillus licheniformis, Bacillus amyloliquefaciens* and the like are frequently used as microbial factories for the production of industrial relevant proteins, due to their excellent fermentation properties and high yields (e.g., up to 25 grams per liter culture; Van Dijl and Hecker, 2013). For example, *Bacillus* host cells (strains) are well known for their production of amylases (Jensen et al., 2000; Raul et al., 2014) and proteases (Brode et al., 1996) necessary for food, textile, laundry, medical instrument cleaning, pharmaceutical industries and the like (Westers et al., 2004).

However, *Bacillus* host cells with desirable traits such as increased protein production, enhanced growth rates and the like may not necessarily have the most desirable characteristics for successful fermentation, recovery, and purification of the proteins produced by the cells. For example, these processes may not be optimal because of red pigment formation (i.e., pulcherrimins), requiring removal during the recovery and purification of the protein of interest, or the red pigment may co-purify with the protein. As generally understood in the art, pulcherrimins are reddish pigments resulting from chelation of ferric ions by pulcherriminic acid. The synthesis of pulcherriminic acid by *Bacillus subtilis* (Uffen and Canale-Parola, 1972) and *Bacillus cereus* (MacDonald, 1967) have been described.

Although certain methods have been described for mitigating red pigment (pulcherrimin) formation in *Bacillus* fermentation processes (PCT Publication No. WO2004/011609), these methods may not always be optimal with regard to other desirable traits of the *Bacillus* (host) strain, such as enhanced volumetric productivity, enhanced specific protein production, enhanced total protein production, enhanced growth rates, strain fitness and the like. As described hereinafter, the present disclosure addresses certain ongoing needs in the art for improved *Bacillus* host cells (strains) deficient in the production of red pigment.

SUMMARY

As generally described herein, certain embodiments of the disclosure are related to pigment deficient *Bacillus* cells. Thus, certain embodiments of the disclosure are related to compositions and methods for obtaining pigment deficient *Bacillus* cells and/or compositions and methods for growing/cultivating/fermenting pigment deficient *Bacillus* cells. Other embodiments of the disclosure are related to compositions and methods for producing proteins of interest in pigment deficient *Bacillus* cells. Certain other embodiments are therefore related to compositions and methods for producing, isolating, recovering and the like proteins of interest that are pigment deficient. In other embodiments, the disclosure is related to methods for mitigating, reducing or eliminating red pigment (pulcherrimin) in *Bacillus* fermentation processes via the addition of aluminum ions (e.g., $AlCl_3$).

Thus, certain embodiments of the disclosure are related to genetically modified *Bacillus* cells derived from parental *Bacillus* cells. For example, in certain embodiments, the disclosure is related to a modified *Bacillus* cell derived from a parental *Bacillus* cell, wherein the modified cell comprises an introduced yvmA expression cassette encoding a functional YvmA protein, wherein the modified cell is deficient in the production of a red pigment relative to the parental cell when cultivated under the same conditions.

In certain other embodiments, the disclosure is related to modified *Bacillus* cells derived from parental *Bacillus* cells comprising a yvmA gene encoding a functional YvmA protein. For example, in certain embodiments, the disclosure is related to a modified *Bacillus* cell derived from a parental *Bacillus* cell comprising a yvmA gene encoding a functional YvmA protein, wherein the modified cell comprises a genetic modification which replaces the native yvmA promoter (sequence) of the yvmA gene with a heterologous promoter (sequence) capable of increasing expression of the yvmA gene relative to the native yvmA promoter, wherein the modified cell is deficient in the production of a red pigment relative to the parental cell when cultivated under the same conditions.

In certain embodiments, the modified *Bacillus* cells of the disclosure (i.e., deficient in the production of a red pigment) express and produce one or more proteins of interest. Thus, certain other embodiments are related to an isolated protein of interest (POI) produced by a modified *Bacillus* cell of the disclosure. In other embodiments, an isolated POI produced by a modified *Bacillus* cell of the disclosure comprises no observable red pigment. In certain embodiments, the red pigment is further defined as pulcherrimin.

Certain other embodiments are related to methods for growing/cultivating/fermenting pigment deficient *Bacillus* cells. For example, in certain embodiments, the disclosure is related to a method for cultivating a *Bacillus* cell deficient in the production of a red pigment comprising (a) modifying a parental *Bacillus* cell by introducing therein an expression cassette encoding a functional YvmA protein, and (b) cultivating the modified cell under suitable conditions, wherein the modified cell is deficient in the production of a red pigment relative to the parental cell when cultivated under the same conditions.

Certain other embodiments are related to a method for cultivating a *Bacillus* cell deficient in the production of a red pigment comprising (a) obtaining a parental *Bacillus* cell comprising a yvmA gene encoding a functional YvmA protein and replacing the native yvmA promoter (sequence) of the yvmA gene encoding the functional YvmA protein with a heterologous promoter (sequence) capable of increasing expression of the yvmA gene relative to the native yvmA promoter, and (b) cultivating the modified cell under suitable conditions, wherein the modified cell is deficient in the production of a red pigment relative to the parental cell when cultivated under the same conditions.

Certain other embodiments are related to methods for producing a protein of interest (POI) in pigment deficient *Bacillus* cells. For example, certain embodiments of the disclosure are related to a method for producing a protein of interest (POI) comprising (a) modifying a parental *Bacillus* cell producing a POI by introducing into the parental cell an expression cassette encoding a functional YvmA protein, and (b) fermenting the modified cell under suitable conditions for the production of the POI, wherein the modified cell is deficient in the production of a red pigment relative to the parental cell when fermented under the same conditions.

Certain other embodiments are related to a method for producing a protein of interest (POI) comprising (a) obtaining a parental *Bacillus* cell comprising a yvmA gene encoding a functional YvmA protein and producing a POI, (b) modifying the parental cell by replacing the native yvmA promoter (sequence) of the yvmA gene with a heterologous promoter (sequence) capable of increasing expression of the yvmA gene relative to the native yvmA promoter, and (c) fermenting the modified cell under suitable conditions for the production of the POI, wherein the modified cell is deficient in the production of a red pigment relative to the parental cell when fermented under the same conditions.

In certain embodiments, a POI is an endogenous protein and/or a heterologous protein. In certain embodiments, the endogenous POI and/or a heterologous POI is an enzyme. In certain embodiments, the parental *Bacillus* cell comprises an introduced expression cassette encoding the heterologous POI. In other embodiments, the expression cassette encoding the heterologous POI is introduced into the modified *Bacillus* cell. Thus, certain other embodiments are related to an isolated protein of interest (POI) produced by a modified *Bacillus* cell. In preferred embodiments, the isolated POI comprises no observable red pigment. In certain embodiments, the red pigment is further defined as pulcherrimin.

Certain other embodiments of the disclosure are related to compositions and methods to mitigate red pigment color in a *Bacillus* fermentation broth comprising fermenting a *Bacillus* cell producing a protein of interest (POI) in the presence of an aluminum ion. In certain preferred embodiments, the aluminum ion is provided in the form of $AlCl_3$ or $Al_2(SO_4)3$.

BRIEF DESCRIPTION OF DRAWINGS

FIG. 3 shows that the reduced pulcherrimin levels (e.g., reduced red/brown fermentation broth color) of the *B. subtilis* yvmA overexpressing strains positively correlate with promoter strength. For example.

FIG. 4 shows Phbs-yvmA expression reduces the red/brown fermentation broth color and pulcherrimin levels without affecting the growth rate or protease production in a 2-copy GG36 protease production strain background (FIG. 4A-FIG. 4C). For example.

FIG. 5 shows that deletion of the yvmA gene increases the red/brown fermentation broth color (FIG. 5A) and increases pulcherrimin production (FIG. 5B). For example.

As shown in FIG. 6A, digital images taken at twenty (20) hours and fifty (50) hours of test tube cultures of 1×GG36 ΔyvmA cells grown in the presence of 0 mM, 1 mM, 2 mM, 5 mM and 10 mM $AlCl_3$ for fifty (50) hours at 37° C. in a maltrin-based media.

BRIEF DESCRIPTION OF THE BIOLOGICAL SEQUENCES

Figure 1:
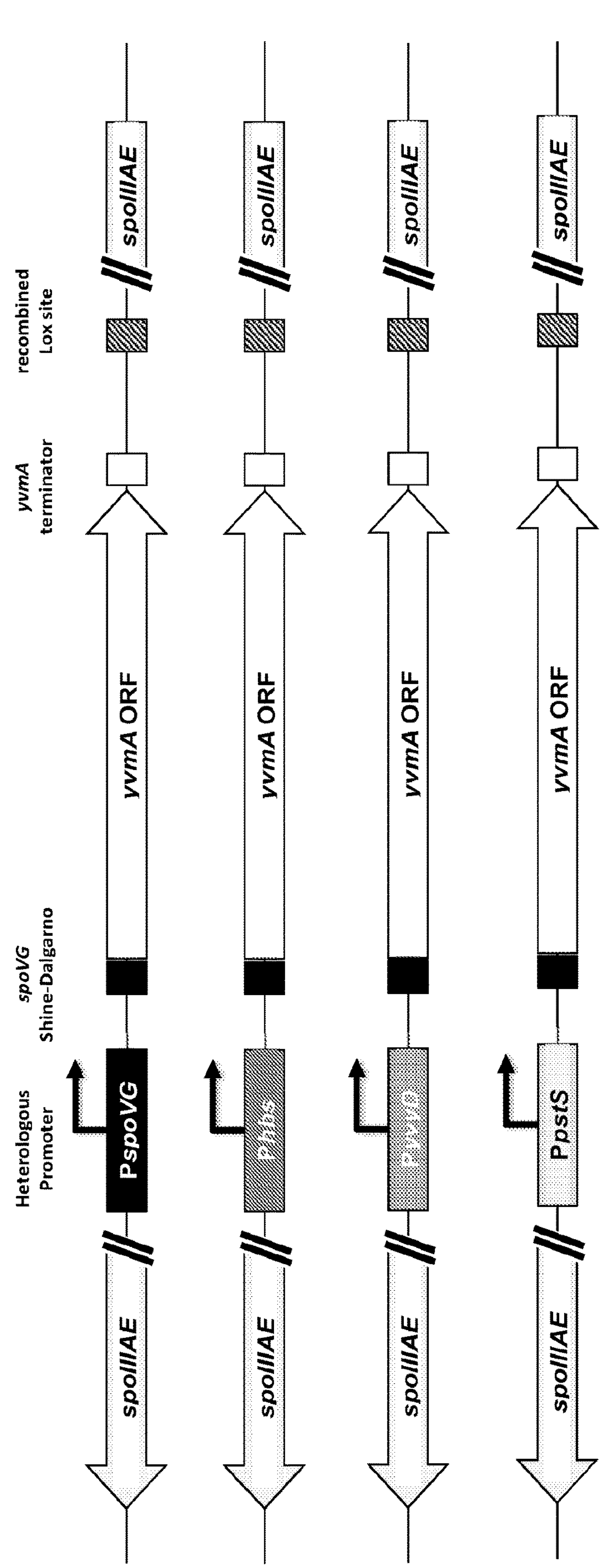
FIG. 1 shows schematic representations of the yvmA overexpression cassettes integrated at the spoIIIAE locus after removal of the spectinomycin antibiotic resistance marker by the Cre-LOX system. For example, as presented in FIG. 1, each yvmA overexpression cassette comprises an upstream (5') heterologous promoter operably linked to the *Bacillus subtilis* yvmA ORF sequence, wherein the heterologous promoters tested (PsoVG, Phbs, PyvyD and PpstS) are marked with an arrow and depicted in decreasing strength from top to bottom (e.g., see FIG. 3A and FIG. 3B). In addition, as presented in FIG. 1, the Shine-Dalgarno sequence (black box) from the spoVG 5'-UTR was used for each overexpression cassette and the native yvmA terminator was maintained (white box). The downstream position of the recombined lox site is indicated with black diagonal hatch markings (FIG. 1).

SEQ ID NO: 1 is an oligonucleotide sequence of primer 265.

SEQ ID NO: 2 is an oligonucleotide sequence of primer 117.

SEQ ID NO: 3 is an oligonucleotide sequence of primer 245.

SEQ ID NO: 4 is an oligonucleotide d sequence of primer 266.

SEQ ID NO: 5 is an oligonucleotide sequence of primer 247.

SEQ ID NO: 6 is an oligonucleotide sequence of primer 55.

SEQ ID NO: 7 is an oligonucleotide sequence of primer 124.

SEQ ID NO: 8 is an oligonucleotide sequence of primer 401.

SEQ ID NO: 9 is an oligonucleotide sequence of primer 298.

SEQ ID NO: 10 is an oligonucleotide sequence of primer 307.

SEQ ID NO: 11 is an oligonucleotide sequence of primer 305.

SEQ ID NO: 12 is an oligonucleotide sequence of primer 308.

SEQ ID NO: 13 is an oligonucleotide sequence of primer 131.

SEQ ID NO: 14 is an oligonucleotide sequence of primer 129.

SEQ ID NO: 15 is an oligonucleotide sequence of primer 299.

SEQ ID NO: 16 is an oligonucleotide sequence of primer 306.

SEQ ID NO: 17 is an oligonucleotide sequence of primer 302.

SEQ ID NO: 18 is a PspoVG-yvmA expression cassette.

SEQ ID NO: 19 is a Phbs-yvmA expression cassette.

SEQ ID NO: 20 is a Pyvyd-yvmA expression cassette.

SEQ ID NO: 21 is a Ppts-yvmA expression cassette.

SEQ ID NO: 22 is an oligonucleotide sequence of primer 241.

SEQ ID NO: 23 is an oligonucleotide sequence of primer 242.

SEQ ID NO: 24 is an oligonucleotide sequence of primer 179.

SEQ ID NO: 25 is an oligonucleotide sequence of primer 282.

SEQ ID NO: 26 is an oligonucleotide sequence of primer 180.

SEQ ID NO: 27 is an oligonucleotide sequence of primer 52.

SEQ ID NO: 28 is an oligonucleotide sequence of primer 53.

SEQ ID NO: 29 is the amino acid sequence of a *B. licheniformis* (wild-type) RghR2 protein.

SEQ ID NO: 30 is the amino acid sequence of a *B. subtilis* YvmA protein.

SEQ ID NO: 31 is a polynucleotide sequence comprising a *B. licheniformis* amyL gene locus.

SEQ ID NO: 32 is a polynucleotide sequence comprising a tet marker.

SEQ ID NO: 33 is a synthetic polynucleotide sequence comprising amyL::[Phbs-yvmA tetR].

SEQ ID NO: 34 is a polynucleotide sequence comprising a *B. licheniformis* upstream (5') amyL homology arm (HA).

SEQ ID NO: 35 is a polynucleotide sequence of the *B. subtilis* hbs promoter (Phbs).

SEQ ID NO: 36 is a nucleic acid sequence of the *B. subtilis* spoVG ribosomal binding site (rbs).

SEQ ID NO: 37 is a polynucleotide sequence of the *B. subtilis* yvmA gene (ORF).

SEQ ID NO: 38 is a polynucleotide sequence of the *B. subtilis* yvmA terminator.

SEQ ID NO: 39 is a polynucleotide sequence comprising a *B. licheniformis* downstream (3') amyL homology arm (HA).

SEQ ID NO: 40 is an artificial polynucleotide sequence

SEQ ID NO: 41 is a polynucleotide sequence of the *B. subtilis* spoVG promoter (PspoVG).

SEQ ID NO: 42 is an oligonucleotide sequence of primer 1762.

SEQ ID NO: 43 is an oligonucleotide sequence of primer 1763.

SEQ ID NO: 44 is the amyL::[Phbs-yvmA tetR] PCR product.

SEQ ID NO: 45 is the amyL::[PspoVG-yvmA tetR] PCR product.

SEQ ID NO: 46 is an oligonucleotide sequence of primer 2377.

SEQ ID NO: 47 is an oligonucleotide sequence of primer 2378.

SEQ ID NO: 48 is an oligonucleotide sequence of primer 2379.

DETAILED DESCRIPTION

As described herein, certain embodiments of the disclosure are related to compositions and methods for obtaining pigment deficient *Bacillus* cells. Thus, certain embodiments are related to compositions and methods for growing (cultivating) pigment deficient *Bacillus* cells. Certain other embodiments are related to compositions and methods for expressing/producing proteins of interest in such pigment deficient *Bacillus* cells. Certain other embodiments are therefore related to compositions and methods for producing, isolating, recovering and the like proteins of interest that are pigment deficient. Certain other embodiments are related to compositions and methods for mitigating, reducing or eliminating red pigment in *Bacillus* fermentation processes via the addition of aluminum ions (e.g., $AlCl_3$).

I. DEFINITIONS

In view of the parental and/or modified (mutant) *Bacillus* cells and related methods described herein, the following terms and phrases are defined. Terms not defined herein should be accorded their ordinary meaning as used in the art.

Unless defined otherwise, all technical and scientific terms used herein have the same meaning as commonly understood by one of ordinary skill in the art to which the present compositions and methods apply. Although any methods and materials similar or equivalent to those described herein can also be used in the practice or testing of the present compositions and methods, representative illustrative methods and materials are now described. All publications and patents cited herein are incorporated by reference in their entirety.

It is further noted that the claims may be drafted to exclude any optional element. As such, this statement is intended to serve as antecedent basis for use of such exclusive terminology as “solely,” “only”, “excluding”, “not including” and the like, in connection with the recitation of claim elements, or use of a “negative” limitation or proviso thereof.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

As used herein, a “host cell” refers to a cell that has the capacity to act as a host or expression vehicle for a newly introduced DNA sequence. Thus, in certain embodiments of the disclosure, the host cells are for example *Bacillus* sp. cells or *E. coli* cells.

As used herein, “modified cells” refers to recombinant (host) cells that comprise at least one genetic modification which is not present in the “parental” host cell from which the modified cells are derived (obtained). For example, in certain embodiments, a “parental” cell is altered (e.g., via one or more genetic modifications introduced into the parental cell) to generate a “modified” (daughter) cell derived therefrom.

In certain embodiments, a parental cell may be referred to as a “control cell”, particularly when being compared with, or relative to, a “modified” *Bacillus* sp. (daughter) cell.

As used herein, when the expression and/or production of a protein of interest (POI) in an “unmodified” (parental) cell (e.g., a control cell) is being compared to the expression and/or production of the same POI in a “modified” (daughter) cell, it will be understood that the “modified” and “unmodified” cells are grown/cultivated/fermented under the same conditions (e.g., the same conditions such as media, temperature, pH and the like).

As used herein, the “genus *Bacillus*” or “*Bacillus* sp.” cells include all species within the genus “*Bacillus*”” as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named “*Geobacillus stearothermophilus*”.

As used herein, the terms “wild-type” and “native” are used interchangeably and refer to genes, promoters, proteins, protein mixes, cells or strains, as found in nature.

As used herein, a *B. subtilis* “yvmA gene”, or an “open reading frame” (ORF) thereof (hereinafter, a “yvmA ORF”), encodes a functional (native) YvmA protein. For example, in certain embodiments, an exemplary *B. subtilis* yvmA ORF encodes a functional YvmA protein comprising substantial amino acid sequence identity to the YvmA protein of SEQ ID NO: 30, or a *Bacillus* sp. YvmA homologue thereof. In other embodiments, a *Bacillus* sp. yvmA ORF encodes a functional YvmA protein comprising at least 85% amino acid sequence identity to the YvmA protein of SEQ ID NO: 30, or a *Bacillus* sp. YvmA homologue thereof. In certain other embodiments, a *Bacillus* sp. yvmA ORF sequence comprises at least about 90% nucleic acid sequence identity to the yvmA ORF sequence of SEQ ID NO: 37, or a *Bacillus* sp. yvmA homologue thereof.

As used herein, phrases such as “yvmA expression cassette”, “yvmA gene expression cassette”, and “yvmA overexpression cassette” may be used interchangeably and refer to expression cassettes described herein comprising an upstream (5') heterologous promoter sequence operably linked to a downstream (3') ORF (nucleic acid sequence) encoding a functional YvmA protein (e.g., see, FIG. 1).

As used herein, the yvmA expression cassette named “PspoVG-yvmA” (SEQ ID NO: 18) comprises an upstream (5') spoVG promoter nucleic acid sequence (“PspoVG”) operably linked to a downstream (3') yvmA ORF (“yvmA”); e.g., encoding the YvmA protein of SEQ ID NO: 30, the cassette named “Phbs-yvmA” (SEQ ID NO: 19) comprises an upstream (5') hbs promoter nucleic acid sequence (“Phbs”) operably linked to the same downstream (3') yvmA ORF, the cassette named “Pyvyd-yvmA” (SEQ ID NO: 20) comprises an upstream (5') yvyd promoter nucleic acid sequence (“Pyvyd”) operably linked to the same downstream (3') yvmA ORF and the cassette named “Ppts-yvmA” (SEQ ID NO: 21) comprises an upstream (5') pts promoter nucleic acid sequence (“Ppts”) operably linked to the same downstream (3') yvmA ORF (e.g., see FIG. 1). As used herein, *B. licheniformis* strains named “BF1175” and “BF1176” are two independent *B. licheniformis* isolates comprising the “Phbs-yvmA tetR” cassette (SEQ ID NO: 33) inserted in the amyL locus; and *B. licheniformis* strains named “BF1177” and “BF1178” are two independent *B. licheniformis* isolates comprising the PspoVG-yvmA tetR cassette (SEQ ID NO: 40) inserted in the amyL locus.

As used herein, the phrase “GG36 protease” refers to a variant serine protease derived from *Bacillus lentus*, as generally described in PCT Publication Nos. WO2011/140316 and WO2012/151534.

As used herein, a parental (control) *B. subtilis* strain named "1×GG36" comprises an expression cassette encoding a single (1) copy of the GG36 protease.

As used herein, a *B. subtilis* strain named "2×GG36" comprises two (2) expression cassettes encoding two (2) copies of the GG36 protease. More particularly, the 2×GG36 strain was generally constructed as described herein in Example 4, wherein the modified *B. subtilis* strain named 1×GG36 Phbs-yvmA (i.e., comprising a single (1) copy of the gene encoding of GG36 protease) was subsequently transformed with a second ($2^{nd}$) expression cassette encoding the same GG36 protease.

As used herein, a "native *Bacillus licheniformis* chromosomal rghR2 gene" comprises a nucleotide sequence encoding a RghR2 protein of SEQ ID NO: 29, wherein the *B. licheniformis* rghR2 gene has been described in PCT Publication No. WO2018/156705 (incorporated herein by reference in its entirety).

As used herein, the phrase "deficient in the production of the red pigment" refers to a modified (mutant) *Bacillus* cell which produces no detectable red pigment, or, in the alternative, produces at least about 5% less red pigment compared to the parent *Bacillus* cell when grown/cultivated/fermented under the same conditions. In certain embodiments, a *Bacillus* cell deficient in the production of the red pigment produces at least about 10% less to about 20% less red pigment compared to the parent *Bacillus* cell when grown/cultivated/fermented under the same conditions. The level of red pigment produced by *Bacillus* cells of the present disclosure may be determined using methods well known in the art, and as described below in the Examples section below.

The terms "modification" and "genetic modification" are used interchangeably and include: (a) the introduction, substitution, or removal of one or more nucleotides in a gene (or an ORF thereof), or the introduction, substitution, or removal of one or more nucleotides in a regulatory element required for the transcription or translation of the gene or ORF thereof, (b) a gene disruption, (c) a gene conversion, (d) a gene deletion, (e) the down-regulation of a gene, (f) specific mutagenesis and/or (g) random mutagenesis of any one or more the genes disclosed herein.

As used herein, "disruption of a gene", "gene disruption", "inactivation of a gene" and "gene inactivation" are used interchangeably and refer broadly to any genetic modification that substantially prevents a host cell from producing a functional gene product (e.g., a protein). Exemplary methods of gene disruptions include complete or partial deletion of any portion of a gene, including a polypeptide-coding sequence, a promoter, an enhancer, or another regulatory element, or mutagenesis of the same, where mutagenesis encompasses substitutions, insertions, deletions, inversions, and any combinations and variations thereof which disrupt/inactivate the target gene(s) and substantially reduce or prevent the production of the functional gene product (i.e., a protein).

As defined herein, the combined term "expresses/produces", as used in phrases such as "a modified (host) cell expresses/produces an increased amount of a protein of interest relative to the parental (host) cell", the term ("expresses/produces") is meant to include any steps involved in the expression and production of a protein of interest in host cell of the disclosure.

As used herein, "increasing" protein production or "increased" protein production is meant an increased amount of protein produced (e.g., an endogenous POI and/or heterologous POI). The protein may be produced inside the host cell, or secreted (or transported) into the culture medium. In certain embodiments, the protein of interest is produced (secreted) into the culture medium. In certain preferred embodiments, the protein of interest is produced (secreted) into the culture medium in the absence of red color/pigment (pulcherrimin) Increased protein production may be detected for example, as higher maximal level of protein or enzymatic activity (e.g., such as protease activity, amylase activity, cellulase activity, hemicellulase activity and the like), or total extracellular protein produced as compared to the parental host cell.

As used herein, "nucleic acid" refers to a nucleotide or polynucleotide sequence, and fragments or portions thereof, as well as to DNA, cDNA, and RNA of genomic or synthetic origin, which may be double-stranded or single-stranded, whether representing the sense or antisense strand. It will be understood that as a result of the degeneracy of the genetic code, a multitude of nucleotide sequences may encode a given protein.

It is understood that the polynucleotides (or nucleic acid molecules) described herein include "genes", "vectors" and "plasmids".

Accordingly, the term "gene", refers to a polynucleotide that codes for a particular sequence of amino acids, which comprise all, or part of a protein coding sequence, and may include regulatory (non-transcribed) DNA sequences, such as promoter sequences, which determine for example the conditions under which the gene is expressed. The transcribed region of the gene may include untranslated regions (UTRs), including introns, 5'-untranslated regions (UTRs), and 3'-UTRs, as well as the coding sequence.

As used herein, the term "coding sequence" refers to a nucleotide sequence, which directly specifies the amino acid sequence of its (encoded) protein product. The boundaries of the coding sequence are generally determined by an open reading frame (hereinafter, "ORF"), which usually begins with an ATG start codon. The coding sequence typically includes DNA, cDNA, and recombinant nucleotide sequences.

The term "promoter" as used herein refers to a nucleic acid sequence capable of controlling the expression of a coding sequence or functional RNA. In general, a coding sequence is located 3' (downstream) to a promoter sequence. Promoters may be derived in their entirety from a native gene, or be composed of different (heterologous) elements derived from different promoters found in nature, or even comprise synthetic nucleic acid segments. It is understood by those skilled in the art that different promoters may direct the expression of a gene in different cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" as used herein refers to the association of nucleic acid sequences on a single nucleic acid fragment so that the function of one is affected by the other. For example, a promoter is operably linked with a coding sequence (e.g., an ORF) when it is capable of affecting the expression of that coding sequence (i.e., that the coding sequence is under the transcriptional control of the promoter). Coding sequences can be operably linked to regulatory sequences in sense or antisense orientation.

A nucleic acid is "operably linked" when it is placed into a functional relationship with another nucleic acid sequence. For example, DNA encoding a secretory leader (i.e., a signal peptide), is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, "a functional promoter sequence controlling the expression of a gene of interest (or ORF thereof) linked to the gene of interest's protein coding sequence" refers to a promoter sequence which controls the transcription and translation of the coding sequence in the host cell (e.g., *Bacillus* cells). For example, in certain embodiments, the present disclosure is directed to a polynucleotide comprising a 5' promoter (or 5' promoter region, or tandem 5' promoters and the like), wherein the promoter region is operably linked to a nucleic acid sequence encoding a protein of the disclosure. Thus, in certain embodiments, a functional promoter sequence controls the expression of a gene encoding a protein disclosed herein. In other embodiments, a functional promoter sequence controls the expression of a heterologous gene (or endogenous gene) encoding a protein of interest in a *Bacillus* cell.

As defined herein, "suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure.

As used herein, the term "introducing", as used in phrases such as "introducing into a bacterial cell" or "introducing into a *Bacillus* sp. cell" at least one polynucleotide open reading frame (ORF), or a gene thereof, or a vector thereof, includes methods known in the art for introducing polynucleotides into a cell, including, but not limited to protoplast fusion, natural or artificial transformation (e.g., calcium chloride, electroporation), transduction, transfection, conjugation and the like (e.g., see Ferrari et al., 1989).

As used herein, "transformed" or "transformation" mean a cell has been transformed by use of recombinant DNA techniques. Transformation typically occurs by insertion of one or more nucleotide sequences (e.g., a polynucleotide, an ORF or gene) into a cell. The inserted nucleotide sequence may be a heterologous nucleotide sequence (i.e., a sequence that is not naturally occurring in cell that is to be transformed). For example, in certain embodiments of the disclosure, a parental *Bacillus* cell is modified (e.g., transformed) by introducing into the parental cell a polynucleotide construct comprising a promoter operably linked to a nucleic acid sequence encoding a protein of interest, thereby resulting in a modified *Bacillus* (daughter) host cell derived from the parental cell.

As used herein, "transformation" refers to introducing an exogenous DNA into a host cell so that the DNA is maintained as a chromosomal integrant or a self-replicating extra-chromosomal vector. As used herein, "transforming DNA", "transforming sequence", and "DNA construct" refer to DNA that is used to introduce sequences into a host cell or organism. Transforming DNA is DNA used to introduce sequences into a host cell or organism. The DNA may be generated in vitro by PCR or any other suitable techniques. In some embodiments, the transforming DNA comprises an incoming sequence, while in other embodiments it further comprises an incoming sequence flanked by homology boxes. In yet a further embodiment, the transforming DNA comprises other non-homologous sequences, added to the ends (i.e., stuffer sequences or flanks). The ends can be closed such that the transforming DNA forms a closed circle, such as, for example, insertion into a vector.

As used herein "an incoming sequence" refers to a DNA sequence that is introduced into the *Bacillus* chromosome. In some embodiments, the incoming sequence is part of a DNA construct. In other embodiments, the incoming sequence encodes one or more proteins of interest. In some embodiments, the incoming sequence comprises a sequence that may or may not already be present in the genome of the cell to be transformed (i.e., it may be either a homologous or heterologous sequence). In some embodiments, the incoming sequence encodes one or more proteins of interest, a gene, and/or a mutated or modified gene. In alternative embodiments, the incoming sequence encodes a functional wild-type gene or operon, a functional mutant gene or operon, or a nonfunctional gene or operon. In some embodiments, the non-functional sequence may be inserted into a gene to disrupt function of the gene. In another embodiment, the incoming sequence includes a selective marker. In a further embodiment the incoming sequence includes two homology boxes.

As used herein, "homology box" refers to a nucleic acid sequence, which is homologous to a sequence in the *Bacillus* chromosome. More specifically, a homology box is an upstream or downstream region having between about 80 and 100% sequence identity, between about 90 and 100% sequence identity, or between about 95 and 100% sequence identity with the immediate flanking coding region of a gene or part of a gene to be deleted, disrupted, inactivated, down-regulated and the like, according to the invention. These sequences direct where in the *Bacillus* chromosome a DNA construct is integrated and directs what part of the *Bacillus* chromosome is replaced by the incoming sequence. While not meant to limit the present disclosure, a homology box may include about between 1 base pair (bp) to 200 kilobases (kb). Preferably, a homology box includes about between 1 bp and 10.0 kb; between 1 bp and 5.0 kb; between 1 bp and 2.5 kb; between 1 bp and 1.0 kb, and between 0.25 kb and 2.5 kb. A homology box may also include about 10.0 kb, 5.0 kb, 2.5 kb, 2.0 kb, 1.5 kb, 1.0 kb, 0.5 kb, 0.25 kb and 0.1 kb. In some embodiments, the 5' and 3' ends of a selective marker are flanked by a homology box wherein the homology box comprises nucleic acid sequences immediately flanking the coding region of the gene.

As used herein, the term "selectable marker-encoding nucleotide sequence" refers to a nucleotide sequence which is capable of expression in the host cells and where expression of the selectable marker confers to cells containing the expressed gene the ability to grow in the presence of a corresponding selective agent or lack of an essential nutrient.

As used herein, the terms "selectable marker" and "selective marker" refer to a nucleic acid (e.g., a gene) capable of expression in host cell which allows for ease of selection of those hosts containing the vector. Examples of such selectable markers include, but are not limited to, antimicrobials. Thus, the term "selectable marker" refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation.

A "residing selectable marker" is one that is located on the chromosome of the microorganism to be transformed. A residing selectable marker encodes a gene that is different from the selectable marker on the transforming DNA construct. Selective markers are well known to those of skill in the art. As indicated above, the marker can be an antimicrobial resistance marker (e.g., ampR, phleoR, specR, kanR, eryR, tetR, cmpR and neoR (see e.g., Guerot-Fleury, 1995; Palmeros et al., 2000; and Trieu-Cuot et al., 1983). In some embodiments, the present disclosure provides a chloramphenicol resistance gene (e.g., the gene present on pC194, as well as the resistance gene present in the *Bacillus* genome). This resistance gene is particularly useful in the present invention, as well as in embodiments involving chromosomal amplification of chromosomally integrated cassettes and integrative plasmids (see e.g., Albertini and Galizzi, 1985; Stahl and Ferrari, 1984). Other markers useful in accordance with the invention include, but are not limited to auxotrophic markers, such as serine, lysine, tryptophan; and detection markers, such as β-galactosidase or fluorescent proteins.

As defined herein, a host cell "genome", a bacterial (host) cell "genome", or a *Bacillus* (host) cell "genome" includes chromosomal and extrachromosomal genes.

As used herein, the terms "plasmid", "vector" and "cassette" refer to extrachromosomal elements, often carrying genes which are typically not part of the central metabolism of the cell, and usually in the form of circular double-stranded DNA molecules. Such elements may be autonomously replicating sequences, genome integrating sequences, phage or nucleotide sequences, linear or circular, of a single-stranded or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A used herein, a "transformation cassette" refers to a specific vector comprising a gene (or ORF thereof), and having elements in addition to the foreign gene that facilitate transformation of a particular host cell.

As used herein, the term "vector" refers to any nucleic acid that can be replicated (propagated) in cells and can carry new genes or DNA segments into cells. Thus, the term refers to a nucleic acid construct designed for transfer between different host cells. Vectors include viruses, bacteriophage, pro-viruses, plasmids, phagemids, transposons, and artificial chromosomes such as YACs (yeast artificial chromosomes), BACs (bacterial artificial chromosomes), PLACs (plant artificial chromosomes), and the like, that are "episomes" (i.e., replicate autonomously or can integrate into a chromosome of a host organism).

An "expression vector" refers to a vector that has the ability to incorporate and express heterologous DNA in a cell. Many prokaryotic and eukaryotic expression vectors are commercially available and know to one skilled in the art. Selection of appropriate expression vectors is within the knowledge of one skilled in the art.

As used herein, the terms "expression cassette" and "expression vector" refer to a nucleic acid construct generated recombinantly or synthetically, with a series of specified nucleic acid elements that permit transcription of a particular nucleic acid in a target cell (i.e., these are vectors or vector elements, as described above). The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In some embodiments, DNA constructs also include a series of specified nucleic acid elements that permit transcription of a particular nucleic acid in a target cell. In certain embodiments, a DNA construct of the disclosure comprises a selective marker and an inactivating chromosomal or gene or DNA segment as defined herein.

As used herein, a "targeting vector" is a vector that includes polynucleotide sequences that are homologous to a region in the chromosome of a host cell into which the targeting vector is transformed and that can drive homologous recombination at that region. For example, targeting vectors find use in introducing mutations into the chromosome of a host cell through homologous recombination. In some embodiments, the targeting vector comprises other non-homologous sequences, e.g., added to the ends (i.e., stuffer sequences or flanking sequences). In some embodiments the targeting vectors include elements to increase homologous recombination with the chromosome including but not limited to RNA-guided endonucleases, DNA-guided endonucleases, and recombinases. The ends can be closed such that the targeting vector forms a closed circle, such as, for example, insertion into a vector.

As used herein, the term "plasmid" refers to a circular double-stranded (ds) DNA construct used as a cloning vector, and which forms an extrachromosomal self-replicating genetic element in many bacteria and some eukaryotes. In some embodiments, plasmids become incorporated into the genome of the host cell.

As used herein, the term "protein of interest" or "POI" refers to a polypeptide of interest that is desired to be expressed in a *Bacillus* host cell. Thus, as used herein, a POI may be an enzyme, a substrate-binding protein, a surface-active protein, a structural protein, a receptor protein, and the like. In certain embodiments, a modified cell of the disclosure produces an increased amount of a heterologous POI or an increased amount of an endogenous POI, relative to the parental cell. In particular embodiments, an increased amount of a POI produced by a modified cell of the disclosure is at least a 0.5% increase, at least a 1.0% increase, at least a 5.0% increase, or a greater than 5.0% increase, relative to the parental cell.

As used herein, a "gene of interest" or "GOP" refers a nucleic acid sequence (e.g., a polynucleotide, a gene or an ORF) which encodes a POI. A "gene of interest" encoding a "protein of interest" may be a naturally occurring gene, a mutated gene or a synthetic gene.

As used herein, the terms "polypeptide" and "protein" are used interchangeably, and refer to polymers of any length comprising amino acid residues linked by peptide bonds. The conventional one (1) letter or three (3) letter codes for amino acid residues are used herein. The polypeptide may be linear or branched, it may comprise modified amino acids, and it may be interrupted by non-amino acids. The term polypeptide also encompasses an amino acid polymer that has been modified naturally or by intervention;

for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

In certain embodiments, a gene of the instant disclosure encodes a commercially relevant industrial protein of interest, such as an enzyme (e.g., a acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof).

As used herein, the term "equivalent positions" mean the amino acid residue positions after alignment with a specified polypeptide sequence.

As used herein, a "variant" polypeptide refers to a polypeptide that is derived from a parent (or reference) polypeptide by the substitution, addition, or deletion of one or more amino acids, typically by recombinant DNA techniques. Variant polypeptides may differ from a parent polypeptide by a small number of amino acid residues and may be defined by their level of primary amino acid sequence homology/identity with a parent (reference) polypeptide.

Preferably, variant polypeptides have at least 70%, at least 75%, at least 80%, at least 85%, at least 90%, at least 91%, at least 92%, at least 93%, at least 94%, at least 95%, at least 96%, at least 97%, at least 98%, or even at least 99% amino acid sequence identity with a parent (reference) polypeptide sequence.

As used herein, a "variant" polynucleotide refers to a polynucleotide encoding a variant polypeptide, wherein the "variant polynucleotide" has a specified degree of sequence homology/identity with a parent polynucleotide, or hybridizes with a parent polynucleotide (or a complement thereof) under stringent hybridization conditions. Preferably, a variant polynucleotide has at least 70%, at least 75%, at least 80%, at least 85%, at least 90%, at least 91%, at least 92%, at least 93%, at least 94%, at least 95%, at least 96%, at least 97%, at least 98%, or even at least 99% nucleotide sequence identity with a parent (reference) polynucleotide sequence.

As used herein, a "mutation" refers to any change or alteration in a nucleic acid sequence. Several types of mutations exist, including point mutations, deletion mutations, silent mutations, frame shift mutations, splicing mutations and the like. Mutations may be performed specifically (e.g., via site directed mutagenesis) or randomly (e.g., via chemical agents, passage through repair minus bacterial strains).

As used herein, in the context of a polypeptide or a sequence thereof, the term "substitution" means the replacement (i.e., substitution) of one amino acid with another amino acid.

As used herein, an "endogenous gene" refers to a gene in its natural location in the genome of an organism.

As used herein, a "heterologous" gene, a "non-endogenous" gene, or a "foreign" gene refer to a gene (or ORF) not normally found in the host organism, but that is introduced into the host organism by gene transfer.

As used herein, the term "foreign" gene(s) comprise native genes (or ORFs) inserted into a non-native organism and/or chimeric genes inserted into a native or non-native organism.

As used herein, a "heterologous" nucleic acid construct or a "heterologous" nucleic acid sequence has a portion of the sequence which is not native to the cell in which it is expressed.

As defined herein, a "heterologous control sequence", refers to a gene expression control sequence (e.g., a promoter or enhancer) which does not function in nature to regulate (control) the expression of the gene of interest. Generally, heterologous nucleic acid sequences are not endogenous (native) to the cell, or a part of the genome in which they are present, and have been added to the cell, by infection, transfection, transformation, microinjection, electroporation, and the like. A "heterologous" nucleic acid construct may contain a control sequence/DNA coding (ORF) sequence combination that is the same as, or different, from a control sequence/DNA coding sequence combination found in the native host cell.

As used herein, the terms "signal sequence" and "signal peptide" refer to a sequence of amino acid residues that may participate in the secretion or direct transport of a mature protein or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

The term "derived" encompasses the terms "originated" "obtained," "obtainable," and "created," and generally indicates that one specified material or composition finds its origin in another specified material or composition, or has features that can be described with reference to the another specified material or composition.

As used herein, the term "homology" relates to homologous polynucleotides or polypeptides. If two or more polynucleotides or two or more polypeptides are homologous, this means that the homologous polynucleotides or polypeptides have a "degree of identity" of at least 50%, or at least 60%, more preferably at least 70%, even more preferably at least 80-85%, still more preferably at least 90%, more preferably at least 95%, and most preferably at least 98%. Whether two polynucleotide or polypeptide sequences have a sufficiently high degree of identity to be homologous as defined herein, can suitably be investigated by aligning the two sequences using a computer program known in the art, such as "GAP" provided in the GCG program package (Program Manual for the Wisconsin Package, Version 8, August 1994, Genetics Computer Group, 575 Science Drive, Madison, Wisconsin, USA 53711) (Needleman and Wunsch, (1970). Using GAP with the following settings for DNA sequence comparison: GAP creation penalty of 5.0 and GAP extension penalty of 0.3.

As used herein, the term "percent (%) identity" refers to the level of nucleic acid or amino acid sequence identity between the nucleic acid sequences that encode a polypeptide or the polypeptide's amino acid sequences, when aligned using a sequence alignment program.

As used herein, "specific productivity" is total amount of protein produced per cell per time over a given time period.

As used herein, the terms "purified", "isolated" or "enriched" are meant that a biomolecule (e.g., a polypeptide or polynucleotide) is altered from its natural state by virtue of separating it from some, or all of, the naturally occurring constituents with which it is associated in nature. Such isolation or purification may be accomplished by art-recognized separation techniques such as ion exchange chromatography, affinity chromatography, hydrophobic separation, dialysis, protease treatment, ammonium sulphate precipitation or other protein salt precipitation, centrifugation, size exclusion chromatography, filtration, microfiltration, gel electrophoresis or separation on a gradient to remove whole cells, cell debris, impurities, extraneous proteins, or enzymes undesired in the final composition. It is further possible to then add constituents to a purified or isolated biomolecule composition which provide additional benefits, for example, activating agents, anti-inhibition agents, desirable ions, compounds to control pH or other enzymes or chemicals.

As used herein, the term "ComK polypeptide" is defined as the product of a comK gene; a transcription factor that acts as the final auto-regulatory control switch prior to competence development; involved with activation of the expression of late competence genes involved in DNA-binding and uptake and in recombination (Liu and Zuber, 1998, Hamoen et al., 1998).

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes). For example, in certain embodiments a yvmA gene (or ORF thereof) of the disclosure is a homologue of the *B. subtilis* yvmA gene (SEQ ID NO: 37). In other embodiments, a yvmA gene (or ORF thereof) of the disclosure encodes a homologue of the *B. subtilis* YvmA protein (SEQ ID NO: 30).

As used herein, "orthologue" and "orthologous genes" refer to genes in different species that have evolved from a common ancestral gene (i.e., a homologous gene) by speciation. Typically, orthologues retain the same function during the course of evolution. Identification of orthologues finds use in the reliable prediction of gene function in newly sequenced genomes.

As used herein, "paralog" and "paralogous genes" refer to genes that are related by duplication within a genome. While orthologues retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "homology" refers to sequence similarity or identity, with identity being preferred. This homology is determined using standard techniques known in the art (see e.g., Smith and Waterman, 1981; Needleman and Wunsch, 1970; Pearson and Lipman, 1988; programs such as GAP, BESTFIT, FASTA, and TFASTA in the Wisconsin Genetics Software Package (Genetics Computer Group, Madison, WI) and Devereux et. al., 1984).

As used herein, the term "hybridization" refers to the process by which a strand of nucleic acid joins with a complementary strand through base pairing, as known in the art. A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature ($T_m$) of the nucleic acid binding complex or probe. For example, "maximum stringency" typically occurs at about $T_m$ 5° C. (5° below the $T_m$ of the probe); "high stringency" at about 5-10° C. below the $T_m$; "intermediate stringency" at about 10-20° C. below the $T_m$ of the probe; and "low stringency" at about 20-25° C. below the $T_m$. Functionally, maximum stringency conditions may be used to identify sequences having strict identity or near-strict identity with the hybridization probe; while an intermediate or low stringency hybridization can be used to identify or detect polynucleotide sequence homologs. Moderate and high stringency hybridization conditions are well known in the art. An example of high stringency conditions includes hybridization at about 42° C. in 50% formamide, 5×SSC, 5×Denhardt's solution, 0.5% SDS and 100 pg/ml denatured carrier DNA, followed by washing two times in 2×SSC and 0.5% SDS at room temperature (RT) and two additional times in 0.1×SSC and 0.5% SDS at 42° C. An example of moderate stringent conditions including overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denatured sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. "Recombination", "recombining" or generating a "recombined" nucleic acid is the assembly of two or more nucleic acid fragments wherein the assembly gives rise to a chimeric gene.

As used herein, a "flanking sequence" refers to any sequence that is either upstream or downstream of the sequence being discussed (e.g., for genes A-B-C, gene B is flanked by the A and C gene sequences). In certain embodiments, the incoming sequence is flanked by a homology box on each side. In another embodiment, the incoming sequence and the homology boxes comprise a unit that is flanked by stuffer sequence on each side. In some embodiments, a flanking sequence is present on only a single side (either 3' or 5'), but in preferred embodiments, it is on each side of the sequence being flanked. The sequence of each homology box is homologous to a sequence in the *Bacillus* chromosome. These sequences direct where in the *Bacillus* chromosome the new construct gets integrated and what part of the *Bacillus* chromosome will be replaced by the incoming sequence. In other embodiments, the 5' and 3' ends of a selective marker are flanked by a polynucleotide sequence comprising a section of the inactivating chromosomal segment. In some embodiments, a flanking sequence is present on only a single side (either 3' or 5'), while in other embodiments, it is present on each side of the sequence being flanked. In some embodiments, the homology boxes are directly flanking each other and lacking an intervene sequence (e.g. for genes D-E-F the construct D-F) such that if the construct recombines within the genome gene E will be removed from the genome.

II. RED PIGMENT (PULCHERRIMIN)

As generally described above, *Bacillus* cells (strains) are frequently used as microbial factories for the production of industrial relevant proteins (e.g., amylases, proteases, etc.) necessary for food, textile, laundry, medical instrument cleaning, pharmaceutical industries and the like. Thus, *Bacillus* host strains with desirable traits/phenotypes such as enhanced protein production, enhanced growth rates, enhanced fitness and the like, are particularly suitable host strains for the production of proteins of interest. However, as briefly stated above and described hereinafter, when fermenting certain *Bacillus* strains, the fermentation broth forms (accumulates) an undesirable red pigment known as pulcherrimin. For example, when fermenting *Bacillus* cells for the production of a protein of interest (POI), any red pigment formed (present) in the fermentation broth typically requires costly processing steps (e.g., during the recovery and purification of the POI) to avoid/mitigate the red pigment co-purifying with the POI.

As generally understood in the art, pulcherrimins are reddish pigments resulting from chelation of ferric ions by pulcherriminic acid, wherein the pulcherrimin formed in the fermentation broth (cultivation media) is produced by the chelation of two (2) iron molecules ($Fe^{3+}$) with pulcherriminic acid. For example, the synthesis of pulcherriminic acid by certain *Bacillus* sp. cells have been described (Uffen and Canale-Parola, 1972; MacDonald, 1967). PCT Publication No. WO2004/011609 discloses methods for mitigating red pigment in *B. subtilis* fermentations by deleting the cypX gene and/or yvmC gene in such *B. subtilis* strains. More recently, the *B. subtilis* YvmB (MarR-like) protein has been described as the major transcription factor controlling yvmC-cypX (operon) expression (Randazzo et al., 2016). As reviewed in Randazzo et al. (2016), in *B. subtilis* cells, YvmC converts leu-tRNA to cyclo-L-leucyl-L-leucyl and subsequent catalysis of cyclo-L-leucyl-L-leucyl to pulcherriminic acid is performed by CypX, wherein pulcherriminic acid is secreted by *B. subtilis* by an unknown mechanism. In addition, the role of pulcherrimin formation and growth arrest of *B. subtilis* biofilms have been described (Arnaouteli et al., 2019).

As described herein and the Examples section below, Applicant has identified a novel means to mitigate, reduce or eliminate the production of red pigment (pulcherrimin) observed in certain *Bacillus* fermentations. More particularly, as exemplified herein, Applicant has surprisingly discovered that *Bacillus* cells over-expressing a *B. subtilis* yvmA gene are particularly deficient in the production of pulcherrimin, whereas *Bacillus* cells having a deletion of the yvmA gene (ΔyvmA) produce increased levels of pulcherrimin in the fermentation broth. Likewise, as exemplified herein, Applicant has surprisingly observed that aluminum ions (e.g., $AlCl_3$) are an efficient chemical means to mitigate, reduce or eliminate red pigment (pulcherrimin) formation is *Bacillus* fermentation processes.

More specifically, as set forth below in Example 1, Applicant constructed certain yvmA (gene) over-expression cassettes (e.g., see FIG. 1) to assess the influence of YvmA as related to pulcherrimin (red pigment) formation in the fermentation broth. For example, the *B. subtilis* yvmA gene is part of the yvmB-yvmA operon, which is adjacent to the yvmC-cypX operon. The yvmA gene encodes a putative transporter protein that has motifs like the MFS (Major Facilitator Superfamily) class of transporters, wherein some members of this class of transporters function in iron homeostasis (Pi and Helman, 2017).

Figure 2A:
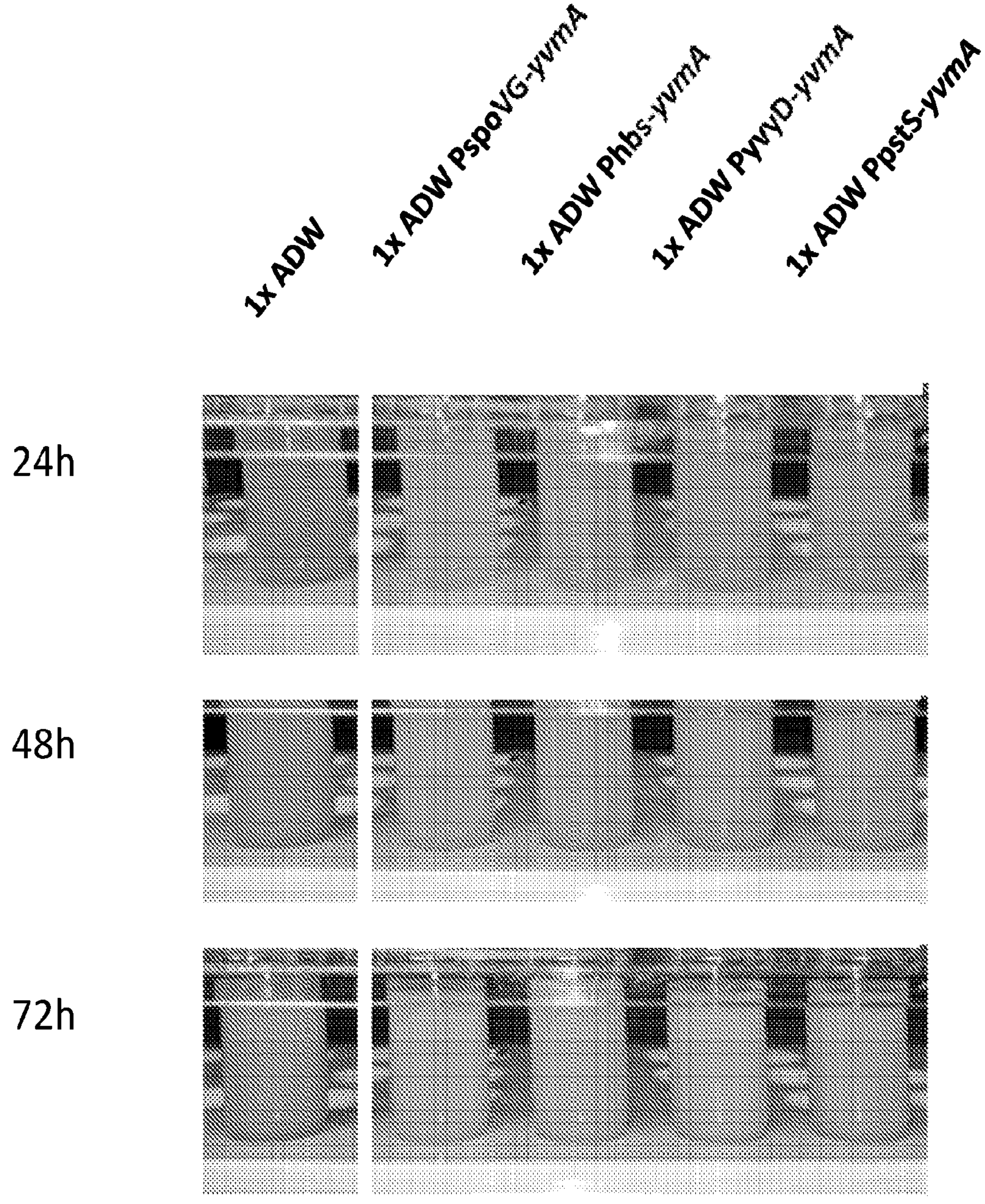
FIG. 2 demonstrates that constitutive overexpression of yvmA in *B. subtilis* host cells (strains) reduces the red/brown fermentation broth color. For example, digital images of the 1×GG36 strain, the 1×GG36 PspoVG-yvmA strain, the 1×GG36 Phbs-yvmA strain, the 1×GG36 PyvyD-yvmA strain and the 1×GG36 Ppts-yvmA strain test tube cultures grown for twenty-four (24), forty-eight (48) and seventy-two (72) hours at 37° C. in maltrin-based media, are presented in FIG. 2A. In addition, as shown in FIG. 2B, quantification of the reduction of the red/brown fermentation broth color due to the constitutive overexpression of yvmA in *B. subtilis* production strains confirms the qualitative results observed in FIG. 2A. For example, luminance of the digital images shown in FIG. 2A, which depict the 1×ADW strain, the 1×GG36 PspoVG-yvmA strain, the 1×GG36 Phbs-yvmA strain, the 1×GG36 PyvyD-yvmA strain and the 1×GG36 Ppts-yvmA strain test tube cultures grown for twenty-four (24), forty-eight (48) and seventy-two (72) hours at 37° C. in maltrin-based media, are presented in FIG. 2B, wherein luminance (AU) was quantitated using Fiji software, as described in Schindelin et al. (2012).
Figure 2B:
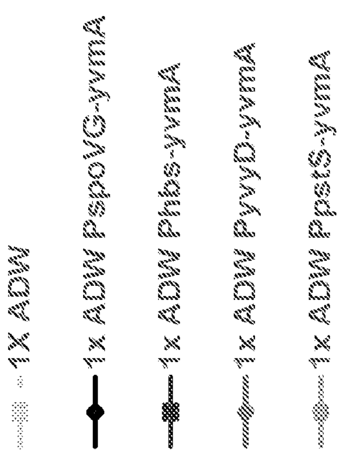
Figure 3A:
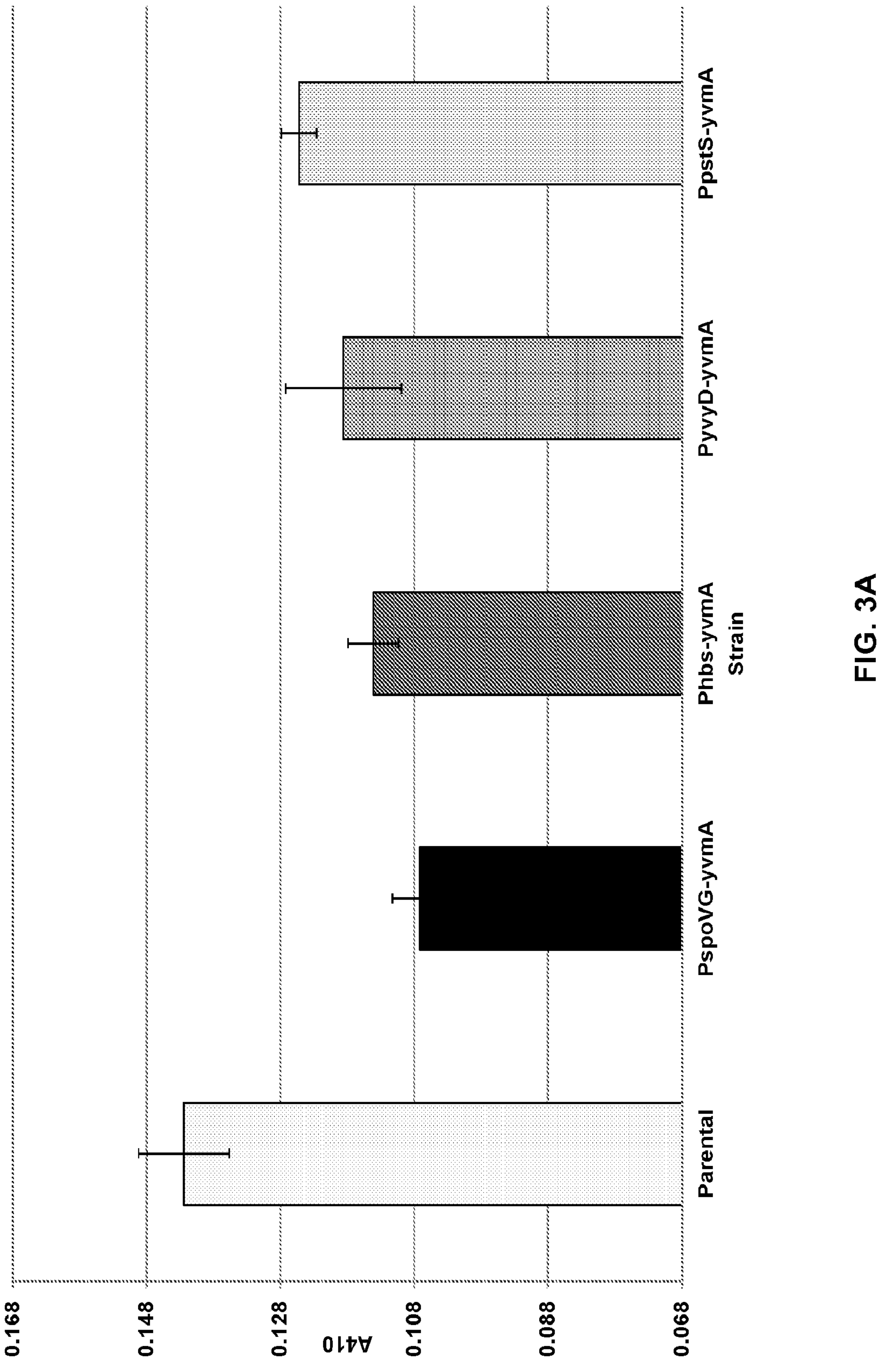
FIG. 3A shows the effect of yvmA overexpression on pellet associated pulcherrimin at seventy-two (72) hours fermentation (n=3), wherein histograms depicting pulcherrimin levels were determined for 1×GG36, 1×GG36 PspoVG-yvmA, 1×GG36 Phbs-yvmA, 1×GG36 PyvyD-yvmA and 1×GG36 Ppts-yvmA strains after seventy-two (72) hours of growth at 37° C. As presented in FIG. 3A, promoter strength is indicated with light to dark histogram shading, wherein the light to dark shadings indicate increasing promoter strength, respectively.
Figure 3B:
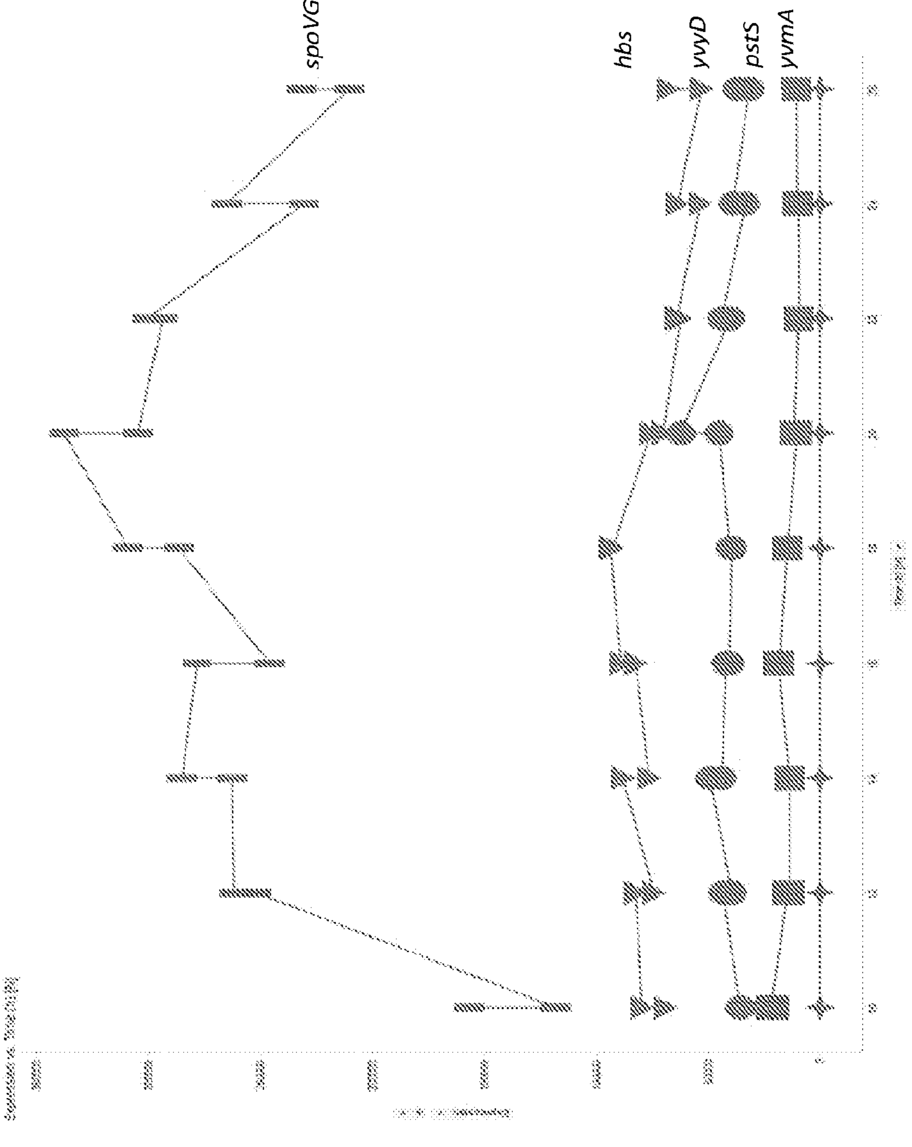
FIG. 3B shows the mRNA levels of the 1×GG36 PspoVG-yvmA, 1×GG36 Phbs-yvmA, 1×GG36 PyvyD-yvmA and 1×GG36 Ppts-yvmA strains quantitated by RNA-seq analysis over time during a soy based industrial fermentation.

As shown in FIG. 1, the yvmA expression cassettes constructed (Example 1) comprise an upstream (5') heterologous promoter sequence operably linked to a downstream (3') yvmA open reading frame (ORF) sequence, e.g., PspoVG-yvmA (SEQ ID NO: 18), Phbs-yvmA (SEQ ID NO: 19), PyvyD-yvmA (SEQ ID NO: 20) and PpstS-yvmA (SEQ ID NO: 21). In addition, to study the effect of over-expressing yvmA in *Bacillus* cells expressing/producing a POI, Applicant constructed *B. subtilis* cells producing a protease and over-expressing yvmA (Example 2). For example, as generally described in Example 3, digital images were taken of the cultures at twenty-four (24), forty-eight (48), seventy-two (72) hours, wherein a decrease in the red/brown color of the broth was readily observable in the (GG36) protease producing *B. subtilis* cells over-expressing yvmA, as compared to the parental (GG36) protease producing *B. subtilis* cells, across the fermentation time course (FIG. 2A). As shown in FIG. 2B, an increase in the luminance of the yvmA over-expression cells compared (relative) to the parental (GG36) protease producing cells during the same time course was also readily apparent, further noting that the degree of observable red/brown color reduction correlates with the strength of the promoter that over-expresses yvmA. For example, the strongest promoter tested, spoVG reduced the red/brown color more than yvmA expression from the weakest promoter tested, pstS (FIG. 2B). Furthermore, to determine if the reduction in red/brown broth color observed for the yvmA over-expressing cells was due to a reduction in pulcherrimin, Applicant quantified the relative amounts of pulcherrimin produced by the parental and modified cells after seventy-two (72) hours, as shown in FIG. 3A and FIG. 3B.

Figure 4A:
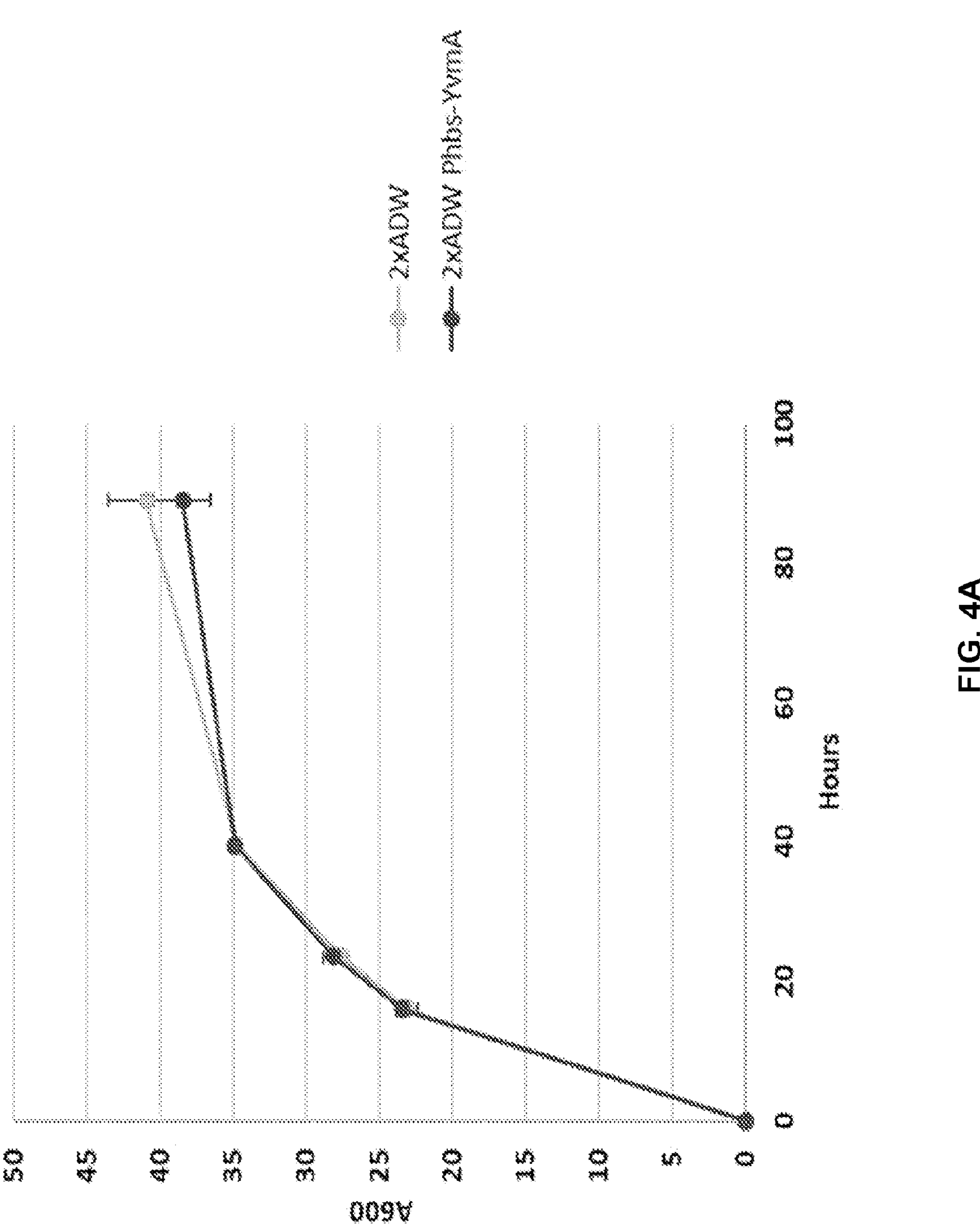
FIG. 4A presents growth curves of 2×GG36 (parental) and 2×GG36 Phbs-yvmA (modified) strains grown in defined media (n=3), wherein growth was monitored by A600.
Figure 4B:
FIG. 4B shows the protease activity assays for 2×GG36 (parental) and 2×GG36 Phbs-yvmA (modified) strains grown in defined media (n=3) and FIG. 4C shows a pulcherrimin quantification assay for 2×GG36 (parental) and 2×GG36 Phbs-yvmA (modified) strains grown in maltrin-based media and assayed after sixty-seven (67) hours (n=3).
Figure 4B:
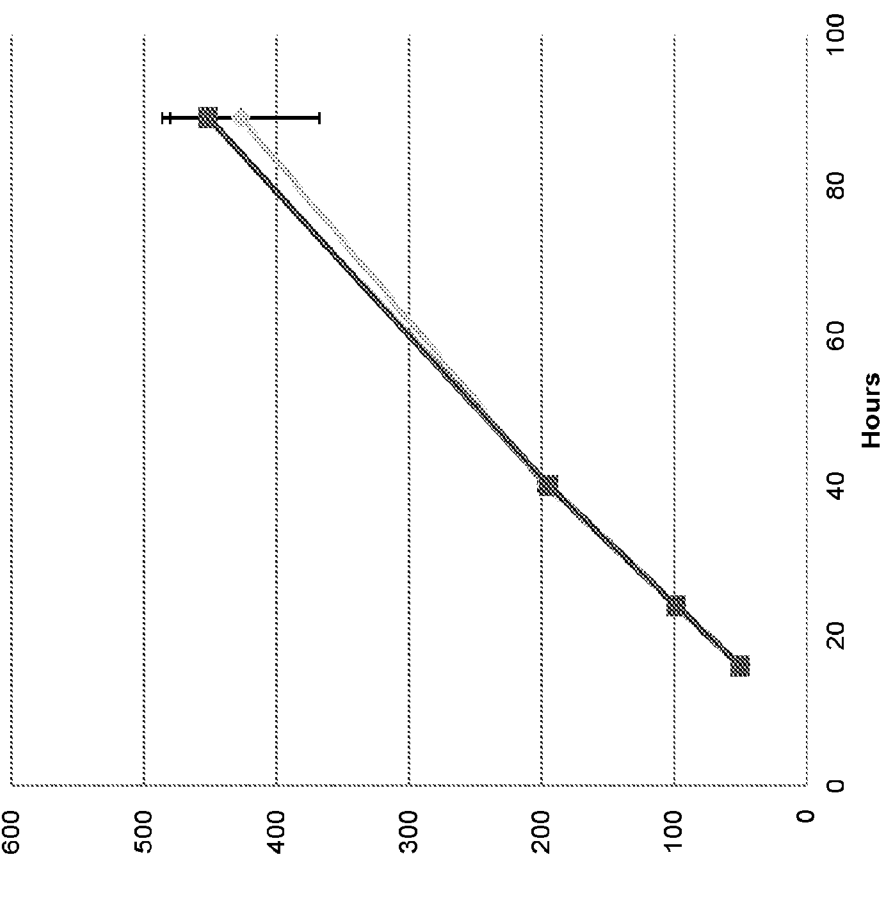
Figure 4C:
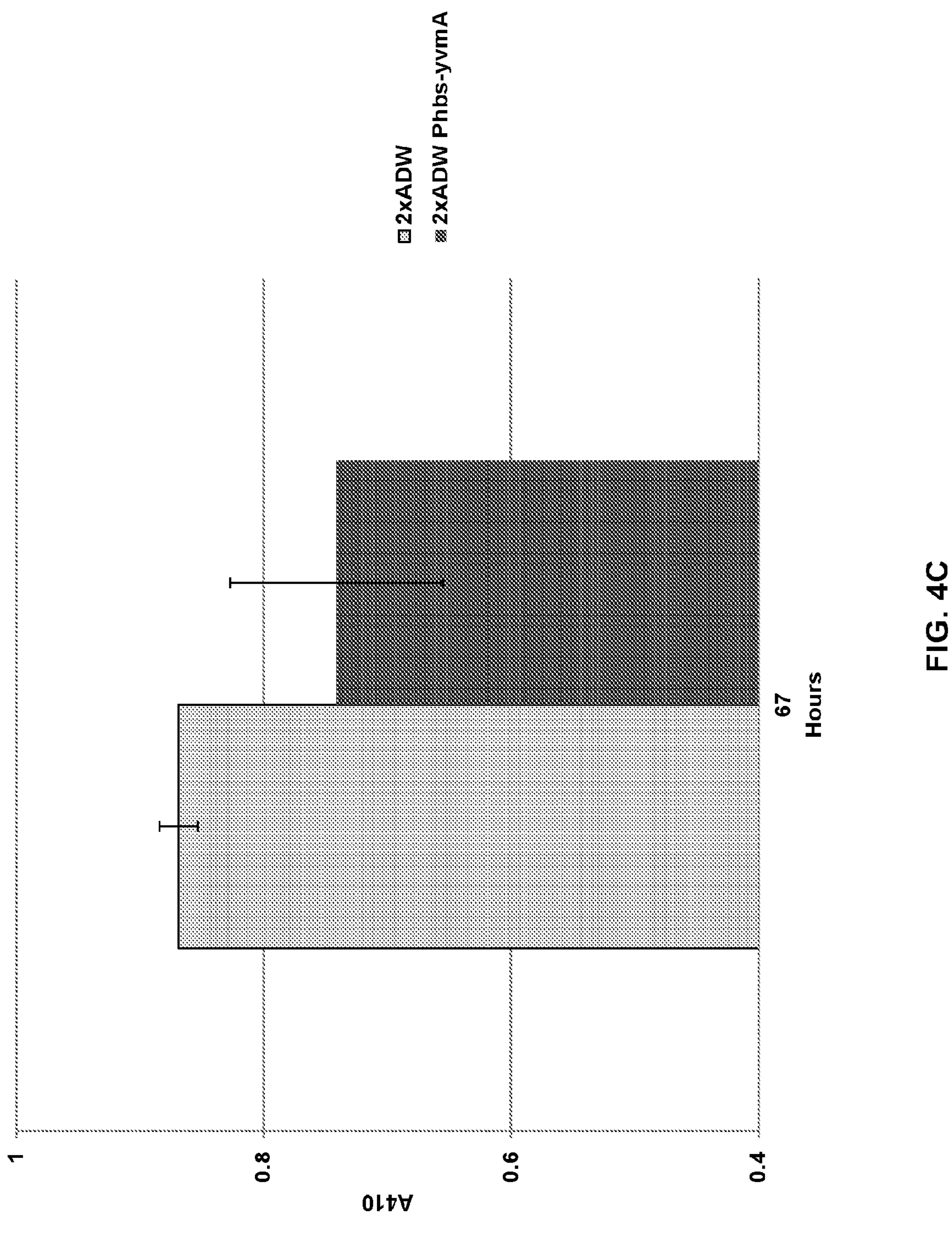

Example 4 further describes the construction of *B. subtilis* cells expressing two (2) copies an exemplary POI (2×GG36 protease) and over-expressing yvmA (2×GG36 Phbs-yvmA). As described in Example 5, Applicant assessed over-expression of yvmA on the growth rate of the *Bacillus* two (2) copy protease producing strain (2×GG36 Phbs-yvmA), wherein the growth rate of the strains was monitored via spectrometer absorbance of samples taken at eighteen (18), twenty-four (24), forty (40) and ninety (90) hours. For example, as shown in FIG. 4A, the growth rates of the 2×GG36 and 2×GG36 Phbs-yvmA cells are not significantly different, demonstrating that yvmA over-expression from the hbs promoter (Phbs) does not adversely affect the growth rate of *Bacillus* (cells) strains expressing two copies of an exemplary POI, e.g., an alkaline serine protease. As described in Example 6, Applicant also assessed the influence of yvmA over-expression on protease production (i.e., via activity), which results demonstrated no significant negative affect of yvmA overexpression on protease production (FIG. 4B). The amount of pulcherrimin produced by the *Bacillus* cells constructed Example 4 (i.e., 2×GG36 and the 2×GG36 Phbs-yvyD) was quantified as set forth in Example 7. For example, as shown in FIG. 4C, the 2×GG36 Phbs-yvmA cells produced significantly less pulcherrimin than the 2×GG36 cells, demonstrating that over-expressing yvmA renders such *Bacillus* cells (strains) deficient in the production of red pigment (pulcherrimin).

Figure 5A:
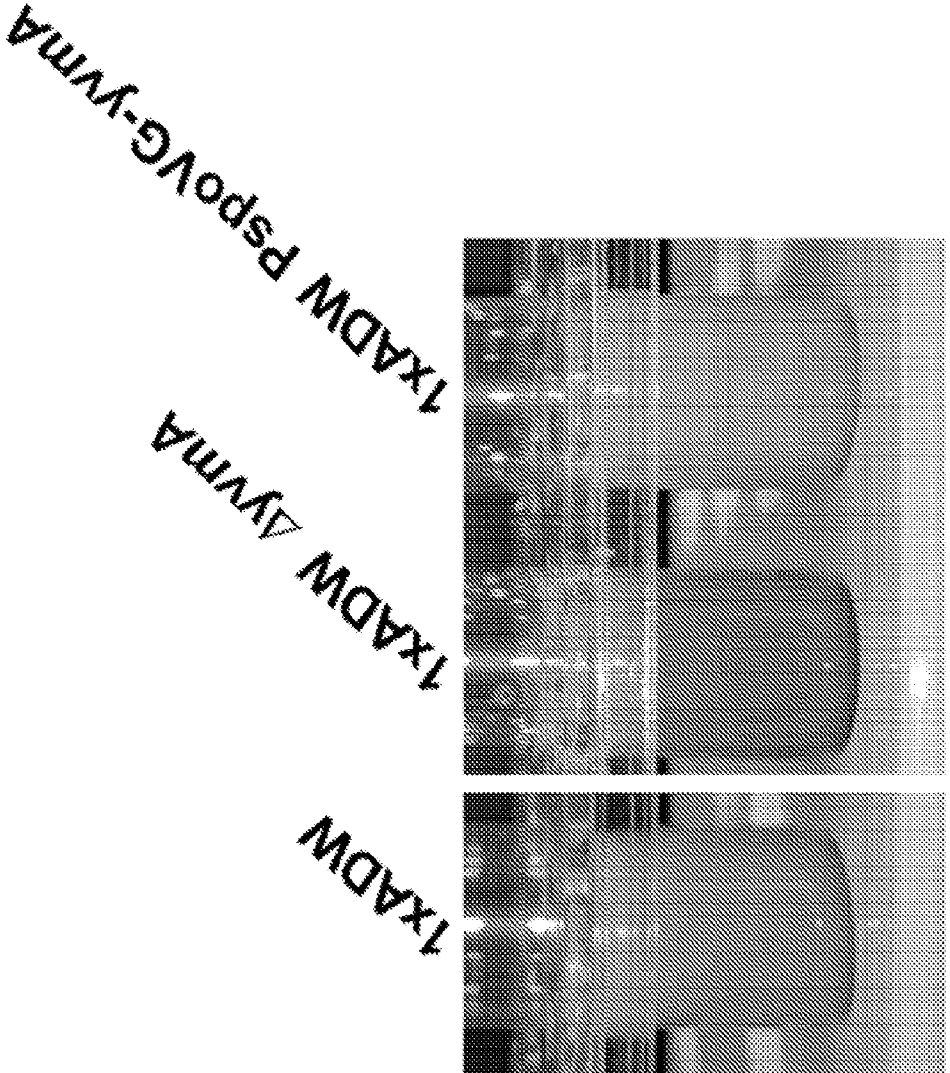
FIG. 5A shows digital images of *B. subtilis* strains grown/fermented in maltrin-based media for forty-eight (48) hours at 37° C., wherein the strains include (left to right) a *B. subtilis* 1×GG36 (parental) strain, a *B. subtilis* 1×GG36 (modified) strain comprising a deletion of the yvmA gene (ΔyvmA) and a *B. subtilis* 1×GG36 (modified) strain overexpressing the yvmA gene (PspoVG-yvmA).
Figure 5B:
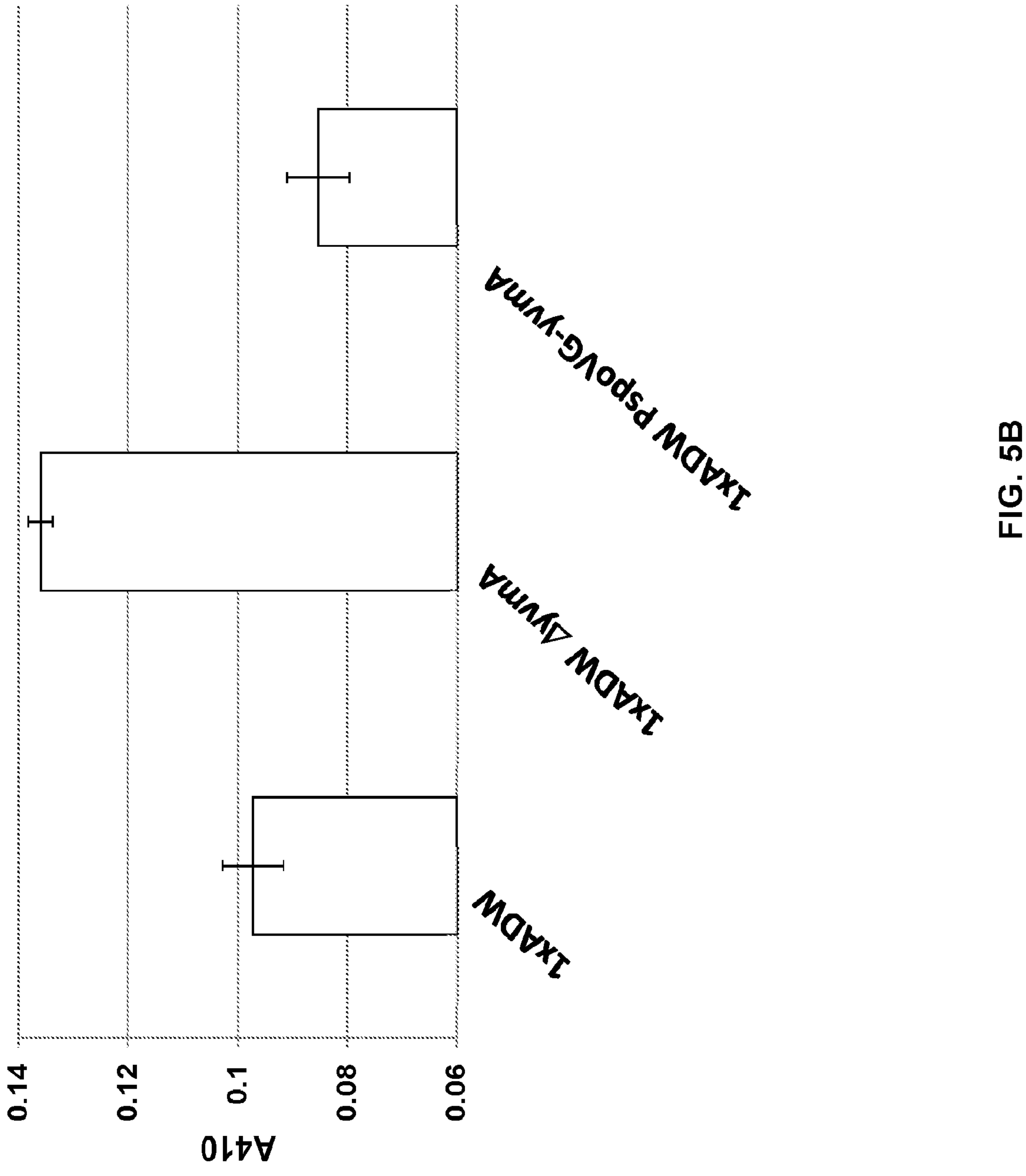
FIG. 5B presents histograms showing the results of quantification (n=3) of the pulcherrimin produced after forty-eight (48) hours of fermentation of the *B. subtilis* 1×GG36, 1×GG36 ΔyvmA and 1×GG36 PspoVG-yvmA strains described in FIG. 5A.

To further validate the observations described above, and to better understand YvmA protein function, Applicant disrupted the yvmA locus (ΔyvmA; Example 8). For example, the 1×GG36 and 1×GG36 PspoVG-yvmA cells (Example 2) and the 1×GG36 ΔyvmA cells were grown as described (Example 8). As shown in FIG. 5A, after forty-eight (48) hours of growth, the color of the yvmA disrupted cells (1×GG36 ΔyvmA) were more visibly red/brown than the parental cells (1×GG36) and/or the yvmA over-expression cells (1×GG36 PspoVG-yvmA). In addition, the yvmA over-expression cells (1×GG36 PspoVG-yvmA) produced less red/brown broth color relative to the parental (1×GG36) cells (FIG. 5A). As shown in FIG. 5B, the pulcherrimin quantification assay also demonstrates that the yvmA disrupted cells (1×GG36 ΔyvmA) produced more pulcherrimin as compared to the parental cells (1×GG36) and/or the yvmA over-expression cells (1×GG36 PspoVG-yvmA).

In certain other embodiments, Applicant has contemplated chemical means to control/mitigate red pigment (pulcherrimin) formation is such *Bacillus* fermentation processes. More particularly, to test this hypothesis, the high pulcherrimin producing yvmA disrupted strain (1×GG36 ΔyvmA; Example 8), was co-fermented with increasing amounts of aluminum chloride ($AlCl_3$). For example, as presented in FIG. 6A, after twenty (20) hours of growth, a reduction in the red/brown color in the fermentation broth was visible, wherein the reduction of red/brown color was more apparent after fifty (50) hours. As shown in FIG. 6B (see; left axis), the relative luminance of these cultures was determined, wherein the luminance increases (positively) correlate with concentrations of aluminum chloride [$AlCl_3$] pre-addition to the 1×GG36 ΔyvmA strain fermentations at the fifty (50) hour timepoint. In addition, aliquots of the 1×GG36 ΔyvmA strain with pre-addition of aluminum chloride ($AlCl_3$) were taken at the fifty (50) hour time point, wherein the relative amount of pulcherrimin in these samples was determined (FIG. 6B; right axis). As depicted in FIG. 6C, pre-addition of aluminum chloride ($AlCl_3$) to a *Bacillus* fermentation (e.g., 1×GG36 ΔyvmA) does not affect the growth rate of the *Bacillus* cells (Example 10), and as shown in FIG. 6D, pre-addition of at least ten (10) mM $AlCl_3$ does not significantly affect the amount of the POI produced during growth/cultivation/fermentation of such *Bacillus* cells (strains).

Figure 7:
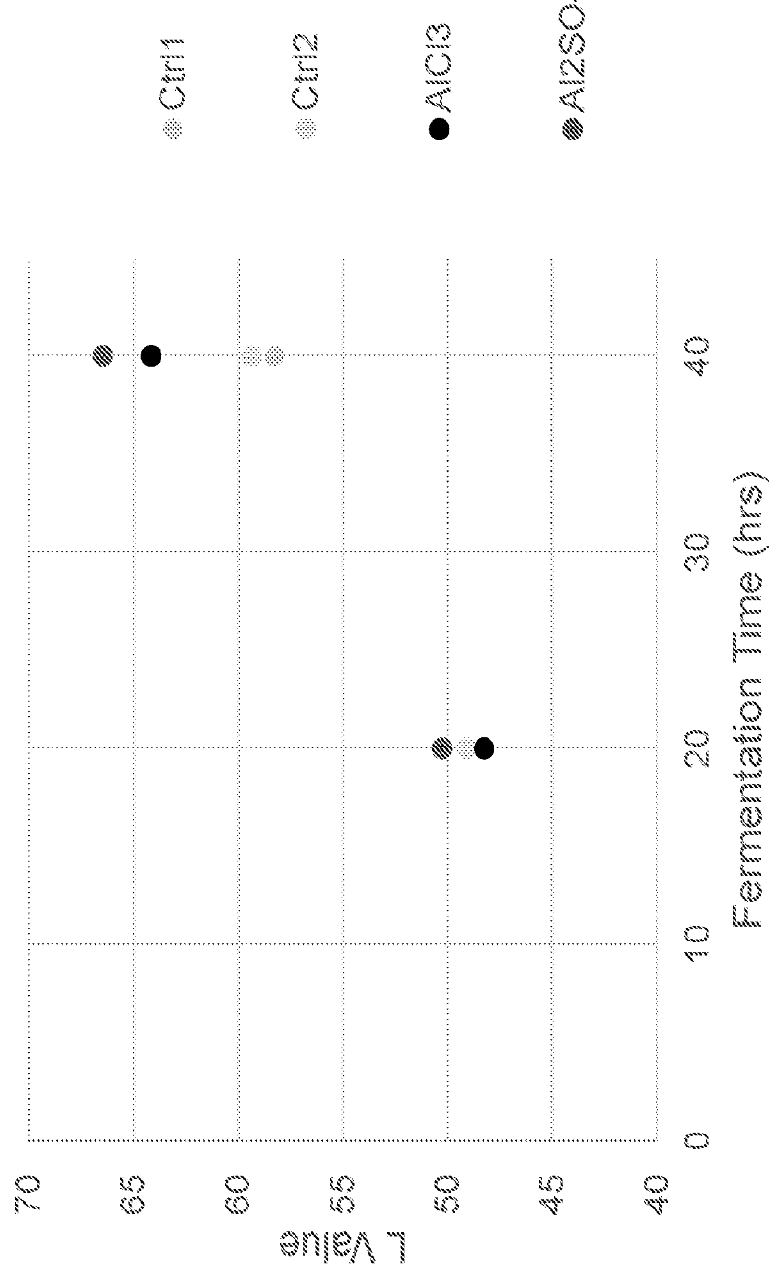
FIG. 7 is a LAB (L) plot of four (4) independent 2-L bioreactor fermentations.

In other embodiments, Applicant constructed *Bacillus licheniformis* strains expressing the *B. subtilis* YvmA protein (SEQ ID NO: 30). More particularly, as described in Example 12, *B. licheniformis* strains were constructed to express functional *B. subtilis* YvmA protein (SEQ ID NO: 30) under the control of heterologous promoters (hbs promoter, spoVG promoter). For example, two (2) independent isolates with the correct sequence for amyL::[Phbs-yvmA tetR] (SEQ ID NO: 33) were stored as strains BF1175 and BF1176; and two (2) independent isolates with the correct sequence for amyL::[PspoVG-yvmA tetR] (SEQ ID NO: 40) were stored as strains BF1177 and BF1178 (Example 12; TABLE 5). Applicant further assessed the amount of pulcherrimin produced by *B. licheniformis* cells expressing the *B. subtilis* YvmA protein (Example 12), by extracting the sodium salt of pulcherrimin from the whole broth culture of the cells (Example 13). As described in Example 13 (TABLE 6), the expression of the *B. subtilis* YvmA protein in *B. licheniformis* from either of two (2) heterologous promoters (Phbs and PspoVG) reduces the amount of pulcherrimin present outside the cells by more than 50% in all cases tested, suggesting that the use of the *B. subtilis* YvmA protein (or a homologue thereof) to reduce, mitigate or otherwise eliminate pulcherrimin (red pigment) production and/or formation can be used in a broad spectrum of bacterial species that produce this compound. The *B. subtilis* strains constructed and described (Example 12) were further assessed by fermentation in two (2) L bioreactors (Example 13; FIG. 7 and TABLE 7) to determine if the red/brown color reducing benefit of the aluminum ion observed in the examples above extend to other bacterial cells/strains at more industrially relevant conditions (e.g., increased bioreactor volumes, higher cell densities, etc.). Additionally, as described in the examples below, the pre-addition of either $AlCl_3$ or $Al_2(SO_4)3$ does not affect the growth rate of the *B. subtilis* cells when fermented in 2 L bioreactors (Example 15), nor does the pre-addition of $AlCl_3$ or $Al_2(SO_4)_3$ affect the protein productivity of the *B. licheniformis* strains fermented in 2 L bioreactors (Example 16).

Thus, as generally described above, *Bacillus* cells expressing the *B. subtilis* yvmA gene (ORF) are deficient in the production of the red pigment (pulcherrimin), whereas *Bacillus* cells having a disruption of yvmA (ΔyvmA) produce increased levels of the red pigment (pulcherrimin) in the fermentation broth. Therefore, in certain embodiments, a yvmA gene (or ORF thereof) of the disclosure is a homologue of the *B. subtilis* yvmA gene (SEQ ID NO: 37) encoding a functional YvmA protein. For example, as briefly set forth above, the YvmA proteins is a member of Major Facilitator Superfamily (MFS) of transporter proteins. As generally described in Pao et al. (1998), the MFS transporters are single-polypeptide secondary carriers capable only of transporting small solutes in response to chemiosmotic ion gradients, which function as uniporters, symporters or antiporters. In addition, the MFS proteins contain twelve (12) transmembrane (TM) regions. Thus, in certain embodiments, the disclosure is related to a yvmA gene (ORF) homologue of the *B. subtilis* yvmA gene. Certain other embodiments are therefore related to a yvmA gene (ORF) homologue encoding a *Bacillus* YvmA protein (homologue) comprising substantial sequence identity to the *B. subtilis* YvmA protein of SEQ ID NO: 30. In certain other embodiments, the *Bacillus* YvmA protein (homologue) comprises twelve (12) transmembrane (TM) regions (i.e., a common characteristic of MFS transporters). For example, in certain embodiments, a yvmA gene (ORF) homologue encodes a *Bacillus* YvmA protein (homologue) comprising substantial sequence identity to the *B. subtilis* YvmA protein of SEQ ID NO: 30 and having twelve (12) transmembrane (TM) domains.

In certain other embodiments, the disclosure is related to *Bacillus* cells comprising a deletion or disruption of the yvmA gene. More particularly, as generally known in the art, the production of pulcherrimin is a technique used by some eukaryotes and prokaryotes to antagonize the growth of competitive organisms by the sequestration of environmental iron ($Fe^{III}$) (Sipiczki, 2020). For example, the production of pulcherriminic acid/pulcherrimin is an area of active interest and research due to its antimicrobial properties (Li et al., 2017). The concept of using pulcherrimin producing organisms for biological control is therefore an area of current research (Pawlikowska et al., 2019), wherein yeast from the *Metschnikowia* genus are known to strongly antagonize the growth of molds from the genera *Alternaria, Botrytis, Fusarium, Rhizopus* and *Verticillum.*

Therefore, in certain embodiments, the disclosure is related to modified *Bacillus* cells comprising a deletion or disruption of the yvmA gene, wherein the modified cells produce increased amounts of pulcherriminic acid/pulcherrimin More particularly, as described in the Examples section, the modified *Bacillus* sp. cells having a deletion of yvmA produce increased amounts of pulcherrimin, as detected in the growth media (e.g., see, FIG. 5A and FIG. 5B). As contemplated herein, such modified *Bacillus* cells of the disclosure are particularly suitable for use as biological control agents. For example, as understood by one of skill in the art, most *Bacillus* sp. cells have obtained the "Qualified Presumption of Safety" (QPS) status of the European Food Safety Authority, and many of their products have obtained a "Generally Recognized As Safe" (GRAS) status from the US Food and Drug Administration, rendering such *Bacillus* sp. cells (i.e., producing increased amounts of pulcherriminic acid/pulcherrimin) particularly useful in such biocontrol applications. Thus, in certain embodiments, the disclosure is related to methods and compositions for constructing modified *Bacillus* cells producing increased amounts of pulcherriminic acid/pulcherrimin Certain other embodiments are therefore related to the use of such modified *Bacillus* cells (i.e., producing increased amounts of pulcherriminic acid/pulcherrimin) to antagonize the growth of undesirable microorganisms. Other embodiments are related to a cultivation/fermentation media (broth) comprising increased amounts of pulcherriminic acid/pulcherrimin obtained by cultivating/fermented a modified *Bacillus* cell of the disclosure (i.e., comprising a deleted or disrupted yvmA gene). Other embodiments are related to biocontrol compositions and methods thereof comprising a modified *Bacillus* cell of the disclosure (i.e., producing increased amounts of pulcherriminic acid/pulcherrimin) and/or a cultivation/fermentation broth obtained by cultivating/fermenting a modified *Bacillus* cell described herein under suitable conditions for the increased production of pulcherriminic acid/pulcherrimin.

III. MOLECULAR BIOLOGY

As set forth above, certain embodiments of the disclosure are related to modified (mutant) *Bacillus* cells derived from parental *Bacillus* cells. Thus, certain embodiments are related to compositions and methods for genetically modifying parental *Bacillus* cells (strains) to generate modified *Bacillus* (daughter) cells.

Certain embodiments are therefore related to methods for genetically modifying *Bacillus* cells, including, but not limited to, (a) the introduction, substitution, or removal of one or more nucleotides in a gene (or an ORF thereof), or the introduction, substitution, or removal of one or more nucleotides in a regulatory element required for the transcription or translation of the gene (or ORF thereof), (b) a gene disruption, (c) a gene conversion, (d) a gene deletion, (e) a gene down-regulation, (f) site specific mutagenesis and/or (g) random mutagenesis.

Thus, in certain embodiments, a modified *Bacillus* cell of the disclosure is constructed by reducing or eliminating the expression of a gene set forth above, using methods well known in the art, for example, insertions, disruptions, replacements, or deletions. The portion of the gene to be modified or inactivated may be, for example, the coding region or a regulatory element required for expression of the coding region.

An example of such a regulatory or control sequence may be a promoter sequence or a functional part thereof, (i.e., a part which is sufficient for affecting expression of the nucleic acid sequence). Other control sequences for modification include, but are not limited to, a leader sequence, a propeptide sequence, a signal sequence, a transcription terminator, a transcriptional activator and the like.

In certain other embodiments a modified *Bacillus* cell is constructed by gene deletion to eliminate or reduce the expression of at least one of the aforementioned genes of the disclosure. Gene deletion techniques enable the partial or complete removal of the gene(s), thereby eliminating their expression, or expressing a non-functional (or reduced activity) protein product. In such methods, the deletion of the gene(s) may be accomplished by homologous recombination using a plasmid that has been constructed to contiguously contain the 5' and 3' regions flanking the gene. The contiguous 5' and 3' regions may be introduced into a *Bacillus* cell, for example, on a temperature-sensitive plasmid, such as pE194, in association with a second selectable marker at a permissive temperature to allow the plasmid to become established in the cell. The cell is then shifted to a non-permissive temperature to select for cells that have the plasmid integrated into the chromosome at one of the homologous flanking regions. Selection for integration of the plasmid is effected by selection for the second selectable marker. After integration, a recombination event at the second homologous flanking region is stimulated by shifting the cells to the permissive temperature for several generations without selection. The cells are plated to obtain single colonies and the colonies are examined for loss of both selectable markers (see, e.g., Perego, 1993). Thus, a person of skill in the art (e.g., by reference to the (nucleic acid) sequences and the encoded protein sequences thereof), may readily identify nucleotide regions in the gene's coding sequence and/or the gene's non-coding sequence suitable for complete or partial deletion.

In other embodiments, a modified *Bacillus* cell of the disclosure is constructed by introducing, substituting, or removing one or more nucleotides in the gene or a regulatory element required for the transcription or translation thereof. For example, nucleotides may be inserted or removed so as to result in the introduction of a stop codon, the removal of the start codon, or a frame-shift of the open reading frame. Such a modification may be accomplished by site-directed mutagenesis or PCR generated mutagenesis in accordance with methods known in the art (e.g., see, Botstein and Shortle, 1985; Lo et al., 1985; Higuchi et al., 1988; Shimada, 1996; Ho et al., 1989; Horton et al., 1989 and Sarkar and Sommer, 1990). Thus, in certain embodiments, a gene of the disclosure is inactivated by complete or partial deletion.

In another embodiment, a modified *Bacillus* cell is constructed by the process of gene conversion (e.g., see Iglesias and Trautner, 1983). For example, in the gene conversion method, a nucleic acid sequence corresponding to the gene(s) is mutagenized in vitro to produce a defective nucleic acid sequence, which is then transformed into the parental *Bacillus* cell to produce a defective gene. By homologous recombination, the defective nucleic acid sequence replaces the endogenous gene. It may be desirable that the defective gene or gene fragment also encodes a marker which may be used for selection of transformants containing the defective gene. For example, the defective gene may be introduced on a non-replicating or temperature-sensitive plasmid in association with a selectable marker. Selection for integration of the plasmid is effected by selection for the marker under conditions not permitting plasmid replication. Selection for a second recombination event leading to gene replacement is effected by examination of colonies for loss of the selectable marker and acquisition of the mutated gene (Perego, 1993). Alternatively, the defective nucleic acid sequence may contain an insertion, substitution, or deletion of one or more nucleotides of the gene, as described below.

In other embodiments, a modified *Bacillus* cell is constructed by established anti-sense techniques using a nucleotide sequence complementary to the nucleic acid sequence of the gene (Parish and Stoker, 1997). More specifically, expression of the gene by a *Bacillus* cell may be reduced (down-regulated) or eliminated by introducing a nucleotide sequence complementary to the nucleic acid sequence of the gene, which may be transcribed in the cell and is capable of hybridizing to the mRNA produced in the cell. Under conditions allowing the complementary anti-sense nucleotide sequence to hybridize to the mRNA, the amount of protein translated is thus reduced or eliminated. Such anti-sense methods include, but are not limited to RNA interference (RNAi), small interfering RNA (siRNA), microRNA (miRNA), antisense oligonucleotides, and the like, all of which are well known to the skilled artisan.

In other embodiments, a modified *Bacillus* cell is produced/constructed via CRISPR-Cas9 editing. For example, a gene can be disrupted (or deleted or down-regulated) by means of nucleic acid guided endonucleases, that find their target DNA by binding either a guide RNA (e.g., Cas9) and Cpfl or a guide DNA (e.g., NgAgo), which recruits the endonuclease to the target sequence on the DNA, wherein the endonuclease can generate a single or double stranded break in the DNA. This targeted DNA break becomes a substrate for DNA repair, and can recombine with a provided editing template to disrupt or delete the gene. For example, the gene encoding the nucleic acid guided endonuclease (for this purpose Cas9 from *S. pyogenes*) or a codon optimized gene encoding the Cas9 nuclease is operably linked to a promoter active in the *Bacillus* cell and a terminator active in *Bacillus* cell, thereby creating a *Bacillus* Cas9 expression cassette. Likewise, one or more target sites unique to the gene of interest are readily identified by a person skilled in the art. For example, to build a DNA construct encoding a gRNA-directed to a target site within the gene of interest using *Streptococcus pyogenes* Cas9, the variable targeting domain (VT) will comprise nucleotides of the target site which are 5' of the (PAM) proto-spacer adjacent motif (NGG), which nucleotides are fused to DNA encoding the Cas9 endonuclease recognition domain for *S. pyogenes* Cas9 (CER). The combination of the DNA encoding a VT domain and the DNA encoding the CER domain thereby generate a DNA encoding a gRNA. Thus, a *Bacillus* expression cassette for the gRNA is created by operably linking the DNA encoding the gRNA to a promoter active in *Bacillus* cells and a terminator active in *Bacillus* cells.

In certain embodiments, the DNA break induced by the endonuclease is repaired/replaced with an incoming sequence. For example, to precisely repair the DNA break generated by the Cas9 expression cassette and the gRNA expression cassette described above, a nucleotide editing template is provided, such that the DNA repair machinery of the cell can utilize the editing template. For example, about 500-bp 5' of targeted gene can be fused to about 500-bp 3' of the targeted gene to generate an editing template, which template is used by the *Bacillus* host's machinery to repair the DNA break generated by the RGEN.

The Cas9 expression cassette, the gRNA expression cassette and the editing template can be co-delivered to the cells using many different methods. The transformed cells are screened by PCR amplifying the target gene locus, by amplifying the locus with a forward and reverse primer. These primers can amplify the wild-type locus or the modified locus that has been edited by the RGEN.

In yet other embodiments, a modified *Bacillus* cell is constructed by random or specific mutagenesis using methods well known in the art, including, but not limited to, chemical mutagenesis (see, e.g., Hopwood, 1970) and transposition (see, e.g., Youngman et al., 1983). Modification of the gene may be performed by subjecting the parental cell to mutagenesis and screening for mutant cells in which expression of the gene has been reduced or eliminated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosoguanidine (NTG), O-methyl hydroxylamine, nitrous acid, ethyl methane sulphonate (EMS), sodium bisulphite, formic acid, and nucleotide analogues. When such agents are used, the mutagenesis is typically performed by incubating the parental cell to be mutagenized in the presence of the mutagenizing agent of choice under suitable conditions, and selecting for mutant cells exhibiting reduced or no expression of the gene.

International PCT Publication No. WO2003/083125 discloses methods for modifying *Bacillus* cells, such as the creation of *Bacillus* deletion strains and DNA constructs using PCR fusion to bypass *E. coli*. PCT Publication No. WO2002/14490 discloses methods for modifying *Bacillus* cells including (1) the construction and transformation of an integrative plasmid (pComK), (2) random mutagenesis of coding sequences, signal sequences and pro-peptide sequences, (3) homologous recombination, (4) increasing transformation efficiency by adding non-homologous flanks to the transformation DNA, (5) optimizing double cross-over integrations, (6) site directed mutagenesis and (7) marker-less deletion.

Those of skill in the art are well aware of suitable methods for introducing polynucleotide sequences into bacterial cells (e.g., *E. coli* and *Bacillus* sp.) (e.g., Ferrari et al., 1989; Saunders et al., 1984; Hoch et al., 1967; Mann et al., 1986; Holubova, 1985; Chang et al., 1979; Vorobjeva et al., 1980; Smith et al., 1986; Fisher et al., 1981 and McDonald, 1984). Indeed, such methods as transformation including protoplast transformation and congression, transduction, and protoplast fusion are known and suited for use in the present disclosure. Methods of transformation are particularly preferred to introduce a DNA construct of the present disclosure into a host cell.

In addition to commonly used methods, in some embodiments, host cells are directly transformed (i.e., an intermediate cell is not used to amplify, or otherwise process, the DNA construct prior to introduction into the host cell). Introduction of the DNA construct into the host cell includes those physical and chemical methods known in the art to introduce DNA into a host cell, without insertion into a plasmid or vector. Such methods include, but are not limited to, calcium chloride precipitation, electroporation, naked DNA, liposomes and the like. In additional embodiments, DNA constructs are co-transformed with a plasmid without being inserted into the plasmid. In further embodiments, a selective marker is deleted or substantially excised from the modified *Bacillus* strain by methods known in the art (e.g., Stahl et al., 1984; Palmeros et al., 2000). In some embodiments, resolution of the vector from a host chromosome leaves the flanking regions in the chromosome, while removing the indigenous chromosomal region.

Promoters and promoter sequence regions for use in the expression of genes, open reading frames (ORFs) thereof and/or variant sequences thereof in *Bacillus* cells are generally known on one of skill in the art. Promoter sequences of the disclosure are generally chosen so that they are functional in the *Bacillus* cells. Certain exemplary *Bacillus* promoter sequences include, but are not limited to, the *B. subtilis* alkaline protease (aprE) promoter, the α-amylase promoter of *B. subtilis*, the α-amylase promoter of *B. amyloliquefaciens*, the neutral protease (nprE) promoter from *B. subtilis*, a mutant aprE promoter (e.g., PCT Publication No. WO2001/51643) or any other promoter from Bacilli. Methods for screening and creating promoter libraries with a range of activities (promoter strength) in *Bacillus* cells is describe in PCT Publication No. WO2003/089604.

IV. FERMENTING *BACILLUS* CELLS FOR PRODUCTION OF A PROTEIN OF INTEREST

As generally described above, certain embodiments are related to compositions and methods for constructing and obtaining *Bacillus* cells (strains) producing a protein of interest (POI). More particularly, certain embodiments are related to compositions and methods for producing a protein of interest (POI) in pigment deficient *Bacillus* cells. Other embodiments are therefore related to pigment deficient proteins of interest produced by such pigment deficient *Bacillus* cells. Thus, certain embodiments are related to methods of producing proteins of interest in *Bacillus* cells by growing/cultivating/fermenting the cells in a suitable medium. Fermentation methods well known in the art can be applied to ferment the parental and modified (daughter) *Bacillus* cells of the disclosure.

In some embodiments, the cells are cultured under batch or continuous fermentation conditions. A classical batch fermentation is a closed system, where the composition of the medium is set at the beginning of the fermentation and is not altered during the fermentation. At the beginning of the fermentation, the medium is inoculated with the desired organism(s). In this method, fermentation is permitted to occur without the addition of any components to the system. Typically, a batch fermentation qualifies as a "batch" with respect to the addition of the carbon source, and attempts are often made to control factors such as pH and oxygen concentration. The metabolite and biomass compositions of the batch system change constantly up to the time the fermentation is stopped. Within typical batch cultures, cells can progress through a static lag phase to a high growth log phase, and finally to a stationary phase, where growth rate is diminished or halted. If untreated, cells in the stationary phase eventually die. In general, cells in log phase are responsible for the bulk of production of product.

A suitable variation on the standard batch system is the "fed-batch" fermentation system. In this variation of a typical batch system, the substrate is added in increments as the fermentation progresses. Fed-batch systems are useful when catabolite repression likely inhibits the metabolism of the cells and where it is desirable to have limited amounts of substrate in the medium. Measurement of the actual substrate concentration in fed-batch systems is difficult and is therefore estimated on the basis of the changes of measurable factors, such as pH, dissolved oxygen and the partial pressure of waste gases, such as $CO_2$. Batch and fed-batch fermentations are common and known in the art.

Continuous fermentation is an open system where a defined fermentation medium is added continuously to a bioreactor, and an equal amount of conditioned medium is removed simultaneously for processing. Continuous fermentation generally maintains the cultures at a constant high density, where cells are primarily in log phase growth. Continuous fermentation allows for the modulation of one or more factors that affect cell growth and/or product concentration. For example, in one embodiment, a limiting nutrient, such as the carbon source or nitrogen source, is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

In certain embodiments, a protein of interest expressed/produced by a *Bacillus* cell of the disclosure may be recovered from the culture medium by conventional procedures including separating the host cells from the medium by centrifugation or filtration, or if necessary, disrupting the cells and removing the supernatant from the cellular fraction and debris. Typically, after clarification, the proteinaceous components of the supernatant or filtrate are precipitated by means of a salt, e g, ammonium sulfate. The precipitated proteins are then solubilized and may be purified by a variety of chromatographic procedures, e.g., ion exchange chromatography, gel filtration.

V. PROTEINS OF INTEREST

A protein of interest (POI) of the instant disclosure can be any endogenous protein or heterologous protein, and it may be a variant of such a POI. The protein can contain one or more disulfide bridges or is a protein whose functional form is a monomer or a multimer, i.e., the protein has a quaternary structure and is composed of a plurality of identical (homologous) or non-identical (heterologous) subunits, wherein the POI or a variant POI thereof is preferably one with properties of interest.

In certain preferred embodiments, the modified *Bacillus* cell is deficient in the production of the red pigment (as described above), such that a POI produced and isolated therefrom is deficient in the red pigment (pulcherrimin), i.e., relative to its unmodified (parental) cell.

In certain embodiments, specific productivity (Qp) of a POI relative the (unmodified) parental cell may be assessed. For example, the detection of specific productivity (Qp) is a suitable method for evaluating protein production. The specific productivity (Qp) can be determined using the following equation:

$$\text{“}Qp=gP/gDCW\cdot hr\text{”}$$

wherein, "gP" is grams of protein produced in the tank; "gDCW" is grams of dry cell weight (DCW) in the tank and "hr" is fermentation time in hours from the time of inoculation, which includes the time of production as well as growth time.

In certain embodiments, a POI or a variant POI thereof is selected from the group consisting of acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, ligases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof.

Thus, in certain embodiments, a POI or a variant POI thereof is an enzyme selected from Enzyme Commission (EC) Number EC 1, EC 2, EC 3, EC 4, EC 5 or EC 6.

In certain other embodiments, a modified *Bacillus* cell of the disclosure comprises an expression construct encoding an amylase. A wide variety of amylase enzymes and variants thereof are known to one skilled in the art. For example, International PCT Publication NO. WO2006/037484 and WO 2006/037483 describe variant α-amylases having improved solvent stability, PCT Publication No. WO1994/18314 discloses oxidatively stable α-amylase variants, PCT Publication No. WO1999/19467, WO2000/29560 and WO2000/60059 disclose Termamyl-like α-amylase variants, PCT Publication No. WO2008/112459 discloses α-amylase variants derived from *Bacillus* sp. number 707, PCT Publication No. WO1999/43794 discloses maltogenic α-amylase variants, PCT Publication No. WO1990/11352 discloses hyper-thermostable α-amylase variants, PCT Publication No. WO2006/089107 discloses α-amylase variants having granular starch hydrolyzing activity, and the like.

There are various assays known to those of ordinary skill in the art for detecting and measuring activity of intracellularly and extracellularly expressed proteins.

PCT Publication No. WO2014/164777 discloses Ceralpha α-amylase activity assays useful for detecting amylase activities described herein.

In certain other embodiments, a modified *Bacillus* cell of the disclosure comprises an expression construct encoding a protease. A wide variety of protease enzymes and variants thereof are known to one skilled in the art. For example, suitable proteases may be derived from *Bacillus lentus* (PCT Publication Nos. WO2011/140316 and WO2012/151534), *Bacillus licheniformis* (PCT Publication No. WO2016/183509; US Publication No. US2020/0123522), *Bacillus gibsonii* (PCT Publication Nos. WO2003/054185; WO2015/089447; WO2020/242858), *Bacillus amyloliquefaciens* (U.S. Pat. No. 5,972,682), *Bacillus clausii* (WO2010/056634), *Geobacillus* (WO2009/058303), *Bacillus pumilus* (WO2007/131656), a *Bacillus* sp. TY-145 protease (WO2015/014803) and the like.

V. EXEMPLARY EMBODIMENTS

Non-limiting embodiments of compositions and methods disclosed herein are as follows:

1. A modified *Bacillus* cell derived from a parental *Bacillus* cell, wherein the modified cell comprises an introduced yvmA expression cassette encoding a functional YvmA protein, wherein the modified cell is deficient in the production of a red pigment relative to the parental cell when grown (cultivated) under the same conditions.
2. A modified *Bacillus* cell derived from a parental *Bacillus* cell comprising a yvmA gene encoding a functional YvmA protein, wherein the modified cell comprises a genetic modification which replaces the native promoter (sequence) of the yvmA gene with a heterologous promoter (sequence) capable of increasing expression of the yvmA gene relative to the native promoter of the yvmA gene, wherein the modified cell is deficient in the production of a red pigment relative to the parental cell when grown (cultivated) under the same conditions.
3. The *Bacillus* cell of embodiment 1, wherein the introduced expression cassette comprises an open reading frame (ORF) sequence encoding a functional YvmA protein comprising at least 85% sequence identity to the *B. subtilis* YvmA protein of SEQ ID NO: 30, or a *Bacillus* sp. YvmA homologue thereof.
4. The *Bacillus* cell of embodiment 1, wherein the introduced expression cassette comprises an ORF sequence comprising at least 90% sequence identity to the *B. subtilis* yvmA ORF of SEQ ID NO: 37, or a *Bacillus* sp. yvmA homologue thereof, encoding a functional YvmA protein.
5. The *Bacillus* cell of embodiment 1 or embodiment 2, further comprising a genetic modification which mutates, disrupts, partially deletes, or completely deletes a *Bacillus* gene selected from the group consisting of cypX, yvmC and yvmB.
6. The *Bacillus* cell of embodiment 1 or embodiment 2, selected from the group consisting of *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulars, B. lautus* and *B. thuringiensis.*
7. The *Bacillus* cell of embodiment 1 or embodiment 2, wherein the functional YvmA protein is involved in the production of the red pigment.
8. The *Bacillus* cell of embodiment 1 or embodiment 2, wherein the red pigment is pulcherrimin
9. The *Bacillus* cell of embodiment 1 or embodiment 2, wherein the modified cell comprises an equivalent or enhanced growth rate relative to the parental cell.
10. A modified *Bacillus* cell derived from a parental *Bacillus* cell producing a protein of interest (POI), wherein the modified cell comprises an introduced yvmA expression cassette encoding a functional YvmA protein, wherein the modified cell is deficient in the production of a red pigment relative to the parental cell when fermented (cultivated) under the same conditions.
11. A modified *Bacillus* cell derived from a parental *Bacillus* cell producing a protein of interest (POI) and comprising a yvmA gene encoding a functional YvmA protein, wherein the modified cell comprises a genetic modification which replaces the native promoter (sequence) of the yvmA gene with a heterologous promoter (sequence) capable of increasing expression of the yvmA gene relative to the native promoter (sequence) of the yvmA gene, wherein the modified cell is deficient in the production of a red pigment relative to the parental cell when fermented (cultivated) under the same conditions.
12. The *Bacillus* cell of embodiment 10 or embodiment 11, wherein the POI is an endogenous POI or a heterologous POI.
13. The *Bacillus* cell of embodiment 10 or embodiment 11, wherein the POI is an enzyme.

14. The *Bacillus* cell of embodiment 13, wherein the enzyme is selected from the group consisting of acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, polyesterases, α-galactosidases, β-galactosidases, α-glucanases, glucan lysases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transglutaminases, xylanases, hexose oxidases, and combinations thereof.
15. The *Bacillus* cell of embodiment 10, wherein the introduced expression cassette comprises an open reading frame (ORF) sequence encoding a functional YvmA protein comprising at least 85% sequence identity to the *B. subtilis* YvmA protein of SEQ ID NO: 30, or a *Bacillus* sp. YvmA homologue thereof.
16. The *Bacillus* cell of embodiment 10, wherein the introduced expression cassette comprises an ORF sequence comprising at least 90% sequence identity to the *B. subtilis* yvmA ORF of SEQ ID NO: 37, or a *Bacillus* sp. yvmA homologue thereof, encoding a functional YvmA protein.
17. The *Bacillus* cell of embodiment 10 or embodiment 11, further comprising a genetic modification which mutates, disrupts, partially deletes, or completely deletes a *Bacillus* gene selected from the group consisting of cypX, yvmC and yvmB.
18. The *Bacillus* cell of embodiment 10 or embodiment 11, selected from the group consisting of *B. subtilis, B. lichenifonnis, B. lentus, B. brevis, B. stearothermophilus, B. alkalophilus, B. amyloliquefaciens, B. clausii, B. halodurans, B. megaterium, B. coagulans, B. circulars, B. lautus* and *B. thuringiensis.*
19. The *Bacillus* cell of embodiment 10 or embodiment 11, wherein the functional YvmA protein is involved in the production of the red pigment.
20. The *Bacillus* cell of embodiment 10 or embodiment 11, wherein the red pigment is pulcherrimin
21. The *Bacillus* cell of embodiment 10 or embodiment 11, wherein the modified cell comprises an equivalent or enhanced growth rate relative to the parental cell.
22. The *Bacillus* cell of embodiment 10 or embodiment 11, wherein the modified cell produces an equivalent or enhanced amount of the POI relative to the parental cell.
23. An isolated protein of interest (POI) produced by the modified *Bacillus* cell of embodiment 10 or embodiment 11.
24. The isolated POI of embodiment 23, comprising no observable red pigment.
25. A method for growing (cultivating) a *Bacillus* cell deficient in the production of a red pigment comprising (a) modifying a parental *Bacillus* cell by introducing therein an expression cassette encoding a functional YvmA protein, and (b) growing the modified cell under suitable conditions, wherein the modified cell is deficient in the production of a red pigment relative to the parental cell when grown under the same conditions.
26. A method for growing (cultivating) a *Bacillus* cell deficient in the production of a red pigment comprising (a) obtaining a parental *Bacillus* cell comprising a yvmA gene encoding a functional YvmA protein and replacing the native promoter (sequence) of the yvmA gene with a heterologous promoter (sequence) capable of increasing expression of the yvmA gene relative to the native promoter of the yvmA gene, and (b) growing the modified cell under suitable conditions, wherein the modified cell is deficient in the production of a red pigment relative to the parental cell when grown under the same conditions.
27. A method for producing an endogenous protein of interest (POI) comprising (a) obtaining a parental *Bacillus* cell producing an endogenous POI and modifying the cell by introducing therein an expression cassette encoding a functional YvmA protein, and (b) fermenting the modified cell under suitable conditions for the production of the POI, wherein the modified cell is deficient in the production of a red pigment relative to the parental cell when fermented under the same conditions.
28. A method for producing an endogenous protein of interest (POI) comprising (a) obtaining a parental *Bacillus* cell producing an endogenous POI and comprising a yvmA gene encoding a functional YvmA protein and genetically modifying the cell by replacing the native promoter (sequence) of the yvmA gene with a heterologous promoter (sequence) capable of increasing expression of the yvmA gene relative to the native promoter of the yvmA gene and (b) fermenting the modified cell under suitable conditions for the production of the POI, wherein the modified cell is deficient in the production of a red pigment relative to the parental cell when fermented under the same conditions.
29. A method for producing a heterologous protein of interest (POI) comprising (a) modifying a parental *Bacillus* cell comprising a yvmA gene encoding a functional YvmA protein by introducing therein (i) an expression cassette encoding a heterologous POI and (ii) an expression cassette encoding a functional YvmA protein and (b) fermenting the modified cell under suitable conditions for the production of the POI, wherein the modified cell is deficient in the production of a red pigment relative to the parental cell when fermented under the same conditions.
30. A method for producing a heterologous protein of interest (POI) comprising (a) modifying a parental *Bacillus* cell comprising a yvmA gene encoding a functional YvmA protein by introducing therein an expression cassette encoding a POI and replacing therein the native promoter (sequence) of the yvmA gene with a heterologous promoter (sequence) capable of increasing expression of the yvmA gene relative to the native promoter of the yvmA gene and (b) fermenting the modified cell under suitable conditions for the production of the POI, wherein the modified cell is deficient in the production of a red pigment relative to the parental cell when fermented under the same conditions.
31. The method of any one of embodiments 27-30, wherein the POI is an enzyme.
32. The method of embodiment 31, wherein the enzyme is selected from the group consisting of acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, polyesterases, α-galactosidases, β-galactosidases, α-glucanases, glucan lysases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transglutaminases, xylanases, hexose oxidases, and combinations thereof.

33. The method of any one of embodiments 25, 27, or 29, wherein the introduced expression cassette comprises an open reading frame (ORF) sequence encoding a functional YvmA protein comprising at least 85% sequence identity to the *B. subtilis* YvmA protein of SEQ ID NO: 30, or a *Bacillus* sp. YvmA homologue thereof.

34. The method of any one of embodiments 25, 27, or 29, wherein the introduced expression cassette comprises an ORF sequence comprising at least 90% sequence identity to the *B. subtilis* yvmA ORF of SEQ ID NO: 37, or a *Bacillus* sp. yvmA homologue thereof, encoding a functional YvmA protein.

35. The method of any one of embodiments 25-30, wherein the modified cell further comprising a genetic modification which mutates, disrupts, partially deletes, or completely deletes a *Bacillus* gene selected from the group consisting of cypX, yvmC and yvmB.

36. The method of any one of embodiments 25-30, wherein the *Bacillus* cell is selected from the group consisting of *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulars, B. lautus* and *B. thuringiensis.*

37. The method of any one of embodiments 25-30, wherein the functional YvmA protein involved in the production of the red pigment.

38. The method of any one of embodiments 25-30, wherein the red pigment is pulcherrimin 39. The method of any one of embodiments 25-30, wherein the modified cell comprises an equivalent or enhanced growth rate relative to the parental cell.

40. The method of any one of embodiments 25-30, wherein the modified cell produces an equivalent or enhanced amount of the POI relative to the parental cell.

41. An isolated protein of interest (POI) produced by the method of any one of embodiments 25-30.

42. The isolated POI of embodiment 41, comprising no observable red pigment.

43. A method to mitigate red pigment color in a *Bacillus* fermentation broth comprising fermenting a *Bacillus* cell producing a protein of interest in the presence of an aluminum ion.

44. The method of embodiment 34, wherein the aluminum ion is provided in the form of $AlCl_3$ or $Al_2(SO_4)3$.

EXAMPLES

Certain aspects of the present invention may be further understood in light of the following examples, which should not be construed as limiting. Modifications to materials and methods will be apparent to those skilled in the art.

Example 1

Construction of yvmA Over-Expression Integration Cassettes

The present example describes the construction of yvmA (gene) over-expression (integration) cassettes (e.g., see FIG. 1). More particularly, the yvmA over-expression cassettes described herein were generated by NEBuilder (New England Biolabs) via assembly of PCR amplified DNA fragments. For example, the integration cassette fragments were designed to integrate at the spoIIIAE locus, wherein the spoIIIAE flanking sequences were amplified from *Bacillus subtilis* (e.g., *Bacillus subtilis* strain 168, ATCC 23857) genomic DNA. Thus, as generally set forth below in TABLE 1, the upstream (5') spoIIIAE flanking region was amplified with oligonucleotide primers 265 (SEQ ID NO: 1) and 117 (SEQ ID NO: 2), and the downstream (3') spoIIIAE flanking region was amplified with oligonucleotide primers 245 (SEQ ID NO: 3) and 266 (SEQ ID NO: 4).

A DNA fragment with the spectinomycin antibiotic resistance marker (SpecR) flanked by loxP sites was amplified using oligonucleotide primers 247 (TABLE 1; SEQ ID NO: 5) and 55 (TABLE 1; SEQ ID NO: 6). The spoVG promoter (PspoVG) region was amplified using oligonucleotide primers 124 (TABLE 1; SEQ ID NO: 7) and 401 (TABLE 1; SEQ ID NO: 8). The thirty-six (36) base pairs (bp) of the spoVG promoter region adjacent to the spoVG open reading frame (ORF) that encompassed the Shine-Dalgarno sequence were included adjacent to the promoter regions of the Phbs-yvmA (SEQ ID NO: 19), Pyvyd-yvmA (SEQ ID NO: 20) and PpstS-yvmA (SEQ ID NO: 21) integration cassettes. As presented in TABLE 1, the hbs promoter region (Phbs) and the pstS promoter region (PpstS) were amplified using the following oligonucleotide primer pairs: hbs primers 298 (SEQ ID NO: 9) and 307 (SEQ ID NO: 10) and pstS primers 305 (SEQ ID NO: 11) and 308 (SEQ ID NO: 12). The yvmA ORF (SEQ ID NO: 37) was amplified from *B. subtilis* genomic DNA with oligonucleotide primers 131 (SEQ ID NO: 13) and 129 (SEQ ID NO: 14) for PspoVG-yvmA assembly, and primers 299 (SEQ ID NO:15) and 129 (SEQ ID NO:14) for Phbs-yvmA assembly, and primers 306 (SEQ ID NO:16) and 129 (SEQ ID NO:14) for PpstS-yvmA assembly. Primers 302 (SEQ ID NO: 17) and 129 (SEQ ID NO:14) were used for assembly of the yvyD promoter region and yvmA ORF. NEBuilder assembly was performed as directed by the manufacturer with the overlapping DNA fragments to generate the complete spoIHAE::PspoVG-yvmA-lox-SpecR-lox, spoIHAE::Phbs-yvmA-lox-SpecR-lox, spoIHAE::PyvyD-yvmA-lox-SpecR-lox and spoIHAE::PpstS-yvmA-lox-SpecR-lox integration cassettes, wherein the complete sequences of the assembled integration cassettes are included for PspoVG-yvmA (SEQ ID NO: 18), Phbs-yvmA (SEQ ID NO: 19), PyvyD-yvmA (SEQ ID NO: 20) and PpstS-yvmA (SEQ ID NO: 21).

TABLE 1

| OLIGONUCLEOTIDE PRIMERS | | |
|---|---|---|
| SEQ ID NO | Primer | Nucleotide Sequence |
| 1 | 265 | CGGGCCCGCCTCCTAGCGG |
| 2 | 117 | CGCTTTTGGCTTCCTCAGGCG |
| 3 | 245 | TAAACCCTTGCATATGTCTAGATAACTTCGTATAATGTATGCTATACGAAGTTAT GCGGCCGCCATATGCATCCTAGGCCCCAAGAGGAGCGGAATGAGCGC |
| 4 | 266 | GGCCGTGCTGATCATAGCAGG |
| 5 | 247 | CGCCAATGTTTTCGCCGCAGAAGCGCACGAAACAAAAAAAGCACCACATGTAAAA AAGCTGCCTTTGCGGGCAGCTTTTTTCGACGGTATCTTATTGCGGATCC |
| 6 | 55 | CTAGACATATGCAAGGGTTTATTGT |
| 7 | 124 | AGGATGAAAGAAGGCAGCAGATACAGCTCCGCCTGAGGAAGCCAAAAGCGTAAGA AAAGTGATTCTGGGAGAGC |
| 8 | 401 | AGTAGTTCACCACCTTTTCCCTATATAAAAG |
| 9 | 298 | ACCGCTCGTGTTCATCAGGAAGAGGATAACAGGATGAAAGAAGGCAGCAGATACA GCTCCGCCTGAGGAAGCCAAAAGCGTAAATCCTTGACGAGCAAGGGATTG |
| 10 | 307 | ATACATTCAGTTCGTTTATTATCATTTC |
| 11 | 305 | ACCGCTCGTGTTCATCAGGAAGAGGATAACAGGATGAAAGAAGGCAGCAGATACA GCTCCGCCTGAGGAAGCCAAAAGCGATATTTTGAGCTGAAATCGAAGCAGG |
| 12 | 308 | GTATAGAGTAAAGGTTCTATGTAAAAAG |
| 13 | 131 | TTCAGAAAAAATCGTGGAATTGATACACTAATGCTTTTATATAGGGAAAAGGTGG TGAACTACTTTGGCTCATACAAAATCAAAGGCAG |
| 14 | 129 | AAAAAGCTGCCCGCAAAGGCAG |
| 15 | 299 | TTGCTCTCATTTTTTTCTGAGACAGGTTTAGAATCAGACTGAACTGTGAAGAAAT GATAATAAACGAACTGAATGTATCCTAATGCTTTTATATAGGGAAAAGGTGG |
| 16 | 306 | TATACAAAAAAACGCACTGATTTACAAAACCTTAACATTCGGTTCAAACCCTTTT TACATAGAACCTTTACTCTATACGTTAATGCTTTTATATAGGGAAAAGGTGG |
| 17 | 302 | ACCGCTCGTGTTCATCAGGAAGAGGATAACAGGATGAAAGAAGGCAGCAGATACA GCTCCGCCTGAGGAAGCCAAAAGCGGATTTATGTTTCAGCAGGAATTGTAAAGGG TAAAAGAGAAATAGATACATTAATGCTTTTATATAGGGAAAAGGTGG |

Example 2

Construction and Generation of *B. subtilis* Strains Expressing yvmA

The instant example generally describes the construction of *B. subtilis* cells (strains) expressing a single (1) copy of a gene (1×GG36) encoding an exemplary GG36 protease and modified (daughter) cells thereof comprising an introduced cassette over-expressing the *B. subtilis* yvmA gene (ORF) of SEQ ID NO: 37. For example, about 1-2 μg of the spoHAE::PspoVG-yvmA-lox-SpecR-lox integration cassette (SEQ ID NO: 18), the spoHAE::Phbs-yvmA-lox-SpecR-lox integration cassette (SEQ ID NO: 19), the spoHAE::PyvyD-yvmA-lox-SpecR-lox integration cassette (SEQ ID NO: 20) and the spoHAE::PpstS-yvmA-lox-SpecR-lox integration cassette (SEQ ID NO: 21) were separately transformed into a comK (competent) *B. subtilis* parental strain that expresses a single (1) copy (1×GG36) of the GG36 protease. More particularly, the transformed cells were plated on LB (1% tryptone, 0.5% yeast extract, 1.0% sodium chloride, 1.5% agar) and one-hundred (100) μg/ml spectinomycin, wherein spectinomycin resistant colonies were purified by re-streaking on LB with one-hundred (100) mg/L spectinomycin. The integration of each cassette at the spoIIIAE locus was confirmed by PCR amplification using Q5 High Fidelity PCR polymerase (NEB) and harvested genomic DNA as template with oligonucleotide primers 241 (SEQ ID NO: 22) and 242 (SEQ ID NO: 23) set forth below in TABLE 2, which primers bind outside of the integration event. Likewise, the correct sequence of each integration cassette was confirmed by Sanger sequencing using oligonucleotides 241 (SEQ ID NO: 22; TABLE 2), 179 (SEQ ID NO: 24; TABLE 2), 129 (SEQ ID NO: 14; TABLE 1), 282 (SEQ ID NO: 25; TABLE 2), 180 (SEQ ID NO: 26; TABLE 2) and 242 (SEQ ID NO: 23; TABLE 2). Additionally, the spectinomycin antibiotic resistant marker (lox-SpecR-lox) was removed by transformation of a plasmid expressing the Cre recombinase. After plasmid loss, spectinomycin sensitive colonies were identified and the integration cassette was amplified with oligonucleotide primers 241 (SEQ ID NO: 22) and 242 (SEQ ID NO: 23). Correct recombination of the lox sites was confirmed for each yvmA expression strains by sequence analysis using oligonucleotide 180 (SEQ ID NO: 26).

TABLE 2

| OLIGONUCLEOTIDE PRIMERS | | |
|---|---|---|
| SEQ ID NO | Primer | Nucleotide Sequence |
| 22 | 241 | GCAAATAGGATAAACAACACGATGG |
| 23 | 242 | CGCCTATATTGCTGAATTCGGGG |
| 24 | 179 | GCGATATTTCTGAGCAGGTTAGC |
| 25 | 282 | ACTCCTGATCCAAACATGTAAGTAC |
| 26 | 180 | TGCCAACGGAAAGCTGCTGGG |
| 27 | 52 | CAGACGGATTTTCGACTTACATGAG |
| 28 | 53 | GGACTCTTCTTGTTTGTGATTAACG |

Example 3

Effect of yvmA Over-Expression on *B. subtilis* Fermentation Broth Color and Pulcherrimin Levels In the instant example, Applicant evaluated the effect of yvmA expression/overexpression in *B. subtilis* cells (strains) comprising a single (1) copy of the gene (1×GG36) encoding the GG36 protease. For example, five (5) ml of a maltrin-based defined media were inoculated to OD 0.02 ($A_{600}$) with either the parental *B. subtilis* strain (i.e., 1×GG36 strain encoding the GG36 protease; e.g., see Example 2) or a modified *B. subtilis* (daughter) strain derived therefrom, which modified daughter strains further comprise an introduced yvmA expression cassette selected from the group consisting of the PspoVG-yvmA cassette (SEQ ID NO: 18), the Phbs-yvmA cassette (SEQ ID NO: 19), the PyvyD-yvmA cassette (SEQ ID NO: 20) and the PpstS-yvmA cassette (SEQ ID NO: 21), as generally set forth in FIG. 1.

More particularly, the inoculated cultures were incubated at 37° C. with 250 RPM shaking with three (3) biological replicates, using a seventy-two (72) hour incubation period. For example, digital images were taken of the cultures at twenty-four (24), forty-eight (48), seventy-two (72) hours (FIG. 2A). As shown in FIG. 2A, a decrease in the red/brown color of the broth was readily observable in the modified *B. subtilis* (daughter) strains comprising the yvmA expression cassettes (i.e., PspoVG-yvmA, SEQ ID NO: 18; Phbs-yvmA, SEQ ID NO: 19; PyvyD-yvmA, SEQ ID NO: 20 and PpstS-yvmA, SEQ ID NO: 21) compared to the parental strain (1×GG36) across the fermentation time course. Likewise, as presented in FIG. 2B, an increase in the luminance of the yvmA expression strains compared/relative to the parental strain (1×GG36) during the same time course was also readily apparent. For example, luminance was measured using the open source image processing package Fiji, described in Schindelin et al. (2012). Applicant further noted that the degree of observable red/brown color reduction correlates with the strength of the promoter that overexpresses yvmA. For example, the strongest promoter tested, spoVG, reduced the red/brown color more than yvmA expression from the weakest promoter tested, pstS, as shown in FIG. 2B.

In addition, to determine if the reduction in red/brown broth color observed for the yvmA overexpressing strains is due to a reduction in pulcherrimin, Applicant quantified the relative amounts of pulcherrimin produced by the parental and modified (daughter) strains after seventy-two (72) hours (e.g., see FIG. 3A and FIG. 3B). More particularly, the pulcherrimin quantification was performed essentially as described in Uffen and Canale-Parola (1972), and further described herein.

Pulcherrimin Quantification Assay: (i) Pellet cells from a one (1) ml of sample (20 OD600) at 14,000 RPM for one (1) minute and discard supernatant, (ii) resuspend the pellet in one (1) ml methanol; (iii) pellet cells at 14,000 RPM for one (1) minute and discard supernatant, (iv) resuspend the pellet in one (1) ml methanol, (v) pellet cells at 14,000 RPM for one (1) minute and discard supernatant, (vi) wash with one (1) ml of water, (vii) resuspend the pellet in one (1) ml 2N NaOH and incubate at room temperature for thirty (30) minutes, (viii) pellet cells at 14,000 RPM for two (2) minutes, (ix) save two-hundred (200) μl of supernatant and (x) measure the absorbance at 410 nm.

Figure 2B:
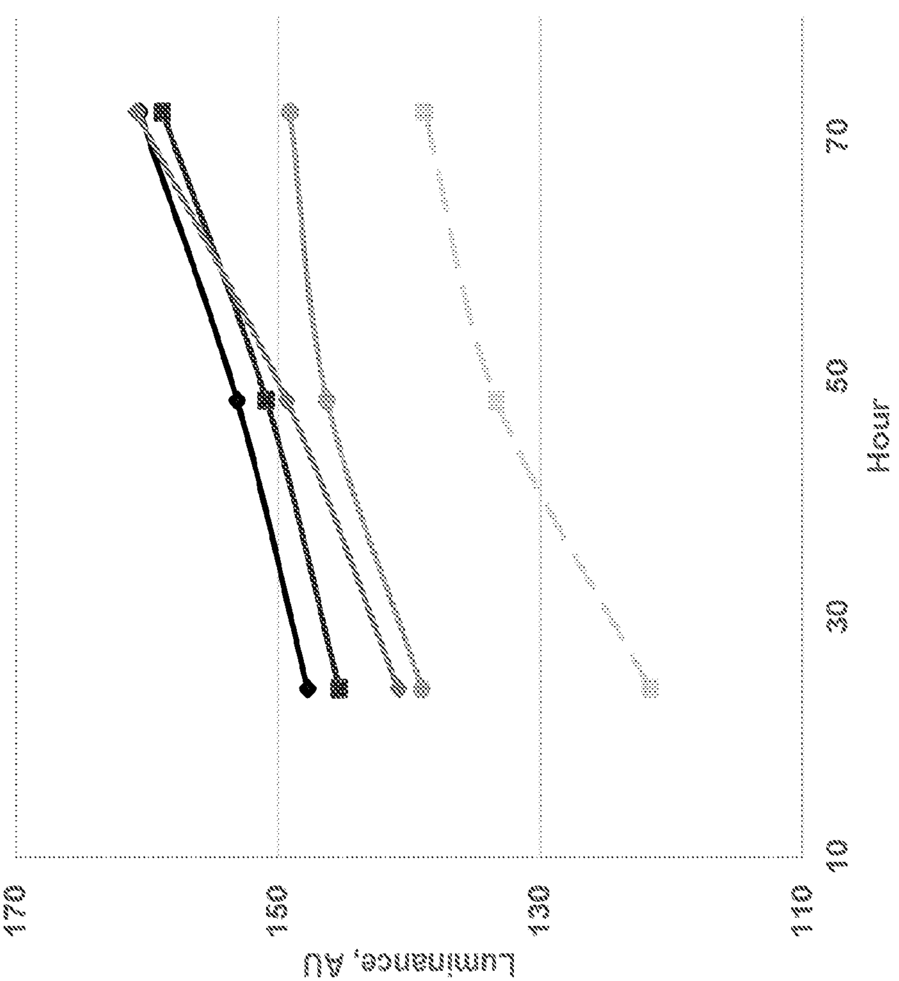

The quantification results of the pulcherrimin produced in the parental (1×GG36) strain relative to the modified (daughter) strains (i.e., comprising yvmA overexpression cassettes) at seventy-two (72) hours are shown in FIG. 3A and FIG. 3B. More particularly, as presented in FIG. 3A, the increased expression of yvmA correlates with an overall reduction in quantifiable pulcherrimin. For example, as shown in FIG. 3A the series of promoters PspoVG, Phbs, PyvyD and PpstS driving the expression of yvmA are presented from left to right (X-axis) in order of promoter strength, such that the PspoVG-yvmA cassette comprises the strongest promoter and the PpstS-yvmA cassette comprises the weakest promoter of the series. Thus, similar to the reduction in visible red/brown color in the broth (FIG. 2), the reduction in pulcherrimin associated with such yvmA overexpression strains particularly correlates with the strength of the promoter used to drive yvmA expression (FIG. 3), wherein the strongest promoter used to drive yvmA expression (i.e PspoVG) resulted in the greatest reduction (decrease) in the amount of pulcherrimin produced and the weakest promoter used (i.e., PpstS) reduced the pulcherrimin level the least. Based on the foregoing, these results demonstrate that the overexpression of yvmA is a particularly suitable method to reduce the red/brown color of *B. subtilis* fermentations, and that the amount of pulcherrimin produced positively correlates with the strength of the promoter used to express yvmA.

Example 4

Generation of *B. subtilis* Strains Expressing Two Copies of a Protein of

Interest and Over-Expressing yvmA

To determine the influence of yvmA overexpression in a 2×GG36 *B. subtilis* strain, a second (2n d) copy of the gene encoding the GG36 protease was introduced into the 1×GG36 Phbs-yvmA strain constructed as described above in Example 2. The correct integration of the expression cassette with the second GG36 copy was verified by PCR analysis and sequence verified. The new strain was stored and named “2×GG36 Phbs-yvmA.”

Example 5 yvmA Over-Expression does not Affect Growth Rate of *B. subtilis* Strains Expressing Two Copies of a Protein of Interest In the present example, Applicant assessed overexpression of yvmA on the growth rate of the *B. subtilis* two (2)

copy GG36 protease strain (2×GG36 Phbs-yvmA) constructed in Example 4. For example, five (5) ml of defined media was inoculated to 0.02 A600 with the control *B. subtilis* strain comprising two (2) copies (2×GG36) of the cassette encoding the GG36 protease and the modified (isogenic) *B. subtilis* strain (2×GG36 Phbs-yvmA) strain which further comprises the integrated Phbs-yvmA expression cassette. Three (3) biological replicates of the control (2×GG36) strain and three (3) biological replicates of the modified (2×GG36 Phbs-yvmA) strain were fermented for ninety (90) hours at 37° C. with 250 RPM shaking. The growth rate of the strains was monitored by A600 spectrometer absorbance of samples taken at eighteen (18), twenty-four (24), forty (40) and ninety (90) hours. As presented in FIG. 4A, the spectrometer analysis shows that the growth rates of the control (2×GG36) and modified (2×GG36 Phbs-yvmA) strains are not significantly different, demonstrating that yvmA overexpression from the hbs promoter (Phbs) does not adversely affect the growth rate of *B. subtilis* (cells) strains expressing two copies of an exemplary protein of interest (POI), e.g., an alkaline serine protease.

Example 6 yvmA Over-Expression does not Affect Protein Production in *B. subtilis Strains Expressing Two Copies of a Protein of Interest*

In the instant example, Applicant assessed overexpression of yvmA on protease production in the two (2) copy *B. subtilis* strains described in Example 5 (i.e., 2×GG36 and 2×GG36 Phbs-yvmA). For example, aliquots were taken at time point eighteen (18), twenty-four (24), forty (40) and ninety (90) hours from the 2×GG36 control and 2×GG36 Phbs-yvmA (modified) strains. A protease activity assay was performed to determine the effect of yvmA overexpression from the hbs promoter (Phbs) on the production of the GG36 protease, as generally described in European Patent No. EP0283075. The results of the protease assay, as set forth in FIG. 4B, demonstrate that there is no significant negative affect of yvmA over-expression on protease production.

Example 7 yvmA Over-Expression Reduces Pulcherrimin Produced by *B. subtilis Strains Expressing Two Copies of a Protein of Interest*

In the present example, the effect of yvmA overexpression on pulcherrimin production in the two (2) copy protease background was determined by comparing pulcherrimin levels produced by the 2×GG36 control and the 2×GG36 Phbs-yvyD (modified) strains. For example, five (5) ml of maltrin-based media was inoculated to OD 0.02 ($A_{600}$) with the control 2×GG36 and 2×GG36 Phbs-yvmA (modified) strains, wherein the pulcherrimin levels of three (3) biological replicates were analyzed after sixty-seven (67) hours using the pulcherrimin quantification assay described above (see, Example 3). More particularly, as presented in FIG. 4C, the *B. subtilis* 2×GG36 Phbs-yvmA (modified) strain produces significantly less pulcherrimin than the control 2×GG36 strain, thereby demonstrating that the amount of pulcherrimin produced is mitigated in such *B. subtilis* cells by over-expressing yvmA.

Example 8

Deletion of yvmA Increases Pulcherrimin Levels and the Observed Red Fermentation Broth Color As generally described in the preceding examples, heterologous yvmA expression significantly reduces the pulcherrimin levels (and red/brown color) in the fermentation broth. Based on the foregoing, Applicant contemplates herein that the functional YvmA protein acts/functions as an transporter of either pulcherrimin, or one of the molecules that constitute pulcherrimin (i.e., pulcherriminic acid and $Fe^{3+}$). For example, as generally described above in Section II, the YvmA protein has twelve (12) predicted transmembrane (TM) domains and primary (1°) amino acid sequence characteristics of a member of the transporter Major Facilitator Superfamily (MSF) described in Karp et al. (2017). Thus, in the instant example, Applicant disrupted the yvmA locus to better understand YvmA protein function. More particularly, the yvmA gene was disrupted (ΔyvmA) in 1×GG36 strain background by whole genome transfer of genomic DNA that was harvested from BKE35090 (ΔyvmA::erm trpC2), which was purchased from *Bacillus* Genetic Stock Center. The presence of the deletion was confirmed by PCR analysis with oligos 52 and 53 (see, TABLE 2 above).

Thus, the 1×GG36 parental strain (Example 2), the 1×GG36 PspoVG-yvmA (modified) strain (Example 2) and the 1×GG36 ΔyvmA (modified) strain constructed as described above, were inoculated A600 0.02 in a maltrin-based media and grown at 37° C. with 250 RPM shaking. After forty-eight (48) hours, the color of the yvmA disrupted strain (1×GG36 ΔyvmA) was more visibly red/brown than the parental (1×GG36) strain and/or the yvmA overexpression strain (1×GG36 PspoVG-yvmA), as shown in FIG. 5A. In addition, the yvmA overexpression strain (1×GG36 PspoVG-yvmA) produced less red/brown broth color than the parental (1×GG36) strain (FIG. 5A). Likewise, aliquots of the fermentations were taken after twenty-four (24) hours and the amount of pulcherrimin produced was determined by the pulcherrimin quantification assay described in Example 3. As presented in FIG. 5B, the pulcherrimin quantification assay demonstrated that the yvmA disrupted strain (1×GG36 ΔyvmA) produces more pulcherrimin than the parental (1×GG36) strain or the yvmA overexpression strain (1×GG36 PspoVG-yvmA). Based on the foregoing, the results of the yvmA disrupted strain (1×GG36 ΔyvmA) further suggest that the YvmA protein functions as a pulcherrimin transporter and/or a pulcherriminic acid transporter and/or an $Fe^{3+}$ transporter.

Example 9

$AlCl_3$ Pre-Addition to a *B. subtilis* Fermentation Reduces the Red Color and Pulcherrimin Levels in the Fermentation Broth As generally understood, pulcherrimin forms by the coordination of three (3) pulcherriminic acid molecules with ferric iron ($Fe^{3+}$), e.g., see Uffen and Canale-Parola (1972). In the instant example, Applicant has contemplated whether the pre-addition of aluminum chloride ($AlCl_3$) to a *Bacillus* fermentation could reduce, mitigate or eliminate pulcherrimin formation (e.g., by the partial or complete substitution of the $Fe^{3+}$ ions with $Al^{3+}$ ions. To test this hypothesis, the high pulcherrimin producing yvmA disrupted strain (1×GG36 ΔyvmA) described above in Example 8, was co-fermented with increasing amounts of aluminum chloride ($AlCl_3$). Thus, the 1×GG36 ΔyvmA cells were inoculated to 0.02 A600 in a maltodextrin-based media and grown at 37° C. with shaking at 250 RPM for fifty (50) hours in the presence of 0 mM, 1 mM, 2 mM, 5 mM and 10 mM $AlCl_3$ (MilliporeSigma, MO).

Figure 6A:
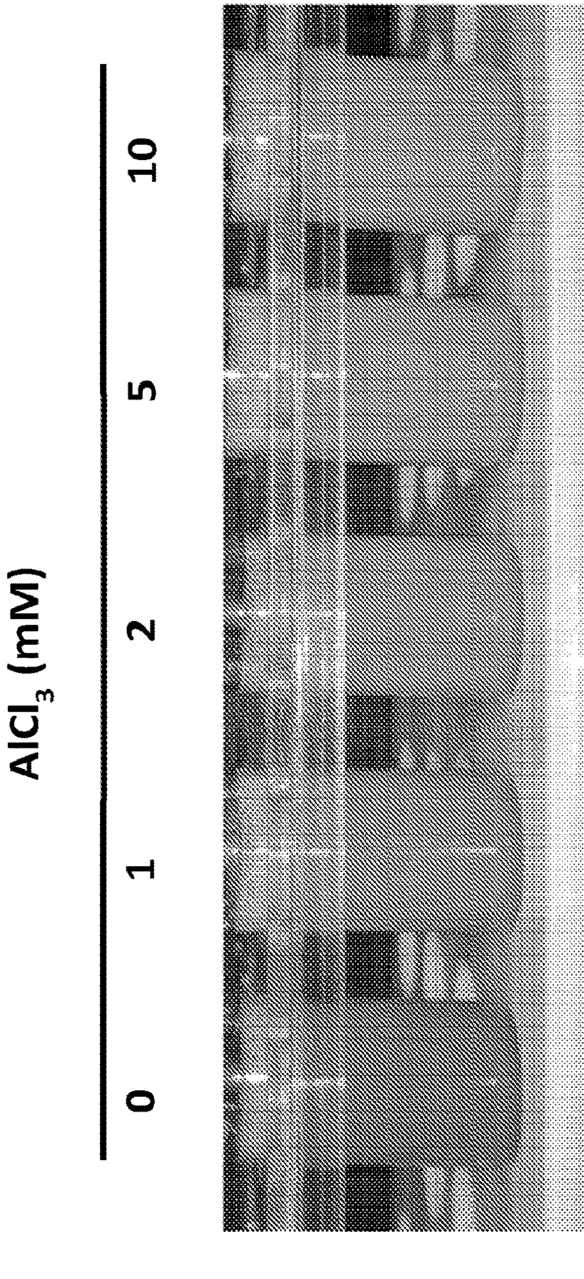
FIG. 6A shows that pre-addition of $AlCl_3$ to a 1×GG36 ΔyvmA *B. subtilis* fermentation reduces the visible red/brown color.
Figure 6A:
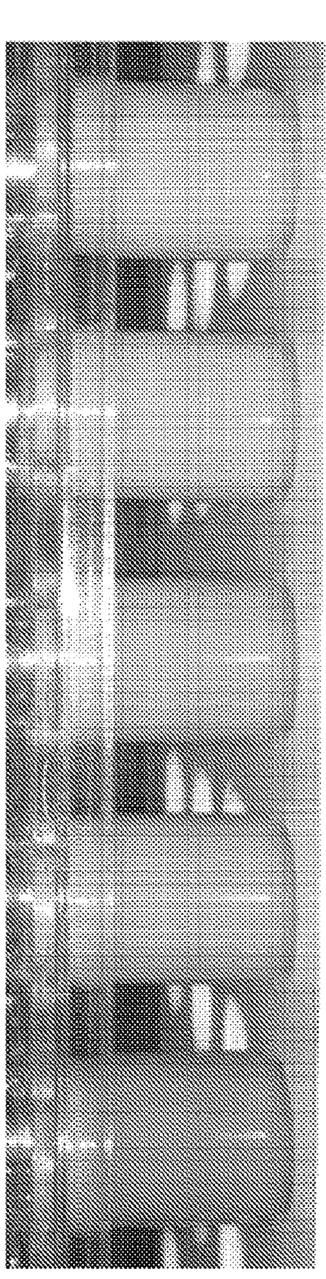
Figure 6B:
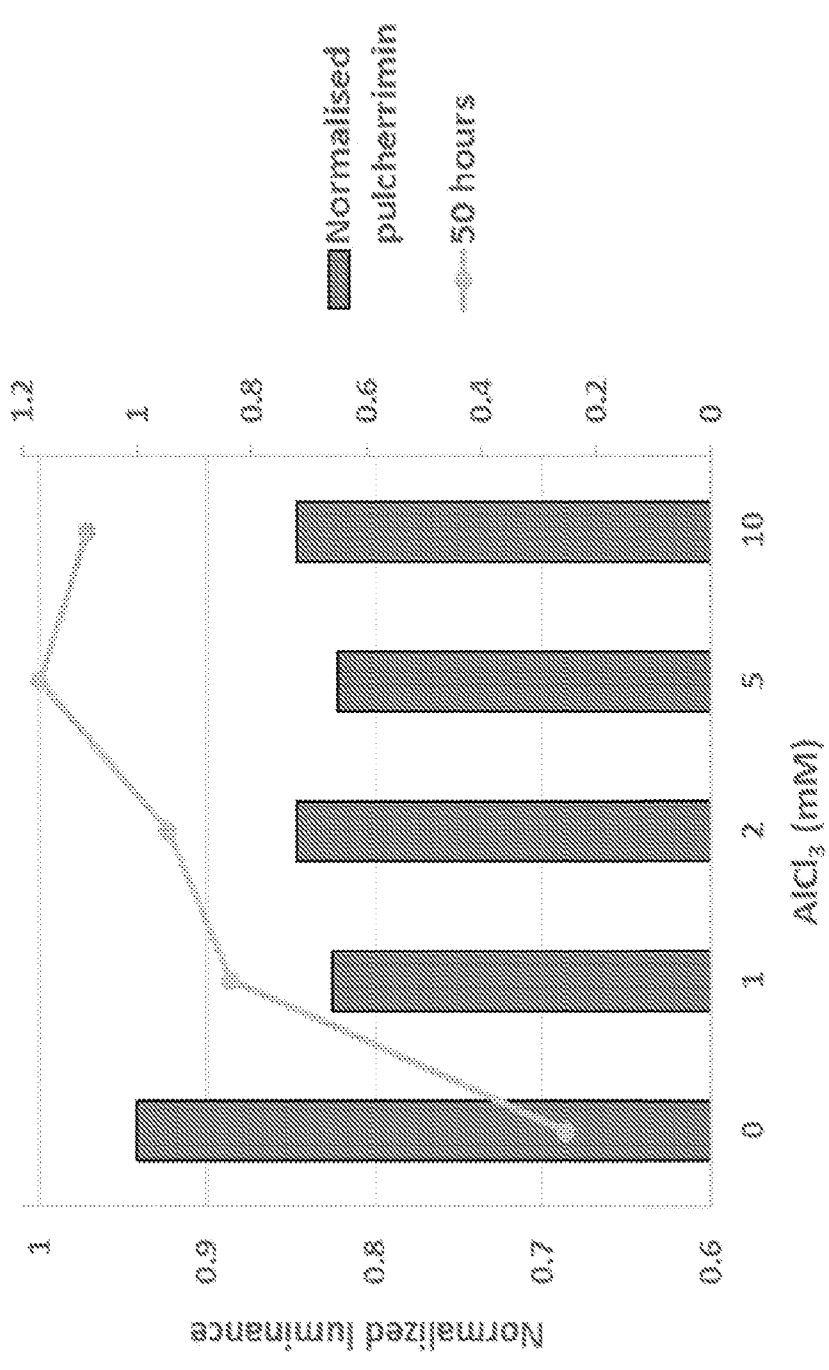
FIG. 6B demonstrates that the pre-addition of $AlCl_3$ to a 1×GG36 ΔyvmA *B. subtilis* fermentation increases luminance at fifty (50) hours, and reduces pulcherrimin levels in the fermentation broth. For example, histograms of luminance of 1×GG36 ΔyvmA cultures with added 0 mM, 1 mM, 2 mM, 5 mM and 10 mM $AlCl_3$ are shown after fifty (50) hours in FIG. 6B, left y-axis and the pulcherrimin detectable in the broth of 1×GG36 ΔyvmA cultures with pre-addition of 0 mM, 1 mM, 2 mM, 5 mM and 10 mM $AlCl_3$ after fifty (50) hours of growth is shown in FIG. 6B, right y-axis.
Figure 6C:
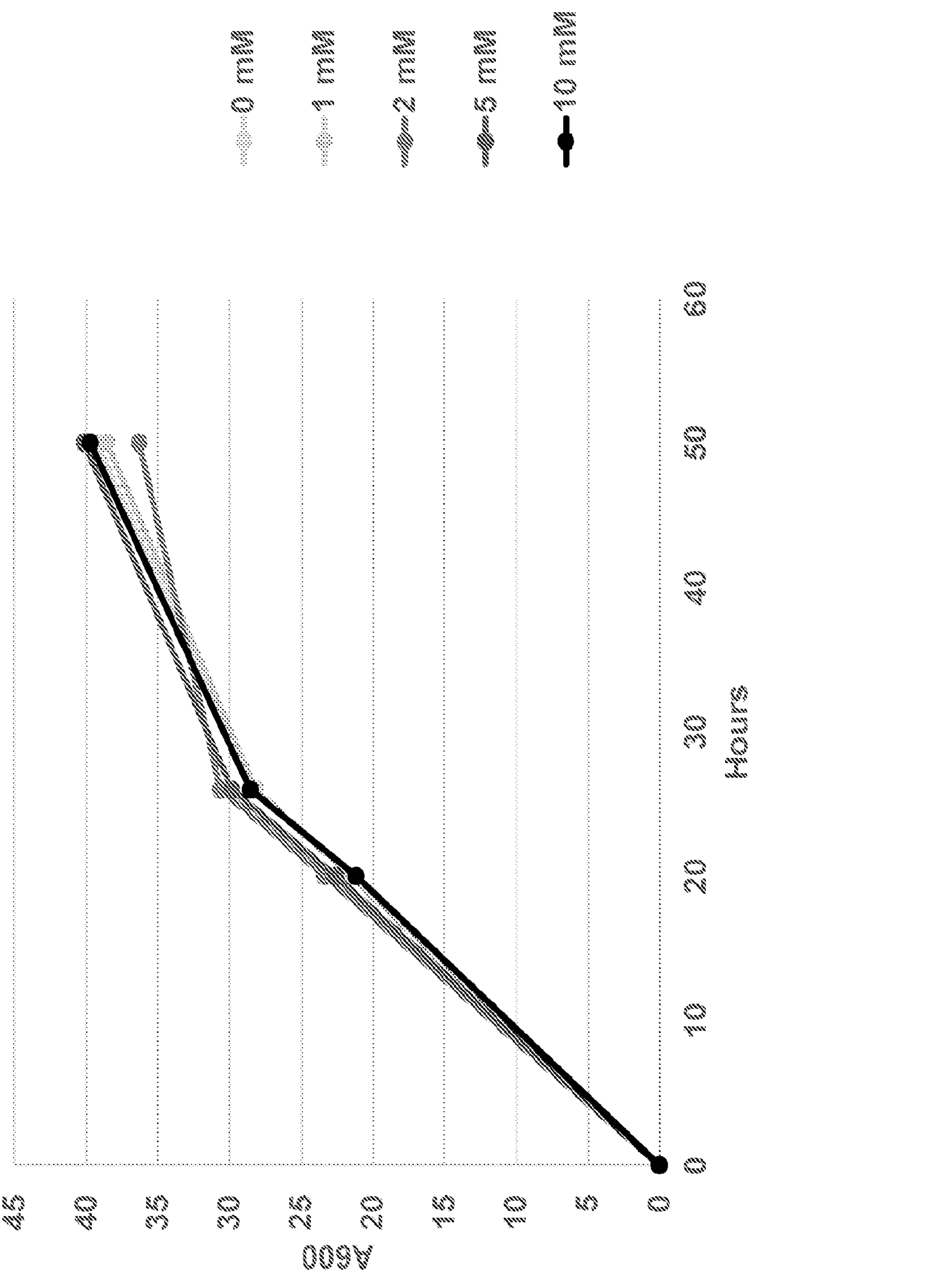
As shown in FIG. 6C, pre-addition of $AlCl_3$ does not affect the growth rate of the *B. subtilis* 1×GG36 ΔyvmA cells grown in the presence of 0 mM, 1 mM, 2 mM, 5 mM and 10 mM $AlCl_3$ for fifty (50) hours at 37° C. in a maltrin-based media. As presented in FIG. 6D, protease production (activity) of 1×GG36 ΔyvmA cells was not affected when grown in the presence of 0 mM, 1 mM, 2 mM, 5 mM and 10 mM $AlCl_3$ for fifty (50) hours at 37° C. in a maltrin-based media, wherein protease activity was measured at twenty (20), twenty-six (26) and fifty (50) hour time points.
Figure 6D:
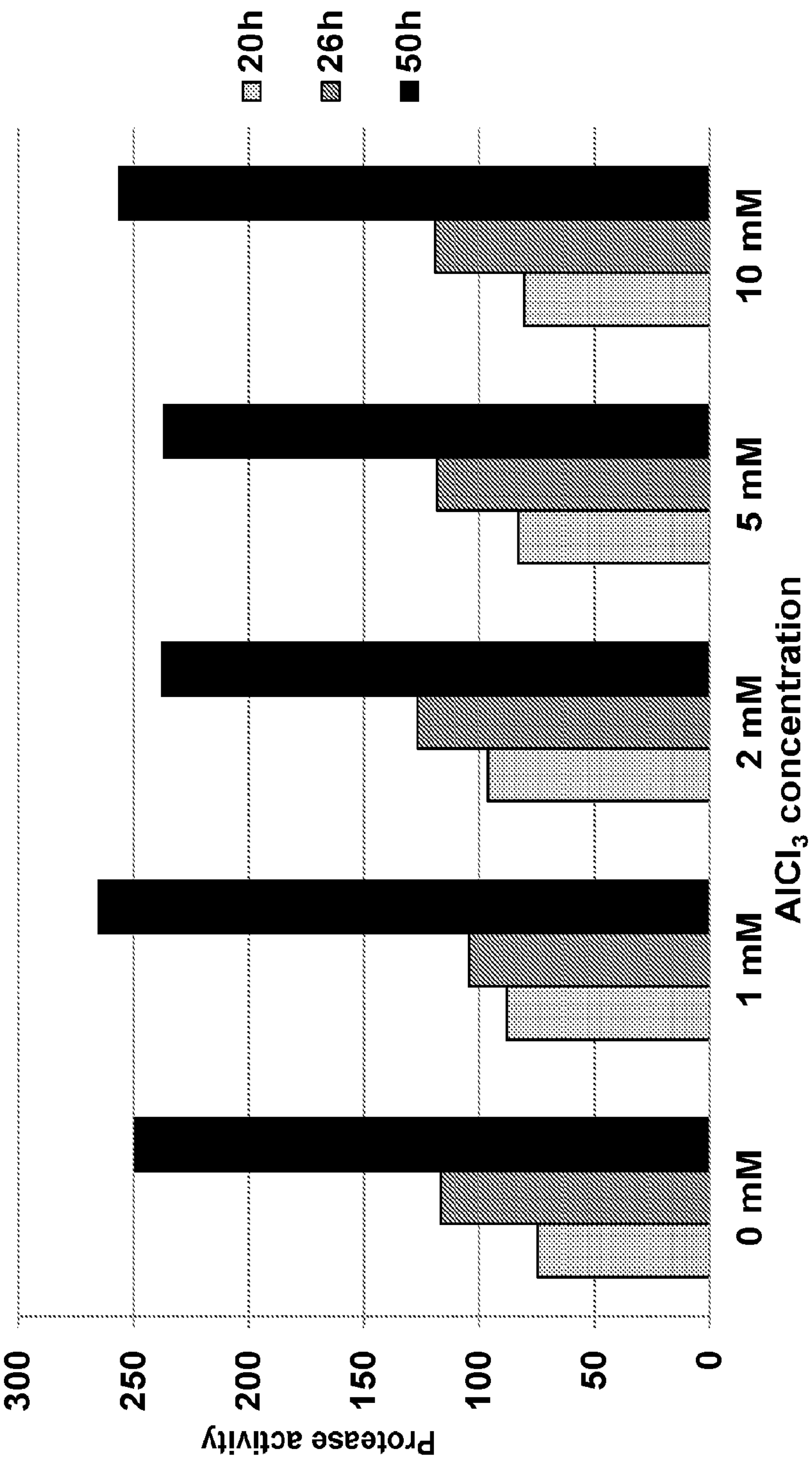
FIG. 6 shows that the pre-addition of $AlCl_3$ to *B. subtilis* fermentations reduces the red/brown color and pulcherrimin level, and does not affect growth or protease production (e.g., see FIG. 6A-6D). For example.

For example, as presented in FIG. 6A, after twenty (20) hours of growth, a reduction in the red/brown color in the fermentation broth was visible. The reduction of red/brown color was more apparent after fifty (50) hours, wherein the reduction in red/brown color positively correlates with the increasing concentrations of aluminum chloride ($AlCl_3$). As shown in FIG. 6B (left axis), the relative luminance of these cultures was determined by Fiji image processing software, wherein the luminance increases (positively) correlate with concentrations of aluminum chloride [$AlCl_3$] pre-addition to the 1×GG36 ΔyvmA strain fermentations at the fifty (50) hour timepoint. In addition, aliquots of the 1×GG36 ΔyvmA strain with pre-addition of aluminum chloride ($AlCl_3$) were taken at the fifty (50) hour time point, as presented in FIG. 6B (right axis), wherein the relative amount of pulcherrimin in these samples was determined using the pulcherrimin quantification assay described in Example 3. For example, as shown in FIG. 6B (right axis), the amount of pulcherrimin detected in the 1 mM, 2 mM, 5 mM and 10 mM aluminum chloride ($AlCl_3$) experimental conditions was less than the 1×GG36 ΔyvmA control fermentation without pre-addition of aluminum chloride ($AlCl_3$).

Example 10

$AlCl_3$ Pre-Addition to a *B. subtilis* Fermentation does not Affect Growth Rate In the instant example, Applicant assessed the fermentation growth rate of the yvmA disrupted strain (1×GG36 ΔyvmA; Example 8) with pre-addition of aluminum chloride ($AlCl_3$). More particularly, the growth rate of the 1×GG36 ΔyvmA strain with pre-addition of aluminum chloride ($AlCl_3$) was monitored by spectrometer analysis of aliquots taken at twenty (20), twenty-six (26) and fifty (50) hours. As presented in FIG. 6C, over the course of the fifty (50) hour fermentation period, the growth rate of the 1×GG36 ΔyvmA cells that were co-fermented with 1 mM, 2 mM, 5 mM and 10 mM aluminum chloride ($AlCl_3$) did not diverge from the control 1×GG36 ΔyvmA fermentation growth rate (i.e., without $AlCl_3$ pre-addition). These results demonstrate that the pre-addition of at least 10 mM aluminum chloride ($AlCl_3$) does not significantly affect the growth rate of *B. subtilis* strains expressing/producing a protein of interest.

Example 11

$AlCl_3$ Pre-Addition to a *B. subtilis* Fermentation does not Affect Production of a Protein of Interest The present example assessed the production of the GG36 protease during fermentation of the yvmA disrupted strain (1×GG36 ΔyvmA; Example 8) with pre-addition of aluminum chloride ($AlCl_3$). More particularly, protease production was monitored by protease assay of aliquots taken at twenty (20), twenty-six (26) and fifty (50) hours, as generally described in European Patent No. EP0283075. As presented in FIG. 6D, over the course of the fifty (50) hour fermentation period, the amount of protease activity produced by the yvmA disrupted cells (1×GG36 ΔyvmA) that were co-fermented with 1 mM, 2 mM, 5 mM and 10 mM aluminum chloride ($AlCl_3$), did not diverge from the yvmA disrupted control (1×GG36 ΔyvmA fermentation) which was grown without aluminum chloride ($AlCl_3$) pre-addition. These results demonstrate that pre-addition of at least ten (10) mM aluminum chloride ($AlCl_3$) does not significantly affect the amount of the protein of interest produced during growth/cultivation/fermentation of such *B. subtilis* (cells) strains.

Example 12

Construction of *B. licheniformis* Strains Expressing *B. subtilis* yvmA from Heterologous Promoters In the present example, two (2) *B. licheniformis* strains containing a gene encoding the wild-type RghR2 protein (SEQ ID NO: 29) were constructed such that the strains express functional *B. subtilis* YvmA protein (SEQ ID NO: 30). More specifically, the cassettes were inserted in the amyL locus (SEQ ID NO: 31) and carried a tetA selectable marker cassette (SEQ ID NO: 32).

The first cassette, amyL::[Phbs-yvmA tetR] (SEQ ID NO: 33) contained a 5' amyL homology arm (SEQ ID NO: 34) linked to the hbs promoter (Phbs) from *B. subtilis* (SEQ ID NO: 35) operably linked to the Shine-Dalgarno sequence of the *B. subtilis* spoVG gene (SEQ ID NO: 36) operably linked to the (yvmA) DNA sequence (SEQ ID NO: 37) encoding the *B. subtilis* YvmA protein (SEQ ID NO: 30) operably linked to the *B. subtilis* yvmA terminator (SEQ ID NO: 38) linked to the expression cassette for tetA (SEQ ID NO: 32) encoding tetracycline resistance linked to a 3' amyL homology arm (SEQ ID NO: 39).

The second cassette, amyL::[PspoVG-yvmA tetR] (SEQ ID NO: 40) contained a 5' amyL homology arm (SEQ ID NO: 34) linked to the spoVG promoter (PspoVG) from *B. subtilis* (SEQ ID NO: 41) operably linked to the Shine-Dalgarno sequence of the *B. subtilis* spoVG gene (SEQ ID NO: 36) operably linked to the (yvmA) DNA sequence (SEQ ID NO: 37) encoding *B. subtilis* the YvmA protein (SEQ ID NO: 30) operably linked to the *B. subtilis* yvmA terminator (SEQ ID NO: 38) linked to the expression cassette for tetA (SEQ ID NO: 32) encoding tetracycline resistance linked to a 3' amyL homology arm (SEQ ID NO: 39).

The amyL::[Phbs-yvmA tetR] and amyL::[PspoVG-yvmA tetR] cassettes were integrated into the parental *B. licheniformis* host using the protocol previously described in PCT Publication No. WO2018/136459 (incorporated herein by reference in its entirety). The cells were selected on L agar containing ten (10) ppm tetracycline. To analyze the transformant cells, the amyL locus (SEQ ID NO: 31) was amplified using the primers set forth below in TABLE 3.

TABLE 3

FORWARD AND REVERSE PRIMERS FOR CASSETTE VERIFICATION

| Name | Sequence | SEQ ID NO |
|---|---|---|
| 1762 | CGCTTCTTGAAAACGAGGTG | 42 |
| 1763 | GCTCATCCAAATCGATCCCA | 43 |

Colonies with the correct PCR product for either amyL::[Phbs-yvmA tetR] (SEQ ID NO: 44) or amyL::[PspoVG-yvmA tetR] (SEQ ID NO: 45) cassettes were verified using DNA sequencing by the method of Sanger with the primers set forth below in TABLE 4.

TABLE 4

| FORWARD AND REVERSE PRIMERS FOR CASSETTE VERIFICATION | | |
|---|---|---|
| Name | Sequence | SEQ ID NO |
| 2377 | GCAGATGCTGCTGAAGAGAT | 46 |
| 2378 | GCTCCAGTTCTAGGAGGATT | 47 |
| 2379 | GGGTTAATGATACGCTTCCC | 48 |

Two independent isolates with the correct sequence for the amyL::[Phbs-yvmA tetR] (SEQ ID NO: 33) were stored as strains BF1175 and BF1176. Two independent isolates with the correct sequence for the amyL::[PspoVG-yvmA tetR] (SEQ ID NO: 40) were stored as strains BF1177 and BF1178, as presented below in TABLE 5.

TABLE 5

| STRAINS CONSTRUCTED | | |
|---|---|---|
| Name | Cassette | Cassette (SEQ ID NO) |
| BF62 | None | NA |
| BF1175 | amyL::[Phbs-yvmA tetR] | 5 |
| BF1176 | amyL::[Phbs-yvmA tetR] | 5 |
| BF1177 | amyL::[PspoVG-yvmA tetR] | 12 |
| BF1178 | amyL::[PspoVG-yvmA tetR] | 12 |

Example 13

Determination of Pulcherrimin Produced by *B. licheniformis* Strains Expressing *B. subtilis* yvmA In the present example the amount of pulcherrimin produced by *B. licheniformis* cells expressing the *B. subtilis* YvmA protein (SEQ ID NO: 30) was assessed by extracting the sodium salt of pulcherrimin from the whole broth culture of the cells. Briefly, either the parental strain or the strains carrying either of the two different *B. subtilis* yvmA expression cassettes (TABLE 5) were grown under flask conditions as described in PCT Publication No. WO2018/156705 (incorporated herein by reference in its entirety). After one-hundred (100) hours of growth at 37° C. and 250 RPM agitation, the amount of pulcherrimin produced was assayed as follows. The culture was pelleted at 4000 RPM for ten (10) minutes. The pellet was washed twice in 100% methanol and twice with dd$H_2O$. The pellet was resuspended in 1 ml of 2N NaOH and incubated at room temperature for 15 minutes. The debris was removed by centrifugation at 14000 RPM for two (2) minutes. The supernatant was removed from the debris and the absorbance of the supernatant was measured at 405 nm to quantify the relative amount of sodium pulcherrimate. The Absorbance and relative absorbance to the parental strain is shown in TABLE 6 below.

TABLE 6

| QUANTIFICATION OF PULCHERRIMIN PRODUCTION | | | | |
|---|---|---|---|---|
| Strain | Cassette | Cassette SEQ ID NO | A405 | Rel. to BF62 |
| BF62 | None | NA | 0.30 | 1.0 |
| BF1175 | amyL::[Phbs-yvmA tetR] | 5 | 0.09 | 0.30 |
| BF1176 | amyL::[Phbs-yvmA tetR] | 5 | 0.13 | 0.43 |
| BF1177 | amyL::[PspoVG-yvmA tetR] | 12 | 0.13 | 0.43 |
| BF1178 | amyL::[PspoVG-yvmA tetR] | 12 | 0.12 | 0.40 |

As indicated in TALE 6, expression of the *B. subtilis* YvmA protein in *B. licheniformis* from either of two (2) heterologous promoters (Phbs and PspoVG) reduces the amount of pulcherrimin present outside the cells by more than 50% in all cases tested, suggesting that the use of the *B. subtilis* YvmA protein to reduce the presence of pulcherrimin can be used in a broad spectrum of species that produce this compound.

Example 14

$AlCl_3$ or $Al_2(SO_4)_3$ Pre-Addition to a *Bacillus* Fermentation Lightens the Broth Color In the present example, *Bacillus* fermentations were used to assess/determine if the (red/brown) color reducing benefit of the aluminum ion described in the preceding examples is applicable to industrially relevant conditions (e.g., high cell density, industrial fermentation processes, etc.). For example, in two (2) L bioreactors (fermentors), 10 mM $AlCl_3$ or 5 mM $Al_2(SO_4)_3$ (MilliporeSigma, MO) were added upfront (pre-addition) to the fermentation media and the protease production fermentation process ran forty (40) hours. In addition, two other bioreactors, which were not supplemented with aluminum, were run in parallel to provide a baseline for comparison. LAB color assay of the twenty (20) hour and forty (40) hour whole broth samples indicated significantly lighter broth color (i.e., higher L value) for the cases with aluminum by the end of fermentation (e.g., see FIG. 7 and TABLE 7 below).

TABLE 7

| QUANTIFICATION OF PULCHERRIMIN PRODUCTION | | |
|---|---|---|
| Fermentation | L-Value after 20 hr | L-Value after 40 hr |
| Control-1 | 48.31 ± 0.67 | 58.28 ± 0.30 |
| Control-2 | 49.08 ± 0.90 | 59.35 ± 0.27 |
| Batched $AlCl_3$ | 48.25 ± 0.60 | 64.16 ± 0.41 |
| Batched $Al_2(SO_4)_3$ | 50.27 ± 0.70 | 66.48 ± 0.10 |

Example 15

$AlCl_3$ or $Al_2(SO_4)_3$ Pre-Addition to a *Bacillus* Two Liter Fermentation does not Affect Growth Rate Cell mass and respiration status did not vary significantly between the four fermentors. The cell mass, as monitored by spectrometer analysis, were within an average deviation of 8%. The respiration status, as interpreted through carbon evolution and oxygen uptake rate trends were very comparable, further indicating that 10 mM aluminum ion, whether in the form of AlC13 or Al2(SO4)3, has no effect on *Bacillus* growth in such industrial fermentation conditions. For example, a fully aerated fed-batch fermentation was carried out in 2 L bioreactors, wherein temperature and pH were controlled. Dissolved oxygen was controlled at greater than or equal to 50% saturation by adjusting air flow and agitation rates, which were set to initial rates of 30 slph and 750 rpm respectively. Each bioreactor was inoculated with 3 mL of the starter culture grown from the frozen stock of protease expressing *B. subtilis* strain in 30 mL of LB supplemented with 1% glucose in 250 mL shake flasks at 37° C. and 170 rpm until the optical density at 550 nm reached 0.8-1.5. Online gas analysis was used to monitor the respiration status of the fermentation culture. Whole broth samples were collected periodically for offline optical density, LAB color, and active protease quantification. LAB color analysis: Whole broth samples were analyzed in duplicate using a Hunter Lab color meter (LabScan XE, HunterLab, USA), as described in U.S. Pat. No. 6,303,354. The output of interest was the L-value which indicates the lightness of the analyte, where a reading of 0 indicates black and a reading of 100 indicates white.

Example 16

$AlCl_3$ or $Al_2(SO_4)_3$ Pre-Addition to a *Bacillus* Two Liter Fermentation does not Affect Protease Production Protease production was not impacted by aluminum pre-addition when compared to the control fermentations. Protease concentrations were determined via activity assay for the twenty (20) hour and forty (40) hour fermentation broth samples. Considering the respective batched and fed carbon for each sample, total carbon yield was also determined. All four fermentations successfully reached the titers and yields appropriate for the scale's capabilities.

Active protease quantification: In the pNA peptidyl assay, the hydrolysis rate of N-suc-AAPF-pNA as caused by protease activity is apparent in the measurable production of yellow color, and is measurable at 405 nm on a spectrophotometer, as generally describe in U.S. Patent Publication No. US20200123522A1. Standards and samples were first diluted with 100 mM Tris pH 8.6 solution such that their concentration was within the appropriate range for the assay. Sample was then added to cuvettes containing 1 mg/mL suc-AAPF-pNA and assayed at 405 nm over three (3) minutes using a spectrophotometer in kinetic mode at room temperature. A calibration curve correlating hydrolysis rate expressed in mOD*min−1 and enzyme concentration was generated using standards of known enzyme concentration, and the active enzyme concentrations of the whole broth samples were thereby determined.

REFERENCES

PCT Publication No. WO1990/11352
PCT Publication No. WO1994/18314
PCT Publication No. WO1999/19467
PCT Publication No. WO1999/43794
PCT Publication No. WO2000/29560
PCT Publication No. WO2000/60059
PCT Publication No. WO2001/51643
PCT Publication No. WO2002/14490
PCT Publication No. WO2003/083125
PCT Publication No. WO2003/089604
PCT Publication No. WO2004/011609
PCT Publication No. WO2006/037483
PCT Publication No. WO2006/037484
PCT Publication No. WO2006/089107
PCT Publication No. WO2008/112459
PCT Publication No. WO2011/140316
PCT Publication No. WO2012/151534
PCT Publication No. WO2014/164777
PCT Publication No. WO2015/089447
PCT Publication No. WO2016/183509
PCT Publication No. WO2018/156705
PCT Publication No. WO2020/242858
U.S. Pat. No. 5,972,682
U.S. Pat. No. 6,303,354
U.S. Patent Publication No. US2020/0123522

Arnaouteli et al., "Pulcherrimin formation controls growth arrest of the *Bacillus subtilis* biofilm", *PNAS,* 116(27): 13553-13562, 2019.

Botstein and Shortle, *Science* 229: 4719, 1985.

Brode et al., "Subtilisin BPN' variants: increased hydrolytic activity on surface-bound substrates via decreased surface activity", *Biochemistry,* 35(10):3162-3169, 1996.

Chang et al., *Mol. Gen. Genet.,* 168:11-115, 1979.

Ferrari et al., "Genetics," in Harwood et al. (ed.), *Bacillus*, Plenum Publishing Corp., 1989.

Fisher et. al., *Arch. Microbiol.,* 139:213-217, 1981.

Higuchi et al., *Nucleic Acids Research* 16: 7351, 1988.

Ho et al., *Gene* 77: 61, 1989.

Hoch et al., *J. Bacteriol.,* 93:1925-1937, 1967.

Holubova, *Folia Microbiol.,* 30:97, 1985.

Horton et al., *Gene* 77: 61, 1989.

Iglesias and Trautner, *Molecular General Genetics* 189: 73-76, 1983.

Jensen et al., "Cell-associated degradation affects the yield of secreted engineered and heterologous proteins in the *Bacillus subtilis* expression system" *Microbiology,* 146, Pt 10:2583-2594, 2000.

Karp et al., "The BioCyc collection of microbial genomes and metabolic pathways", *Briefings in Bioinformatics,* 2017.

Li et al., "Identification and High-level Production of Pulcherrimin in *Bacillus licheniformis DW2", Appl Biochem Biotechnol.,* 183(4):1323-1335, 2017.

Lo et al., *Proceedings of the National Academy of Sciences USA* 81: 2285, 1985.

MacDonald, "Biosynthesis of pulcherriminic acid", *Biochem. J.,* 96: 533-538, 1965.

MacDonald, "The isolation of pulcherriminic acid from *Bacillus cereus", Canadian Journal of Microbiology,* 13(1), 1967.

Mann et al., *Current Microbiol.,* 13:131-135, 1986.

McDonald, *J. Gen. Microbiol.,* 130:203, 1984.

Pao et al., "Major facilitator superfamily", *Microbiology and Molecular Biology Reviews,* 62(1):1-34, 1998.

Pawlikowska et al., "Biocontrol capability of local *Metschnikowia* sp. Isolates", *Antonie Van Leeuwenhoek,* 112(10): 1425-1445, 2019.

Perego, 1993, In A. L. Sonneshein, J. A. Hoch, and R. Losick, editors, *Bacillus subtilis and Other Gram-Positive Bacteria*, Chapter 42, American Society of Microbiology, Washington, D.C.

Pi and Helmann, "Ferrous iron efflux systems in bacteria", *Metallomics,* 9(7):840-851, 2017.

Randazzo et al, "The MarR-like protein PchR (YvmB) regulates expression of genes involved in pulcherriminic acid biosynthesis and in the initiation of sporulation in *Bacillus subtilis", BMC Microbiology,* 16:190, 2016.

Raul et al., "Production and partial purification of alpha amylase from *Bacillus subtilis* (MTCC 121) using solid state fermentation", *Biochemistry Research International,* 2014.

Sarkar and Sommer, *Bio Techniques* 8: 404, 1990.
Saunders et al., *J. Bacteriol.,* 157:718-726, 1984.
Schindelin et al., "Fiji—an open source platform for biological image analysis", *Nat Methods.,* 9(7):10, 2012.
Shimada, *Meth. Mol. Biol.* 57: 157; 1996
Sipiczki M., "*Metschnikowia pulcherrima* and Related Pulcherrimin-Producing Yeasts: Fuzzy Species Boundaries and Complex Antimicrobial Antagonism" *Microorganisms,* 8(7): 1029, 2020.
Smith et al., *Appl. Env. Microbiol.,* 51:634 1986.
Uffen and Canale-Parola, "Synthesis of Pulcherriminic Acid by *Bacillus subtilis", Journal of Bacteriology* 111:86-93, 1972.
Van Dijl and Hecker, "*Bacillus subtilis*: from soil bacterium to super-secreting cell factory", *Microbial Cell Factories,* 12(3). 2013.
Vorobjeva et al., *FEMS Microbiol. Lett.,* 7:261-263, 1980.
Westers et al., "*Bacillus subtilis* as cell factory for pharmaceutical proteins: a biotechnological approach to optimize the host organism", *Biochimica et Biophysica Acta.,* 1694: 299-310, 2004.

The invention claimed is:

1. A recombinant *Bacillus* cell obtained by genetically modifying a parental *Bacillus* cell, wherein the recombinant cell comprises an introduced yvmA expression cassette comprising a heterologous promoter operably linked to a yvmA open reading frame (ORF) encoding a functional YvmA protein having at least 95% identity to SEQ ID NO: 30, wherein the recombinant cell produces at least 5% less pulcherrimin than the parental cell when fermented under the same conditions, as determined by (i) pelleting an aliquot of fermentation culture, (ii) washing the pellet with methanol and water, (iii) extracting the pellet with 2N NaOH, and (iv) measuring absorbance at about 405-410 nm.

2. The *Bacillus* cell of claim 1, wherein the parental cell expresses an endogenous protein of interest (POI) or a heterologous POI.

3. The *Bacillus* cell of claim 2, wherein the POI is an enzyme.

4. The *Bacillus* cell of claim 1, wherein the functional YvmA protein comprises twelve (12) transmembrane domains and a major facilitator superfamily (MSF) transporter motif.

5. The *Bacillus* cell of claim 1, wherein the yvmA ORF has at least 95% identity to SEQ ID NO: 37.

6. The *Bacillus* cell of claim 1, wherein the recombinant cell exhibits a growth rate within ±10% of the parental cell under the same conditions, as determined by OD600 over time.

7. The *Bacillus* cell of claim 2, wherein the recombinant cell produces an amount of the POI within ±10% of the parental cell under the same conditions.

8. A method for cultivating a *Bacillus* cell deficient in the production of a red pigment comprising:

modifying a parental *Bacillus* cell by introducing into the parental cell a yvmA expression cassette comprising a heterologous promoter operably linked to a yvmA open reading frame (ORF) encoding a functional YvmA protein having at least 95% identity to SEQ ID NO: 30, and cultivating the recombinant cell under suitable conditions, wherein the recombinant cell produces at least 5% less pulcherrimin than the parental cell when cultivated under the same conditions, as determined by (i) pelleting an aliquot of culture, (ii) washing the pellet with methanol and water, (iii) extracting the pellet with 2N NaOH, and (iv) measuring absorbance at about 405-410 nm.

9. A method for producing a heterologous protein of interest (POI) comprising:

modifying a parental *Bacillus* cell expressing a heterologous POI by introducing into the parental cell an expression cassette comprising a heterologous promoter operably linked to a yvmA open reading frame (ORF) encoding a functional YvmA protein having at least 95% identity to SEQ ID NO: 30, and fermenting the recombinant cell under suitable conditions for the production of the POI, wherein the recombinant cell produces at least 5% less pulcherrimin than the parental cell when fermented under the same conditions, as determined by (i) pelleting an aliquot of culture, (ii) washing the pellet with methanol and water, (iii) extracting the pellet with 2N NaOH, and (iv) measuring absorbance at about 405-410 nm.

10. The method of claim 9, wherein the POI is an enzyme.

11. The method of claim 9, wherein the functional YvmA protein comprises twelve (12) transmembrane domains and a major facilitator superfamily (MSF) transporter motif.

12. The method of claim 9, wherein the yvmA ORF has at least 95% identity to SEQ ID NO: 37.

13. The method of claim 9, wherein the recombinant cell exhibits a growth rate within 10% of the parental cell under the same conditions, as determined by OD600 over time.

14. The method of claim 9, wherein the recombinant cell produces an amount of the POI within 10% of the parental cell under the same conditions.

* * * * *